(12) United States Patent
Barr et al.

(10) Patent No.: US 9,487,490 B2
(45) Date of Patent: Nov. 8, 2016

(54) 3-CYCLOHEXENYL AND CYCLOHEXYL SUBSTITUTED INDOLE AND INDAZOLE COMPOUNDS AS RORGAMMAT INHIBITORS AND USES THEREOF

(71) Applicant: Merck Sharp & Dohme Corp., Rahway, NJ (US)

(72) Inventors: Kenneth J. Barr, Boston, MA (US); John K. Maclean, Brookline, MA (US); Hongjun Zhang, Newton, MA (US); Richard T. Beresis, Shanghai (CN); Dongshan Zhang, Shanghai (CN); Brian M. Andresen, Sharon, MA (US); Neville J. Anthony, Northborough, MA (US); Blair T. Lapointe, Brookline, MA (US); Nunzio Sciammetta, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/421,057

(22) PCT Filed: Aug. 14, 2013

(86) PCT No.: PCT/US2013/054902
§ 371 (c)(1),
(2) Date: Feb. 11, 2015

(87) PCT Pub. No.: WO2014/028597
PCT Pub. Date: Feb. 20, 2014

(65) Prior Publication Data
US 2015/0191434 A1  Jul. 9, 2015

(30) Foreign Application Priority Data

Aug. 15, 2012 (CN) ................. PCT/CN2012/080133

(51) Int. Cl.
| | | |
|---|---|---|
| *C07D 471/04* | (2006.01) |
| *A61K 31/4745* | (2006.01) |
| *C07D 231/56* | (2006.01) |
| *A61K 31/404* | (2006.01) |
| *A61K 31/416* | (2006.01) |
| *A61K 31/437* | (2006.01) |
| *A61K 31/454* | (2006.01) |
| *A61K 31/496* | (2006.01) |
| *A61K 31/5377* | (2006.01) |
| *C07D 209/26* | (2006.01) |
| *C07D 401/06* | (2006.01) |
| *C07D 403/06* | (2006.01) |
| *C07D 405/12* | (2006.01) |
| *C07D 413/06* | (2006.01) |

(52) U.S. Cl.
CPC ........... *C07D 231/56* (2013.01); *A61K 31/404* (2013.01); *A61K 31/416* (2013.01); *A61K 31/437* (2013.01); *A61K 31/454* (2013.01); *A61K 31/496* (2013.01); *A61K 31/5377* (2013.01); *C07D 209/26* (2013.01); *C07D 401/06* (2013.01); *C07D 403/06* (2013.01); *C07D 405/12* (2013.01); *C07D 413/06* (2013.01); *C07D 471/04* (2013.01)

(58) Field of Classification Search
CPC  C07D 401/06; C07D 231/56; C07D 405/12; C07D 471/04; C07D 209/26; C07D 413/06; C07D 403/06
USPC ...................................... 514/210.18
See application file for complete search history.

(56) References Cited

U.S. PATENT DOCUMENTS

| | | | | |
|---|---|---|---|---|
| 5,639,780 A | * | 6/1997 | Lau et al. ............... | 514/419 |
| 9,095,583 B2 | * | 8/2015 | Karstens .............. | C07D 231/56 |
| 2006/0030612 A1 | | 2/2006 | Steffan et al. | |
| 2011/0263046 A1 | | 10/2011 | Deuschle et al. | |
| 2015/0210687 A1 | * | 7/2015 | Barr ..................... | C07D 231/56 |
| | | | | 514/210.18 |
| 2015/0218096 A1 | * | 8/2015 | Barr ..................... | C07D 231/56 |
| | | | | 514/210.15 |

(Continued)

FOREIGN PATENT DOCUMENTS

| | | |
|---|---|---|
| EP | 0429257 A2 | 5/1991 |
| EP | 2181710 A1 | 5/2010 |

(Continued)

OTHER PUBLICATIONS

El-Sawy; Acta Pharm. 2012, 62,157-179.*

(Continued)

*Primary Examiner* — Noble Jarrell
*Assistant Examiner* — Daniel Carcanague
(74) *Attorney, Agent, or Firm* — Goodwin Procter LLP

(57) ABSTRACT

The present invention relates to compounds according to Formula I and pharmaceutically acceptable salts or solvates thereof. Such compounds can be used in the treatment of RORgammaT-mediated diseases or conditions.

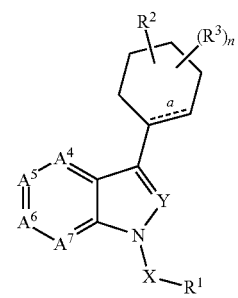

24 Claims, No Drawings

(56) References Cited

U.S. PATENT DOCUMENTS

| | | | | |
|---|---|---|---|---|
| 2015/0218169 A1* | 8/2015 | Barr | ............... | C07D 401/12 514/210.18 |
| 2015/0297566 A1* | 10/2015 | Karstens | ............ | C07D 231/56 514/303 |

FOREIGN PATENT DOCUMENTS

| | | | |
|---|---|---|---|
| WO | WO-2006/063167 A1 | 6/2006 | |
| WO | WO-2011/014775 A1 | 2/2011 | |
| WO | WO-2012/106995 A1 | 8/2012 | |
| WO | WO2012176763 | * | 12/2012 |

OTHER PUBLICATIONS

Huh; Eur. J. Immunol. 2012, 42, 2232-2237.*
Solt; Trends in Endocrinology and Metabolism 2012, 23, 619-627.*
Annunziato et al., "Type 17 T helper cells—origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Bundgaard (ed ), Design of Prodrugs, Elsevier (1985).
Buonocore etal., "Innate lymphoid cells drive interleukin-23-dependent innate intestinal pathology," 464 Nature 1371-75 (2010).
Eberl et al., "An essential function for the nuclear receptor RORγ t in the generation of fetal lymphoid tissue inducer cells," 5(1) Nat. Immunol. 64-73 (2004).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
He et al., "RORγ t, a Novel Isoform of an Orphan Receptor, Negatively Regulates Fas Ligand Expression and IL-2 Production in T Cells," 9 Immunity 797-806 (1998).
Higuchi et al. (eds.), Pro-drugs as Novel Delivery Systems, 14 A.C.S. Symposium Series (1975).
Hirose et al.,"RORγ : the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγ t Directs the Differentiation Program of roinflammatory IL-17+ T Helper Cells," 126 Cell 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphan Nuclear Receptor RORγ ," 24(5) Mol. Endocrinol. 923-29 (2010).
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor ROR γ ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009.

Roche (ed.), Bioreversible Carriers in Drug Design, Pergamon Press (1987).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et aL, "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Xie et al.,"RORγ t Recruits Steroid Receptor Coactivators to Ensure Thymocyte Survival," 175(6) J. Immunol. 3800-09 (2005).
Yang et al., "T Helper 17 Lineage Differentiation is Programmed by Orphan Nuclear Receptors RORα and RORγ ," 28 Immunity 29-39 (2008).
Zhou et al., "Use of Homogeneous Time-Resolved Fluorescence Energy Transfer in the Measurement of Nuclear Receptor Activation," 25 Methods 54-61 (2001).
PCT International Search Report (PCT Article 18 and Rules 43 and 44) for PCT/US2013/054902, Feb. 28, 2014.
PCT Written Opinion of the International Searching Authority (PCT Rule 43bis.1) for PCT/US2013/054902, Feb. 28, 2014.
Cai, et al., "Pivotal Role of Dermal IL-17-Producing γδ T Cells in Skin Inflammation", Immunity (2011) vol. 35, pp. 596-610.
Dr. Baeton, et al., "Secukinumab, an Interleukin-17A Inhibitor, in Ankylosing Spondylitis", The New England Journal of Medicine, (2015) vol. 373, pp. 2534-2548.
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10/1002/art, American College of Rheumatology, (2016) pp. 1-27.
Krueger, "A welcome surprise in psoriasis", Nature Medicine, (2012) vol. 18, No. 12, pp. 1750-1751.
Leonardi, et al., "Anti-Interleukin-17 Monoclonal Antibody lxekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Nakajima, et al., "IL-17A as an Inducer for Th2 Immune Responses in Murine Atopic Dermatitis Models", Journal of Investigative Dermatology, (2014) vol. 134, pp. 2122-2130.
Papp, et al. "Brodalumab, an Anti-Interleukin-17-Receptor Antibody for Psoriasis", The New England Journal of Medicine, (2012) vol. 366, Iss. 13, 9 pgs.
Skepner, et al., "Pharmacologic Inhibition of RORγt RegulatesTh17 Signature Gene Expression and Suppresses Cutaneous Inflammation in Vivo", The Journal of Immunology, (2014) pp. 1-12.
Smith, "The Bench-to-Bedside Story of IL-17 and the Therapeutic Efficacy of its Targeting in Spondyloarthritis", Curr Rheumatol Rep. (2016) vol. 18, pp. 1-10.
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Xiao, et al., "Small-Molecule RORγt Antagonists Inhibit T Helper 17 Cell Transcriptional Network by Divergent Mechanisms", Immunity (2014) vol. 40, pp. 477-489.

* cited by examiner

3-CYCLOHEXENYL AND CYCLOHEXYL SUBSTITUTED INDOLE AND INDAZOLE COMPOUNDS AS RORGAMMAT INHIBITORS AND USES THEREOF

CROSS REFERENCE TO RELATED APPLICATIONS

This application is a national stage of International (PCT) Patent Application Serial No. PCT/US2013/054902, filed Aug. 14, 2013, which claims the benefit of and priority to Patent Application Serial No. PCT/CN2012/080133, filed Aug. 15, 2012.

BACKGROUND OF THE INVENTION

Upon activation by antigen-presenting cells naïve T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver and muscle), exclusively expressed in cells of the lymphoid lineage and embryonic lymphoid tissue inducers (Sun et al., *Science* 288: 2369-2372, 2000; Eberl et al., *Nat Immunol.* 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004) and gamma-delta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., *J. Allergy Clin. Immunol.* 123: 1004-1011, 2009; Annuziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-62, 2010). Another example includes infectious diseases, such as but not limited to mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immue disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

SUMMARY OF THE INVENTION

Accordingly, a need exists for improved treatments for immune disorders and inflammatory disorders. The present invention addresses this need and provides other related advantages.

The present invention provides compounds that alter the interaction of coregulator proteins with RORgammaT, and thereby antagonize RORgammaT-mediated transcriptional activity, their use for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

The present invention provides a compound according to Formula I

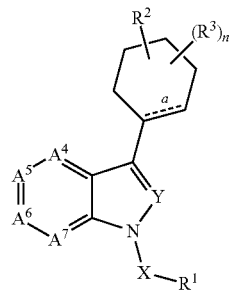

or a pharmaceutically acceptable salt or solvate thereof, wherein:
a is a bond or no bond;
X is $CH_2$, C(O), $CR^b$;
Y is CH, N, $CR^a$;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than two of $A^4$-$A^7$ can be N;
$R^a$ is $(C_{1-4})$alkyl;
$R^b$ is $(C_{1-4})$alkyl;
$R^1$ is
  (i) $(C_{3-12})$carbocyclyl; or
  (ii) a 4- to 12-membered heterocyclyl,
  both (i) and (ii) optionally substituted with one, two, three, four or five $R^8$;
$R^2$ is hydroxycarbonyl, hydroxycarbonyl$(C_{1-10})$alkyl, $(C_{1-10})$alkylsulfoxyaminocarbonyl, or carbamoyl;
$R^3$ is hydrogen, halogen, cyano, nitro, hydroxy, $(C_{1-3})$alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;
$R^4$-$R^7$ independently are H, halogen, amino, cyano, hydroxy, $(C_{1-3})$alkoxy, $(C_{1-4})$alkyl, $(C_{0-10})$alkyl)aminocarbonyl, (di)$(C_{1-6})$alkylaminocarbonyl or amino$(C_{1-4})$alkyl, wherein $(C_{1-3})$alkoxy, $(C_{1-4})$alkyl, $(C_{0-10})$alkyl)aminocarbonyl, (di)$(C_{1-6})$alkylaminocarbonyl and amino$(C_{1-4})$alkyl are optionally substituted with one or more halogen, hydroxyl or $(C_{1-3})$alkoxy; or a group having the formula

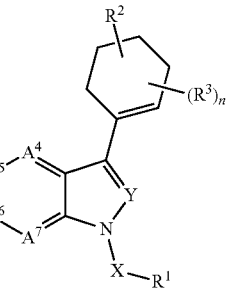

optionally substituted with one or more of the following: $(C_{1-10})$alkyl, halogen, amino, cyano, hydroxy, $(C_{1-3})$alkoxy, and wherein m is 1, 2, 3, or 4;
$R^8$ is halogen, cyano, amino, nitro, hydroxy, $H_2NC(O)$—, $(C_{1-3})$alkoxycarbonyl, (di)$(C_{1-6})$alkylaminocarbonyl, $(C_{1-4})$alkyl, $(C_{3-7})$cycloalkyl, $(C_{3-5})$heterocycloalkyl, (C1-3)alkoxyaminocarbonyl, 4- to 8-membered heterocyclylcarbonyl, (C3-6)cycloalkylaminocarbonyl, amino(C1-4)alkyloxycarbonyl or $(C_{1-3})$alkoxy, wherein $(C_{1-3})$alkoxycarbonyl, (di)$(C_{1-6})$alkylaminocarbonyl, $(C_{1-4})$alkyl, $(C_{1-3})$alkoxyaminocarbonyl, 4- to 8-membered heterocyclylcarbonyl, $(C_{3-6})$cycloalkylaminocarbonyl, amino$(C_{1-4})$alkyloxycarbonyl and $(C_{1-3})$alkoxy are optionally substituted with oxo, $(C_{1-4})$alkyl, hydroxy$(C_{1-3})$alkyl, or one, two or three halogens.

In a first embodiment of the compound having Formula I is a compound having Formula Ix

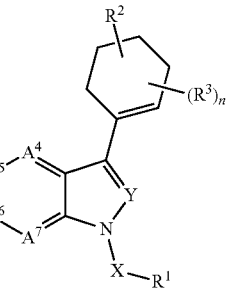

Ix or a pharmaceutically acceptable salt or solvate thereof, wherein:
X is $CH_2$, C(O), $CR^b$;
Y is CH, N, $CR^a$;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than two of $A^4$-$A^7$ can be N;
$R^a$ is $(C_{1-4})$alkyl;
$R^b$ is $(C_{1-4})$alkyl;
$R^1$ is
  (i) $(C_{3-12})$carbocyclyl; or
  (ii) a 4- to 12-membered heterocyclyl,
  both (i) and (ii) optionally substituted with one, two, three, four or five $R^8$;
$R^2$ is hydroxycarbonyl, hydroxycarbonyl$(C_{1-10})$alkyl, $(C_{1-10})$alkylsulfoxyaminocarbonyl, or carbamoyl;
$R^3$ is hydrogen, halogen, cyano, nitro, hydroxy, $(C_{1-3})$alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;

$R^4$-$R^7$ independently are H, halogen, amino, cyano, hydroxy, $(C_{1-3})$alkoxy, $(C_{1-4})$alkyl, $(C_{0-10})$alkyl)aminocarbonyl, (di)$(C_{1-6})$alkylaminocarbonyl or amino$(C_{1-4})$alkyl, wherein $(C_{1-3})$alkoxy, $(C_{1-4})$alkyl, $(C_{0-10})$alkyl)aminocarbonyl, (di)$(C_{1-6})$alkylaminocarbonyl and amino$(C_{1-4})$alkyl are optionally substituted with one or more halogen, hydroxyl or $(C_{1-3})$alkoxy; or a group having the formula

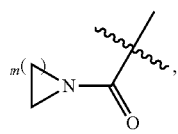

optionally substituted with one or more of the following: $(C_{1-10})$alkyl, halogen, amino, cyano, hydroxy, $(C_{1-3})$alkoxy, and wherein m is 1, 2, 3, or 4; $R^8$ is halogen, cyano, amino, nitro, hydroxy, $H_2NC(O)$—, $(C_{1-3})$alkoxycarbonyl, (di)$(C_{1-6})$alkylaminocarbonyl, $(C_{1-4})$alkyl, $(C_{3-7})$cycloalkyl, $(C_{3-5})$heterocycloalkyl, $(C_{1-3})$alkoxyaminocarbonyl, 4- to 8-membered heterocyclylcarbonyl, $(C_{3-6})$cycloalkylaminocarbonyl, amino$(C_{1-4})$alkyloxycarbonyl or $(C_{1-3})$alkoxy, wherein $(C_{1-3})$alkoxycarbonyl, (di)$(C_{1-6})$alkylaminocarbonyl, $(C_{1-4})$alkyl, (C1-3)alkoxyaminocarbonyl, 4- to 8-membered heterocyclylcarbonyl, $(C_{3-6})$cycloalkylaminocarbonyl, amino$(C_{1-4})$alkyloxycarbonyl and $(C_{1-3})$alkoxy are optionally substituted with oxo, $(C_{1-4})$alkyl, hydroxy$(C_{1-3})$alkyl, or one, two or three halogens.

In a second embodiment of the compound having Formula I is a compound having Formula Ia

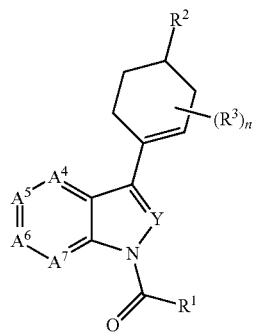

Ia and a pharmaceutically acceptable salt or solvate thereof.

In a third embodiment of the compound having Formula I is a compound having Formula Ib

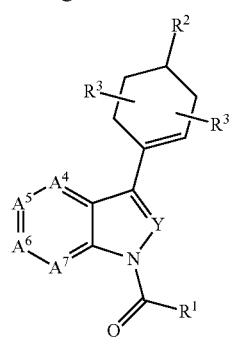

Ib and a pharmaceutically acceptable salt or solvate thereof.

In a first subset of the third embodiment is a compound wherein Y is N.

In a second subset of the third embodiment is a compound having Formula Ic

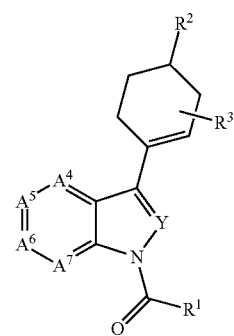

Ic and a pharmaceutically acceptable salt or solvate thereof.

In a second subset of the first embodiment is a compound having Formula Id

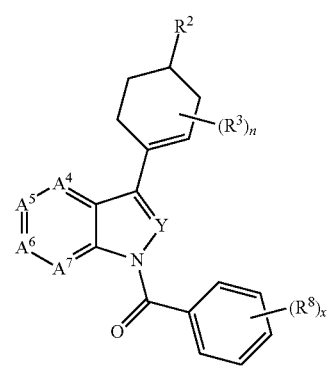

Id wherein x is 1, 2, 3, 4 or 5, and a pharmaceutically acceptable salt or solvate thereof.

In a subset of the compound having Formula Id is a compound having Formula Ie

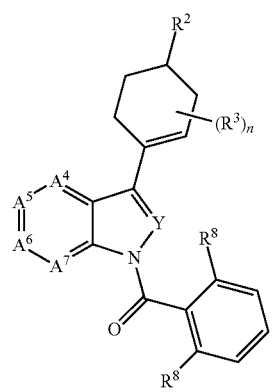

Ie and a pharmaceutically acceptable salt or solvate thereof.

In a subset of the compound having Formula Ie is a compound having Formula If

If

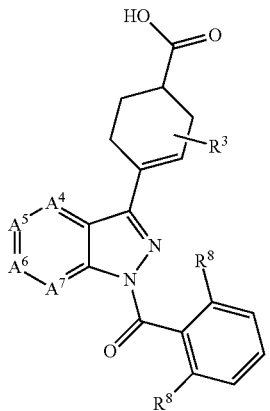

and a pharmaceutically acceptable salt or solvate thereof.

In a subset of the compound having Formula If is a compound having Formula Ig

Ig

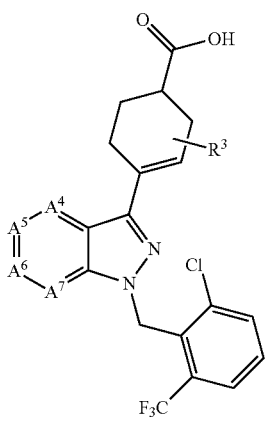

and a pharmaceutically acceptable salt or solvate thereof.

In a third subset of the first embodiment is a compound wherein $A^4, A^5, A^6, A^7$ are selected from the group consisting of: (i) $CR^4, CR^5, CR^6, CR^7$; (ii) N, $CR^5, CR^6, CR^7$; (iii) $CR^4$, N, $CR^6, CR^7$; (iv) $CR^4, CR^5$, N, $CR^7$; (v) $CR^4, CR^5, CR^6$, N; (vi) N, N, $CR^6, CR^7$; (vii) $CR^4$, N, N, $CR^7$; (viii) $CR^4, CR^5$, N, N; (ix) N, $CR^5$, N, $CR^7$; (x) $CR^4$, N, $CR^6$, N; and (xi) N, $CR^5, CR^6$, N.

In a fourth subset of the first embodiment is a compound wherein $A^4, A^5, A^6, A^7$ is (i) $CR^4, CR^5, CR^6, CR^7$; or (ii) N, $CR^5, CR^6, CR^7$; and Y is N.

In a fifth subset of the first embodiment is compound wherein $R^1$ is (i) $(C_{3-7})$cycloalkyl or $(C_{3-5})$heterocycloalkyl, both optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one or more halogens; (ii) $(C_{2-9})$heteroaryl, optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one or more halogens; or (iii) $(C_{6-14})$aryl, optionally substituted with one or more $R^8$, wherein $R^8$ is selected from halogen, amino, cyano, nitro, hydroxy, $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl or $(C_{1-3})$alkoxy are optionally substituted with one or more halogens.

In a sixth subset of the first embodiment is compound wherein $R^1$ is $(C_{2-9})$heteroaryl, or (ii) $(C_{6-14})$aryl, optionally substituted with one, two, three, four or five $R^8$. In a further subset $R^8$ is selected from halogen, amino, cyano, nitro, hydroxy, $(C_{1-3})$alkoxycarbonyl, $(C_{1-4})$alkyl, $(C_{1-3})$alkoxy, wherein $(C_{1-3})$alkoxycarbonyl, $(C_{1-4})$alkyl and $(C_{1-3})$alkoxy are optionally substituted with one or more halogens.

In a seventh subset of the first embodiment, $R^1$ is $(C_{6-14})$aryl, optionally substituted with one, two, three, four or five $R^8$. In a further subset $R^8$ is selected from halogen, cyano, $(C_{1-3})$-alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one, two or three halogens.

In an eighth subset of the first embodiment, $R^1$ is phenyl, naphthyl, pyridinyl, quinolinyl, benzooxadiazolyl, thiophenyl, isoxazolyl, or benzothiophenyl, each optionally substituted with one or more $R^8$. In a further subset $R^8$ is selected from halogen, amino, cyano, nitro, hydroxy, $(C_{1-3})$alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one or more halogens.

In a ninth subset of the first embodiment, $R^1$ is phenyl, optionally substituted with one, two or three $R^8$. In a further subset $R^8$ is selected from halogen, amino, cyano, nitro, hydroxy, $(C_{1-3})$alkoxycarbonyl, $(C_{1-4})$alkyl or $(C_{1-3})$alkoxy, wherein $(C_{1-3})$alkoxycarbonyl, $(C_{1-4})$alkyl and $(C_{1-3})$alkoxy are optionally substituted with one or more halogens.

In a tenth subset of the first embodiment, $R^2$ is C(O)OH.

A still further embodiment of the compounds of Formula I, Ix, Ia, Ib, Ic, Id, Ie, If or Ig are compounds wherein one of $R^4$, $R^5$, $R^6$, and $R^7$ is other than hydrogen.

The invention also relates to those compounds wherein all specific definitions for $A^1, A^2, A^3, A^4, R^1, R^2, R^3, R^4, R^5, R^6, R^7, R^8, R^a, R^b$, Y, m, n and x and all substituent groups in the various aspects of the inventions defined hereinabove occur in any combination within the definition of the compound of Formula I.

Non-limiting examples of the compound of the present invention include:

4-(1-(2-chloro-6-(trifluoromethyl)benzoyl)-6-(dimethylcarbamoyl)-1H-indazol-3-yl)cyclohex-3-enecarboxylic acid;

4-(1-(2-chloro-6-(trifluoromethyl)benzoyl)-4-fluoro-1H-indazol-3-yl)cyclohex-3-enecarboxylic acid;

4-(1-(2-chloro-6-(trifluoromethyl)benzoyl)-4-fluoro-1H-indazol-3-yl)cyclohex-3-enecarboxylic acid fluorobenzoic acid;

4-(1-(2-chloro-6-(trifluoromethyl)benzoyl)-6-(2-hydroxyethylcarbamoyl)-1H-indazol-3-yl)cyclohex-3-enecarboxylic acid;

4-(1-(2-chloro-6-(trifluoromethyl)benzoyl)-1H-pyrazolo[4,3-b]pyridin-3-yl)cyclohex-3-enecarboxylic acid;

4-(1-(2-chloro-6-(trifluoromethyl)benzoyl)-1H-pyrazolo[4,3-b]pyridin-3-yl)-1-methylcyclohex-3-enecarboxylic acid;

4-(1-(2-chloro-6-(trifluoromethyl)benzoyl)-1H-pyrazolo[4,3-b]pyridin-3-yl)-2-methylcyclohex-3-enecarboxylic acid;

4-(1-(2-chloro-6-(trifluoromethyl)benzoyl)-1H-indazol-3-yl)cyclohex-3-enecarboxylic acid;

4-(4-chloro-1-(2-chloro-6-(trifluoromethyl)benzoyl)-1H-indazol-3-yl)-1-methylcyclohex-3-enecarboxylic acid;
4-(1-(2-chloro-6-cyclopropylbenzoyl)-4-fluoro-1H-indazol-3-yl)-1-methylcyclohex-3-enecarboxylic acid;
4-(1-(2-chloro-6-methylbenzoyl)-4-fluoro-1H-indazol-3-yl)cyclo-hex-3-enecarboxylic acid;
4-(1-(2-chloro-6-methylbenzoyl)-1H-pyrazolo[4,3-b]pyridine-3-yl)cyclohex-3-enecarboxylic acid;
(R or S)-4-(1-(2-chloro-6-cyclopropylbenzoyl)-6-(3-methoxy azetidine-1-carbonyl)-1H-indazol-3-yl)cyclohex-3-enecarboxylic acid;
(S or R)-4-(1-(2-chloro-6-cyclopropylbenzoyl)-6-(3-methoxy azetidine-1-carbonyl)-1H-indazol-3-yl)cyclohex-3-enecarboxylic acid;
(R or S)-4-(1-(2-chloro-6-cyclopropylbenzoyl)-6-(3-methoxyazetidine-1-carbonyl)-1H-indazol-3-yl)-1-methylcyclohex-3-enecarboxylic acid;
(S or R)-4-(1-(2-chloro-6-cyclopropylbenzoyl)-6-(3-methoxyazetidine-1-carbonyl)-1H-indazol-3-yl)-1-methylcyclohex-3-enecarboxylic acid;
(R or S)-4-(1-(2-chloro-6-cyclopropylbenzoyl)-4-fluoro-1H-indazol-3-yl)cyclohex-3-enecarboxylic acid;
(S or R)-4-(1-(2-chloro-6-cyclopropylbenzoyl)-4-fluoro-1H-indazol-3-yl)cyclohex-3-enecarboxylic acid;
4-(1-(2-chloro-6-(trifluoromethyl)benzoyl)-6-(3,3-difluoroazetidine-1-carbonyl)-1H-indazol-3-yl)cyclohex-3-enecarboxylic acid;
4-(1-(2-chloro-6-(trifluoromethyl)benzoyl)-6-(cyclopropylcarbamoyl)-1H-indazol-3-yl)cyclohex-3-enecarboxylic acid;
4-(1-(2-chloro-6-(trifluoromethyl)benzoyl)-6-(cyclopropyl(methyl)carbamoyl)-1H-indazol-3-yl)cyclohex-3-enecarboxylic acid;
4-(6-(azetidine-1-carbonyl)-1-(2-chloro-6-(trifluoromethyl)benzoyl)-1H-indazol-3-yl)cyclohex-3-enecarboxylic acid;
4-(1-(2-chloro-6-(trifluoromethyl)benzoyl)-6-(3-methoxyazetidine-1-carbonyl)-1H-indazol-3-yl)cyclohex-3-enecarboxylic acid;
4-(1-(2-chloro-6-(trifluoromethyl)benzoyl)-6-(pyrrolidine-1-carbonyl)-1H-indazol-3-yl)cyclohex-3-enecarboxylic acid;
4-(1-(2-chloro-6-(trifluoromethyl)benzoyl)-6-((S)-2-methylpyrrolidine-1-carbonyl)-1H-indazol-3-yl)cyclohex-3-enecarboxylic acid;
4-(1-(2-chloro-6-(trifluoromethyl)benzoyl)-6-((R)-2-methylpyrrolidine-1-carbonyl)-1H-indazol-3-yl)cyclohex-3-enecarboxylic acid;
4-(1-(2-chloro-6-(trifluoromethyl)benzoyl)-6-(3-methoxypyrrolidine-1-carbonyl)-1H-indazol-3-yl)cyclohex-3-enecarboxylic acid;
4-(1-(2-chloro-6-(trifluoromethyl)benzoyl)-6-(2-methylmorpholine-4-carbonyl)-1H-indazol-3-yl)cyclohex-3-enecarboxylic acid;
4-(1-(2-chloro-6-(trifluoromethyl)benzoyl)-6-(cyclohexyl(methyl)carbamoyl)-1H-indazol-3-yl)cyclohex-3-enecarboxylic acid;
4-(1-(2-chloro-6-(trifluoromethyl)benzoyl)-6-(morpholine-4-carbonyl)-1H-indazol-3-yl)cyclohex-3-enecarboxylic acid;
4-(1-(2-chloro-6-(trifluoromethyl)benzoyl)-6-((2R,6S)-2,6-dimethylmorpholine-4-carbonyl)-1H-indazol-3-yl)cyclohex-3-enecarboxylic acid;
4-(1-(2-chloro-6-(trifluoromethyl)benzoyl)-6-(4-methyl-3-oxopiperazine-1-carbonyl)-1H-indazol-3-yl)cyclohex-3-enecarboxylic acid;
4-(1-(2-chloro-6-(trifluoromethyl)benzoyl)-6-((S)-3-methylmorpholine-4-carbonyl)-1H-indazol-3-yl)cyclohex-3-enecarboxylic acid;
4-(1-(2-chloro-6-(trifluoromethyl)benzoyl)-6-(methyl(tetrahydro-2H-pyran-4-yl)carbamoyl)-1H-indazol-3-yl)cyclohex-3-enecarboxylic acid;
4-(1-(2-chloro-6-(trifluoromethyl)benzoyl)-6-((R)-3-methylmorpholine-4-carbonyl)-1H-indazol-3-yl)cyclohex-3-enecarboxylic acid;
4-(1-(2-chloro-6-(trifluoromethyl)benzoyl)-6-((S)-2-methylmorpholine-4-carbonyl)-1H-indazol-3-yl)cyclohex-3-enecarboxylic acid;
4-(1-(2-chloro-6-(trifluoromethyl)benzoyl)-6-((2-hydroxyethyl)(methyl)carbamoyl)-1H-indazol-3-yl)cyclohex-3-enecarboxylic acid;
4-(1-(2-chloro-6-(trifluoromethyl)benzoyl)-6-(isopropylcarbamoyl)-1H-indazol-3-yl)cyclohex-3-enecarboxylic acid;
4-(1-(2-chloro-6-(trifluoromethyl)benzoyl)-6-(isopropyl(methyl)carbamoyl)-1H-indazol-3-yl)cyclohex-3-enecarboxylic acid;
4-(1-(2-chloro-6-(trifluoromethyl)benzoyl)-6-((2-methoxyethyl)(methyl)carbamoyl)-1H-indazol-3-yl)cyclohex-3-enecarboxylic acid;
4-(1-(2-chloro-6-(trifluoromethyl)benzoyl)-6-(3-hydroxyazetidine-1-carbonyl)-1H-indazol-3-yl)cyclohex-3-enecarboxylic acid;
4-(1-(2-chloro-6-(trifluoromethyl)benzoyl)-6-(3-fluoroazetidine-1-carbonyl)-1H-indazol-3-yl)cyclohex-3-enecarboxylic acid;
4-(1-(2-chloro-6-(trifluoromethyl)benzoyl)-6-(piperidine-1-carbonyl)-1H-indazol-3-yl)cyclohex-3-enecarboxylic acid;
4-(1-(2-chloro-6-(trifluoromethyl)benzoyl)-6-(((1-hydroxy-3-(methylamino)propan-2-yl)oxy)carbonyl)-1H-indazol-3-yl)cyclohex-3-enecarboxylic acid;
4-(1-(2-chloro-6-(trifluoromethyl)benzoyl)-6-((S)-3-methoxypyrrolidine-1-carbonyl)-1H-indazol-3-yl)cyclohex-3-enecarboxylic acid;
4-(1-(2-chloro-6-(trifluoromethyl)benzoyl)-6-((R)-3-methoxypyrrolidine-1-carbonyl)-1H-indazol-3-yl)cyclohex-3-enecarboxylic acid;
4-(1-(2-chloro-6-(trifluoromethyl)benzoyl)-4-fluoro-1H-indol-3-yl)cyclohex-3-enecarboxylic acid;
4-(1-(2-chloro-6-(trifluoromethyl)benzoyl)-4-fluoro-1H-indazol-3-yl)-2-hydroxycyclohex-3-enecarboxylic acid;
4-(1-(2-chloro-6-(trifluoromethyl)benzoyl)-4-fluoro-1H-indazol-3-yl)-6-hydroxycyclohex-3-enecarboxylic acid;
4-(1-(2-chloro-6-(trifluoromethyl)benzoyl)-4-fluoro-1H-indazol-3-yl)-2-hydroxy-6-methylcyclohex-3-enecarboxylic acid;
4-(1-(2-chloro-6-(trifluoromethyl)benzoyl)-4-fluoro-1H-indazol-3-yl)-4-methylcyclohexanecarboxylic acid;
(trans)-4-(1-(2-chloro-6-(trifluoromethyl)benzoyl)-4-fluoro-1H-indazol-3-yl)-4-methyl cyclohexanecarboxylic acid;
(cis)-4-(1-(2-chloro-6-(trifluoromethyl)benzoyl)-4-fluoro-1H-indazol-3-yl)-4-methylcyclohexanecarboxylic acid;
(trans)-4-(1-(2-chloro-6-(trifluoromethyl)benzoyl)-4-fluoro-1H-indazol-3-yl)cyclohexanecarboxylic acid;
(cis)-4-(1-(2-chloro-6-(trifluoromethyl)benzoyl)-4-fluoro-1H-indazol-3-yl)cyclohexanecarboxylic acid;
(trans)-4-(1-(2-chloro-6-(trifluoromethyl)benzoyl)-4-fluoro-1H-indazol-3-yl)-1-methylcyclohexanecarboxylic acid;
(cis)-4-(1-(2-chloro-6-(trifluoromethyl)benzoyl)-4-fluoro-1H-indazol-3-yl)-1-methylcyclohexanecarboxylic acid;

(R and S)-4-(1-(2-chloro-6-(trifluoro methyl)benzoyl)-4-fluoro-1H-indazol-3-yl)-2,2-dimethylcyclohex-3-enecarboxylic acid;

(R and S) 4-(1-(2-chloro-6-(trifluoromethyl)benzoyl)-4-fluoro-1H-indazol-3-yl)-6,6-dimethylcyclohex-3-enecarboxylic acid;

(trans)-4-(1-(2-chloro-6-(trifluoromethyl)benzoyl)-1H-pyrazolo[4,3-b]pyridin-3-yl)cyclohexanecarboxylic acid;

(cis)-4-(1-(2-chloro-6-(trifluoromethyl)benzoyl)-1H-pyrazolo[4,3-b]pyridin-3-yl)cyclohexanecarboxylic acid;

4-(1-(2-chloro-6-(trifluoromethyl)benzoyl)-4-fluoro-1H-indazol-3-yl)-5-methylcyclohex-3-enecarboxylic acid; and 4-(1-(2-chloro-6-(trifluoromethyl)benzoyl)-4-fluoro-1H-indazol-3-yl)-4-hydroxycyclohexanecarboxylic acid.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—$CH(CH_3)$—$CH_2$—B, A-$CH_2$—$CH(CH_2CH_3)$—B, A-$CH_2$—$C(CH_3)(CH_3)$—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, ($C_{3-7}$)cycloalkyl, ($C_{3-5}$)heterocycloalkyl, $C_2$-$C_6$ alkenyl, $C_2$-$C_6$ alkynyl, ($C_0$-$C_6$ alkyl) $S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, $H_2N$—C(O)(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl) OC(O)NH—, —NH($C_1$-$C_6$ alkyl)NHC(O)NH($C_1$-$C_6$ alkyl), NHC(O)OC$_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom that results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

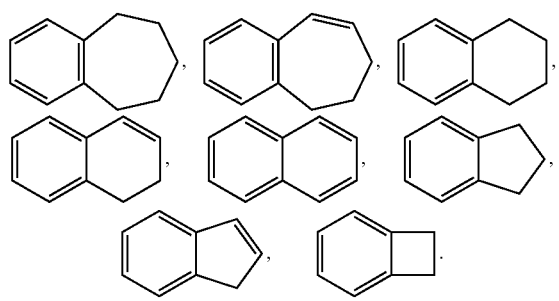

Aromatic carbocycles form another subset of the carbocycles. The term "aryl" refers to aromatic mono- and polycarbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system that consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and that consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl, isoquinolinyl, naphthyridinyl, pyrazolo[3,4-b]pyridine, imidazo[2,1-b](1,3)thiazole,

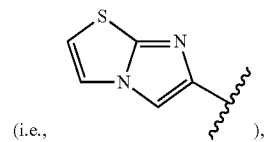

(i.e., ), 6-(1-pyrrolyl)-3-pyridyl, 4-(1-pyrrolyl)phenyl, 4-(pyrid-3-yl)phenyl, 4-(pyrid-4-yl)phenyl, and benzothiophenyl

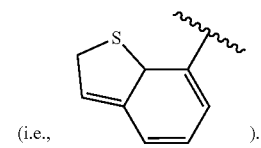 [SMILES: *C1=CC=CC2=CCSC12]

(i.e., ).

Another subset of heterocycles is unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl

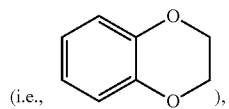

(i.e., ), and benzo-1,3-dioxolyl

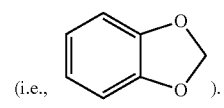

(i.e., ).

In certain contexts herein,

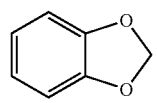

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, heterocloalkyl, aryl (including phenyl) and heteroaryl groups are unsubstituted or substituted (also referred to as "optionally substituted"). Unless the substituents are specifically provided, substituents for substituted or optionally substituted cycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halogen (or halo), $C_1$-$C_6$ alkyl optionally substituted with one to five fluorine, $NH_2$, $N(C_1$-$C_6$ alkyl$)_2$, $NO_2$, oxo, CN, $N_3$, —OH, —O($C_1$-$C_6$ alkyl) optionally substituted with one to five fluorine, $C_3$-$C_{10}$ cycloalkyl, $(C_{3-7})$cycloalkyl, $(C_{3-5})$heterocycloalkyl, $C_2$-$C_6$ alkenyl, $C_2$-$C_6$ alkynyl, $(C_0$-$C_6$ alkyl)S(O)$_{0-2}$—, aryl-S(O)$_{0-2}$—, $(C_0$-$C_6$ alkyl)S(O)$_{0-2}$($C_0$-$C_6$ alkylene)-, $(C_0$-$C_6$ alkyl)C(O)NH—, $H_2$N—C(NH)—, $(C_0$-$C_6$ alkyl)C(O)—, $(C_0$-$C_6$ alkyl)OC(O)—, $(C_0$-$C_6$alkyl)O($C_1$-$C_6$ alkylene)-, $(C_0$-$C_6$ alkyl)C(O)$_{1-2}$($C_0$-$C_6$ alkylene)-, $(C_0$-$C_6$ alkyl)$_2$NC(O)—, $(C_0$-$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom.

The terms "aralkyl" and "heteroaralkyl" refer to an aryl/heteroaryl linked to the rest of the molecule via a $C_1$ to $C_4$ alkylene.

The term "$C_0$" as employed in expressions such as "$C_{0-6}$ alkylene" means a direct covalent bond; or when employed in expressions such as "$C_{0-6}$ alkyl" means hydrogen.

Similarly, when an integer defining the presence of a certain number of atoms in a group is equal to zero, it means that the atoms adjacent thereto are connected directly by a bond; for example, in the structure

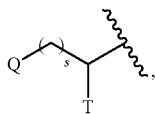

wherein s is an integer equal to zero, 1 or 2, the structure is

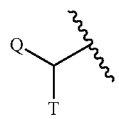

when s is zero; or it means that the indicated atom is absent; for example —S(O)$_0$— means —S—.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)$_2$ can be

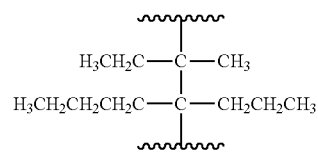

The term $(C_{1-6})$alkyl as used hereinabove means a branched or unbranched alkyl group having 1-6 carbon atoms, for example methyl, ethyl, propyl, isopropyl, butyl, tert-butyl, n-pentyl and n-hexyl. Preferred is $(C_{1-4})$alkyl.

The term $(C_{1-5})$alkyl means a branched or unbranched alkyl group having 1-5 carbon atoms, for example methyl, ethyl, propyl, isopropyl, butyl, tert-butyl and n-pentyl.

The term $(C_{1-4})$alkyl as used herein means a branched or unbranched alkyl group having 1-4 carbon atoms, being methyl, ethyl, n-propyl, isopropyl, n-butyl, isobutyl, sec-butyl and tert-butyl.

The term $(C_{1-3})$alkoxy means an alkoxy group having 1-3 carbon atoms, the alkyl moiety being branched or unbranched.

The term $(C_{1-3})$alkoxycarbonyl means an alkoxycarbonyl group having 1-3 carbon atoms in the alkoxy moiety, the alkoxy moiety having the same meaning as previously defined.

The term (di)$(C_{1-6})$alkylaminocarbonyl means an alkylaminocarbonyl group, the amino group of which is mono-substituted or disubstituted independently with an alkyl group which contains 1-6 carbon atoms and which has the same meaning as previously defined. Preferred alkyl group is $(C_{1-4})$alkyl.

The term $(C_{1-3})$alkoxyaminocarbonyl means an alkoxyaminocarbonyl group, the amino group of which is substituted with an alkoxy group which contains 1-3 carbon atoms and which has the same meaning as previously defined.

The term amino$(C_{1-4})$alkyloxycarbonyl means an aminoalkyloxycarbonyl group in which the alkyl group contains 1-4 carbon atoms.

The term $(C_{3-7})$cycloalkyl means a cycloalkyl group having 3-7 carbon atoms, such as cyclopropyl, cyclobutyl, cyclopentyl, cyclohexyl and cycloheptyl. 5-6 Carbon atoms are preferred.

The term $(C_{3-5})$heterocycloalkyl means a heterocycloalkyl group having 3-5 carbon atoms, including 1-3 heteroatoms selected from N, O and/or S, which may be attached via a nitrogen if feasible, or a carbon atom. Preferred number of heteroatoms is one or two. Most preferred number is one. Preferred heteroatoms are N or O. Most preferred are piperazinyl, tetrahydropyranyl, morpholinyl and pyrrolidinyl.

A group having the formula

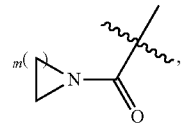

means a heterocyclocarbonyl group such as

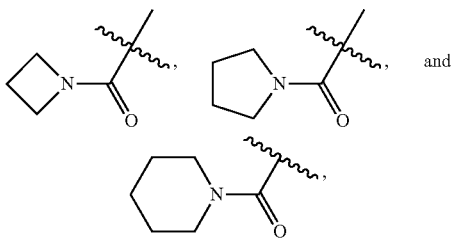

each optionally substituted with one or more $(C_{1-10})$alkyl, halogen, amino, cyano, hydroxy, and $(C_{1-3})$alkoxy.

The term $(C_{2-9})$heteroaryl means an aromatic group having 2-9 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are pyrazolyl, thiophenyl, isoxazolyl, pyridyl and quinolyl. The $(C_{2-5})$heteroaryl group may be attached via a carbon atom or a nitrogen, if feasible.

The term $(C_{6-14})$aryl means an aromatic hydrocarbon group having 6-14 carbon atoms, such as phenyl, naphthyl, tetrahydronaphthyl, indenyl, anthracyl, More preferred are $(C_{6-10})$aryl groups. The most preferred aromatic hydrocarbon group is phenyl.

As used herein, the term "$X_a$-$X_b$", shall have the same meaning as the term "$X_{a-b}$", wherein X is any atom and a and b are any integers. For example, "$C_1$-$C_4$" shall have the same meaning as "$C_{1-4}$". Additionally, when referring to a functional group generically, "$A^x$" shall have the same meaning, and be interchangeable with, "AX", wherein "A" is any atom and "x" or "X" are any integer. For example, "$R^1$" shall have the same meaning, and be interchangeable with, "R1".

In the above definitions with multifunctional groups, the attachment point is at the last group. For example, the term $(C_{1-3})$alkoxycarbonyl refers to, e.g.

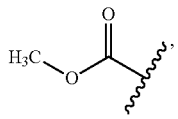

and the term (C1-4)alkylcarbonyloxy refers to, e.g.

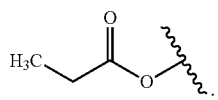

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent. Accordingly, the term "one or more" when referring to a substituent and/or variable means that one or more hydrogens on the designated atom/atoms is/are replaced with a selection from the indicated group, provided that the designated atom's normal valency under the existing circumstances is not exceeded, and that the substitution results in a stable compound.

The term "optionally substituted" means that a substitution with the specified groups, radicals, or moieties may or may not be made on the specified group.

When, in the definition of a substituent, it is indicated that "all of the alkyl groups" of said substituent are optionally substituted, this also includes the alkyl moiety of an alkoxy group.

The use of the terms "salt", "solvate", "ester", "prodrug", and the like, is intended to equally apply to the salt, solvate, ester, and prodrug of enantiomers, stereoisomers, rotamers, tautomers, positional isomers, racemates, or prodrugs of the inventive compounds.

The term "effective amount" as used herein refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee.

It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Optical Isomers—Diastereomers—Geometric Isomers—Tautomers

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formula I can form salts which are also within the scope of this invention. Reference to a compound of Formula I herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound that may not be a compound of formula I, but that converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Pro-drugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formula I, Ia, Ib, Ic, Id, Ie, If or Ig or a pharmaceutically acceptable salt or solvate thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general formula I for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general formula I can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general formula I can be used for treatment of infectious diseases in which Th17 cells and/or non-Th17 cells, which express Th17 hallmark cytokines, play a prominent role, such as but not limited to mucosal leishmaniasis.

Compounds or a pharmaceutically acceptable salt thereof having the general formula I can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

This aspect of the present invention further includes the use of a compound of Formula I, Ia, Ib, Ic, Id, Ie, If or Ig, or a pharmaceutically acceptable salt or solvate thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula I or a pharmaceutically acceptable salt or solvate thereof and one or more pharmaceutically acceptable excipients. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of formula (I) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula I, Ia, Ib, Ic, Id, Ie, If or Ig.

The invention further includes a compound of Formula I in combination with one or more other drug(s).

Methods of Synthesis

Methods for preparing the compounds of this invention are illustrated in the following schemes and examples. Other synthetic protocols will be readily apparent to those skilled in the art in light of the present disclosure. The examples illustrate the preparation of the compounds of formula I and as such are not to be considered as limiting the invention set forth in the claims appended hereto. Unless otherwise indicated, all variables are as previously defined.

All the end products of the formula I were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloro methane; Dppf: 1,1'-Bis(diphenylphosphino)ferrocene; AcOH: Acetic acid; DMAC: N,N-Dimethylacetamide; Pd(PPh$_3$)$_4$: Tetrakis(Triphenylphosphine)Palladium(0); Pd(dppf)Cl$_2$: [1,1'-Bis(diphenylphosphino) ferrocene]dichloropalladium (II); Ac$_2$O: Acetic anhydride; LiHMDS: Lithium bis(trimethylsilyl)amide; PhNTf$_2$: N-Phenyl-bis (trifluoromethanesulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether; DMAP: 4-Dimethylaminopyridine; TEA: Triethylamine; THF: Tetrahydrofuran; PYAOP: (7-Azabenzotriazol-1-yloxy)tripyrrolidinophosphonium hexafluorophosphate.

Scheme 1 illustrates a general method toward the preparation of compounds of formula I. Starting from halide A, N-acylation with either carboxylic acids or acid chloride in the presence of base led to the formation of compound B. Subsequent Suzuki coupling followed by ester hydrolysis afforded the final compound. In certain cases, ester hydrolysis occurred under the Suzuki coupling condition and led to the formation of final product within one pot.

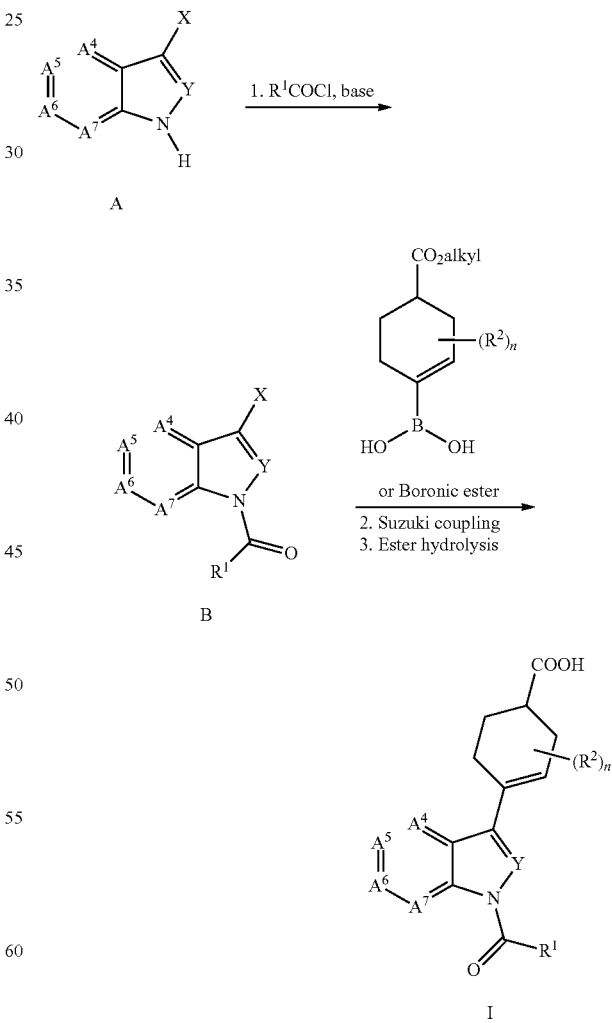

Scheme 2 illustrates a general method for the preparation of compounds of formula I that contain an amide moiety at $A^6$ position. Starting from halide A, acylation followed by ester hydrolysis gave intermediate B. Standard amide coupling furnished intermediate C. Subsequent Suzuki coupling followed by ester hydrolysis led to the formation of the final product I.

SCHEME 2

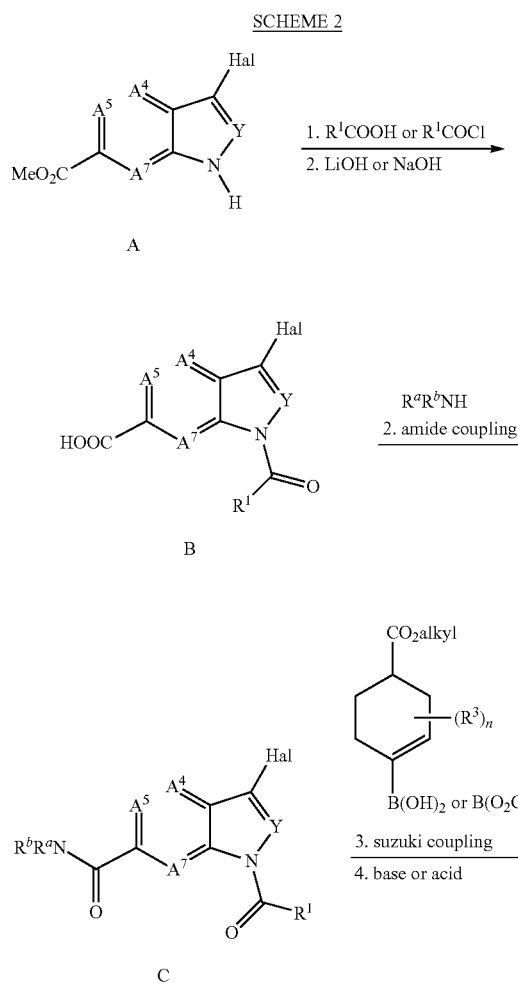

SCHEME 3

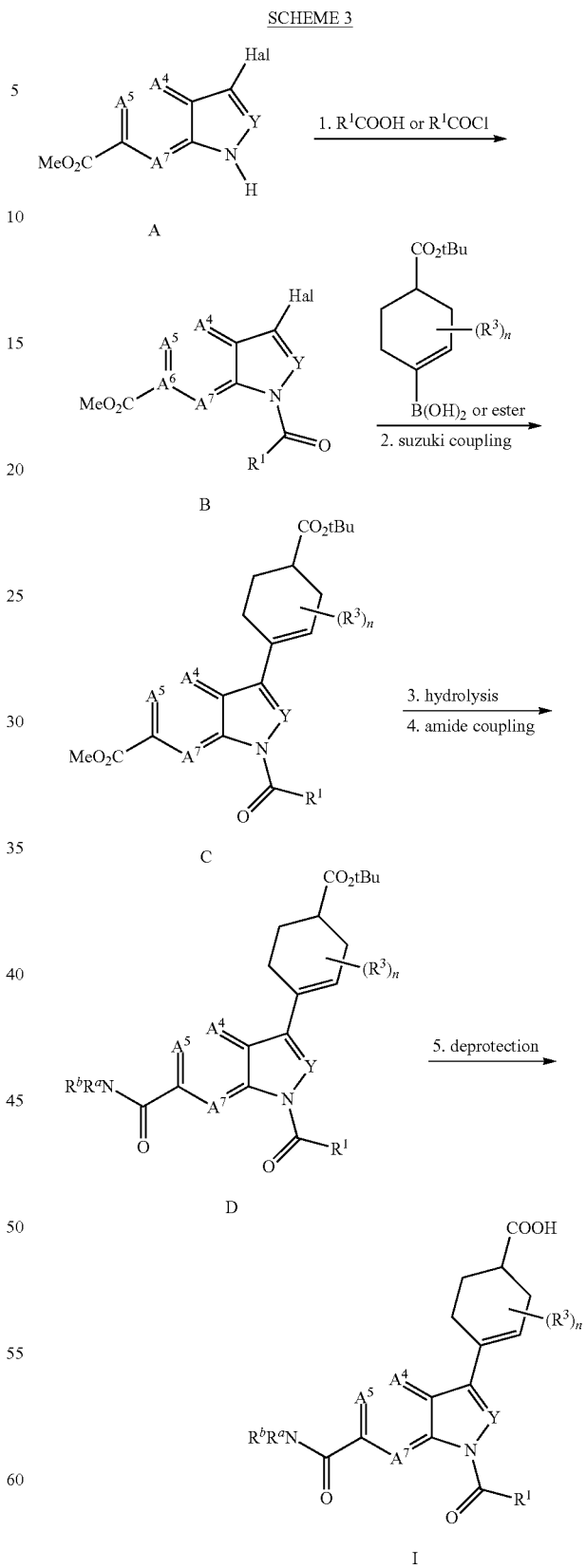

Scheme 3 illustrates an alternative method for the preparation of compounds of formula I that contain an amide moiety at $A^6$ position. Starting from halide A, N-acylation followed by Suzuki coupling gave intermediate C. Selective ester hydrolysis and subsequent amide coupling led to the formation of compound D. Final t-Bu removal under acidic conditions gave the desired product I.

Scheme 4 illustrates a general method toward the preparation of compounds of formula I that contain a cyclohexyl instead of cyclohexenyl motif. Starting from halide A, which can be obtained following those methods described previously, hydrogenation led to the formation of saturated cyclohexyl intermediate B. Ester hydrolysis gave the desired product I.

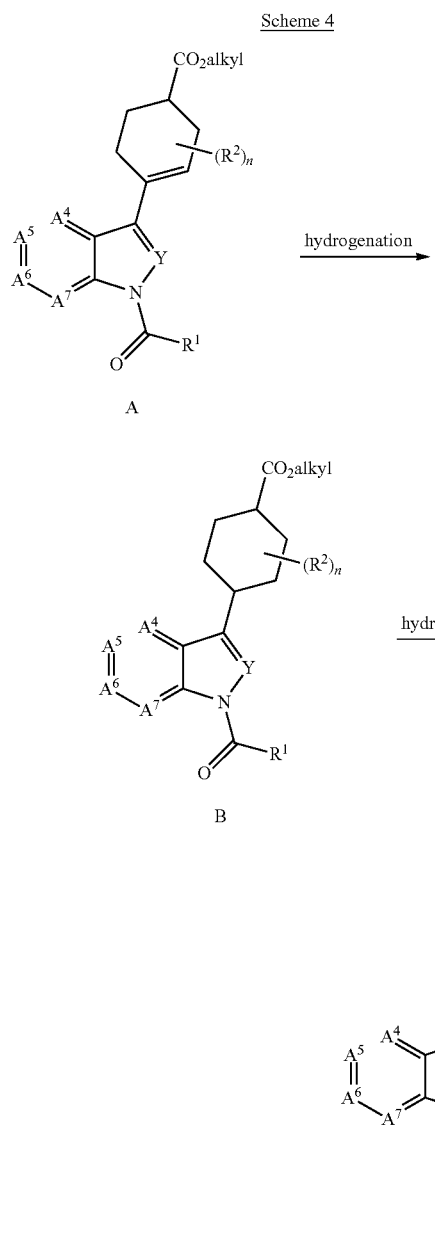

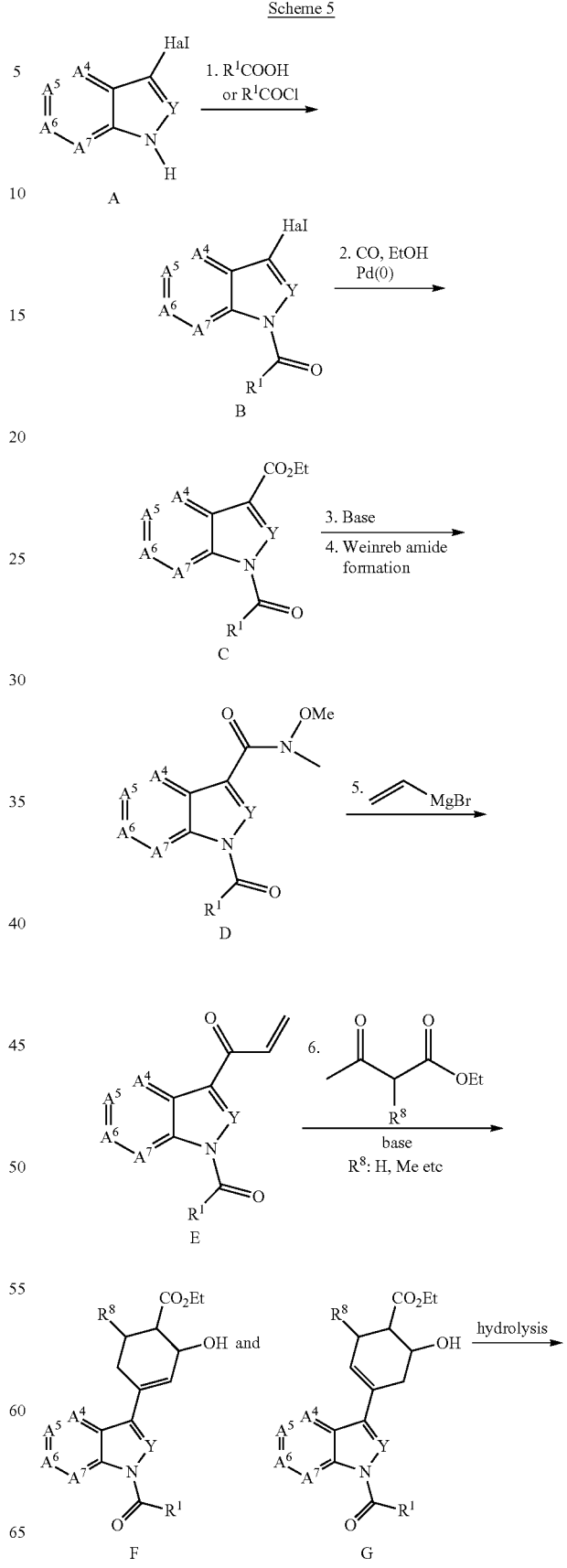

Scheme 5 illustrates a general method for the preparation of compounds of formula I that often are more difficult to access in comparison to those from general methods described previously. N-acylation followed by carbonylation gave intermediate C. Ester hydrolysis, Weinreb formation, and vinyl Grignard addition led to the formation of key intermediate E. Condensation with β-ketone ester afforded two region-isomers F and G. Final ester hydrolysis gave the final product I. Corresponding saturated cyclohexyl analogs could also be obtained from either intermediate F or G via hydrogenation and ester hydrolysis.

-continued

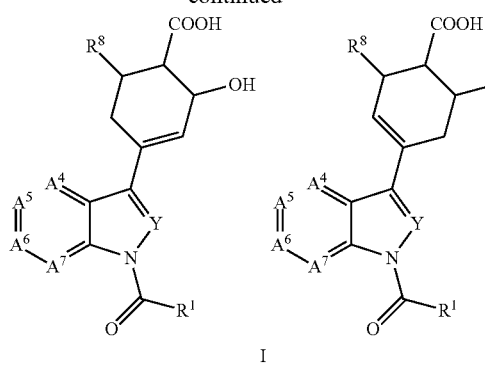

I

COMMERCIALLY AVAILABLE/PREVIOUSLY DESCRIBED MATERIALS

The following table lists commercial sources, and previously disclosed synthetic routes for chemical materials employed in the synthesis of intermediates and that can be used in the synthesis of examples of the instant invention. The list is not intended to be exhaustive, exclusive, or limiting in any way.

| Structure | Source |
|---|---|
| 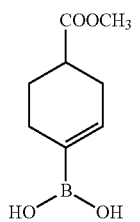 [SMILES: COC(=O)C1CC=C(B(O)O)CC1] | LabPartner |
| 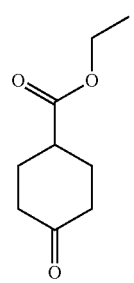 | Aldrich |
| 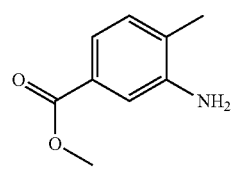 | Aldrich |
| 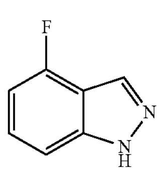 | Oakwood |
| 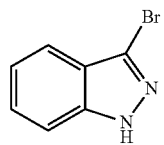 | Aldrich |
| 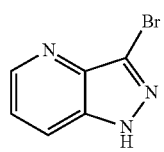 | Frontier |

INTERMEDIATES

Example i-1

Preparation of ethyl 1-methyl-4-(4,4,5,5-tetramethyl-1,3,2-dioxaborolan-2-yl)cyclohex-3-enecarboxylate (i-1)

Scheme i-1

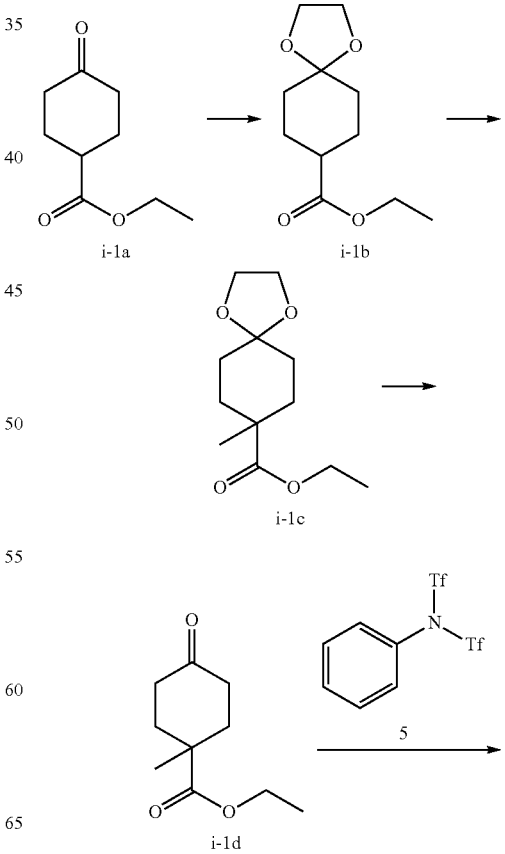

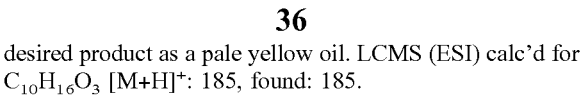

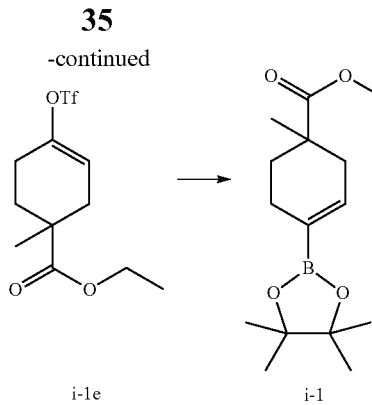

Step 1. Preparation of 1,4-dioxa-spiro[4.5]decane-8-carboxylic acid ethyl ester (i-1b)

A mixture of ethyl 4-oxocyclohexanecarboxylate (i-1a) (5.0 g, 29.41 mmol), ethane-1,2-diol (7.30 g, 117.65 mmol) and 4-methylbenzenesulfonic acid (0.51 g, 2.94 mmol) in toluene (50 mL) was stirred at 100° C. overnight. The solvent was removed under reduced pressure and the residue was diluted with $H_2O$ (50 mL). The aqueous layer was extracted with ethyl acetate (3×50 mL). The combined organic layers were washed with saturated $NaHCO_3$ solution (50 mL) then brine (50 mL), dried over anhydrous $Na_2SO_4$ and concentrated to obtain the desired product as a pale yellow oil. LCMS (ESI) calc'd for $C_{11}H_{18}O_4$ [M+H]$^+$: 215, found: 215.

Step 2. Preparation of ethyl 8-methyl-1,4-dioxa-spiro[4.5]decane-8-carboxylate (i-1c)

A mixture of 1,4-dioxa-spiro[4.5]decane-8-carboxylic acid ethyl ester (i-1b) (4.0 g, 18.69 mmol) in anhydrous THF (40 mL) was cooled to −78° C. in a dry ice-acetone bath and LiHMDS (28 mL, 28.0 mmol) was added dropwise. The mixture was stirred at −78° C. for 1 h. Then CH3I (5.3 g, 37.38 mmol) was added dropwise. The resulting solution was warmed to room temperature and stirring continued overnight. Saturated $NH_4Cl$ solution (50 mL) was added to quench the reaction and the aqueous layer was extracted with EA (3×50 mL). The combined organic layers were washed with brine (50 mL), dried over anhydrous $Na_2SO_4$ and concentrated to obtain the desired product as a pale yellow oil. LCMS (ESI) calc'd for $C_{12}H_{20}O_4$ [M+H]$^+$: 229, found: 229.

Step 3. Preparation of ethyl 1-methyl-4-oxocyclohexanecarboxylate (i-1d)

A mixture of ethyl 8-methyl-1,4-dioxa-spiro[4.5]decane-8-carboxylate (i-1c) (2.0 g, 8.77 mmol) in acetone (20 mL) and 1N $H_2SO_4$ (20 mL) was stirred at room temperature overnight. The mixture was diluted with $H_2O$ (50 mL). The aqueous layer was extracted with DCM (3×30 mL). The combined organic layers were washed with brine (30 mL), dried over anhydrous $Na_2SO_4$ and concentrated to obtain the desired product as a pale yellow oil. LCMS (ESI) calc'd for $C_{10}H_{16}O_3$ [M+H]$^+$: 185, found: 185.

Step 4. Preparation of ethyl 1-methyl-4-(trifluoromethylsulfonyloxy)cyclohex-3-enecarboxylate (i-1e)

A mixture of ethyl 1-methyl-4-oxocyclohexanecarboxylate (i-1d) (3.0 g, 16.3 mmol) in anhydrous THF (20 mL) was cooled to −78° C. in a dry ice-acetone bath and LiHMDS (18 mL, 17.9 mmol) was added dropwise. The mixture was stirred at −78° C. for 30 min. Then a solution of trifluoro-N-phenyl-N-(trifluoromethylsulfonyl)methanesulfonamide 5 (5.37 g, 14.7 mmol) in anhydrous THF (20 mL) was added dropwise. The resulting solution was warmed to room temperature and continued to stir for 3 h. Saturated $NH_4Cl$ solution (50 mL) was added to quench the reaction and the aqueous layer was extracted with EA (3×50 mL). The combined organic layers were washed with brine (50 mL), dried over anhydrous $Na_2SO_4$ and concentrated. The residue was chromatographed on silica gel (PE:EA 100:1) to obtain the desired product as a colorless oil. LCMS (ESI) calc'd for $C_{11}H_{15}F_3O_5S$ [M+H]$^+$: 317, found: 317.

Step 5. Preparation of ethyl 1-methyl-4-(4,4,5,5-tetramethyl-1,3,2-dioxaborolan-2-yl)cyclohex-3-enecarboxylate (i-1)

A mixture of ethyl 1-methyl-4-(trifluoromethylsulfonyloxy)cyclohex-3-enecarboxylate (i-1e) (2.7 g, 8.54 mmol), 4,4,4',4',5,5,5',5'-octamethyl-2,2'-bi(1,3,2-dioxaborolane) (2.39 g, 9.40 mmol), KOAc (2.51 g, 25.62 mmol), dppf (0.31 g, 0.56 mmol) and Pd(dppf)Cl$_2$ (0.31 g, 0.43 mmol) in 1,4-dioxane (50 mL) was heated to 80° C. and stirred at this temperature for 3 h. The solvent was removed under reduced pressure and the residue was diluted with 100 mL of water. The aqueous layer was extracted with ethyl acetate (3×50 mL). The combined organic layers were washed with brine (50 mL), dried over anhydrous $Na_2SO_4$ and concentrated. The residue was purified by silica gel chromatograph (PE:EA 100:1) to provide the desired product as a colorless oil. LCMS (ESI) calc'd for $C_{16}H_{27}BO_4$ [M+H]$^+$: 295, found: 295.

Example i-2

Preparation of 3-bromo-1H-pyrazolo[4,3-b]pyridine

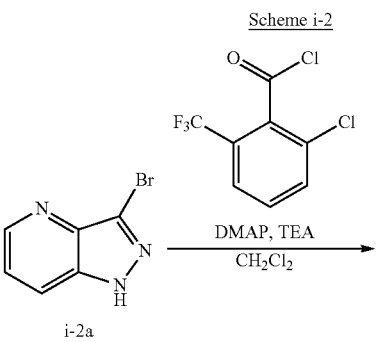

-continued

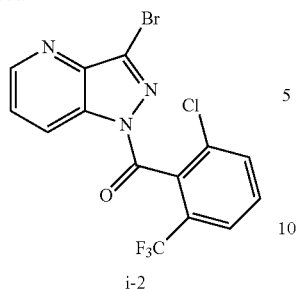

i-2

-continued

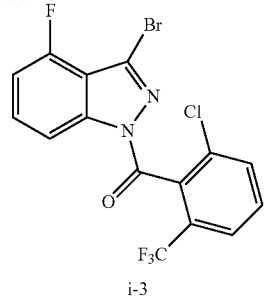

i-3

Step 1. Preparation of (3-bromo-1H-pyrazolo[4,3-b] pyridin-1-yl)(2-chloro-6-(trifluoro methyl)phenyl) methanone (i-2)

To a flask was added 3-bromo-1H-pyrazolo[4,3-b]pyridine (i-2a) (3.2 g, 16.2 mmol), 2-chloro-6-(trifluoromethyl) benzoyl chloride 2 (3.9 g, 16.2 mmol), DMAP (1.97 g, 16.2 mmol) and DCM (60 mL), followed by the addition of TEA (3.26 g, 32.4 mmol) slowly. The reaction mixture was stirred at 40° C. for 3 h. The mixture was diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by flash chromatography (Petroleum/ EtOAc, 5/1) to afford 3.0 g (46%) of the title compound. LCMS (ESI) calc'd for C$_{14}$H$_6$BrClF$_3$N$_3$O [M+H]$^+$: 406, found: 406.

Example i-3

Preparation of (3-bromo-4-fluoro-1H-indazol-1-yl) (2-chloro-6-(trifluoromethyl)phenyl)methanone Scheme i-3

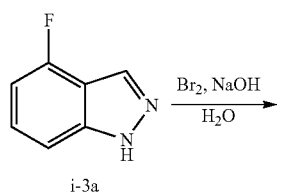

i-3a

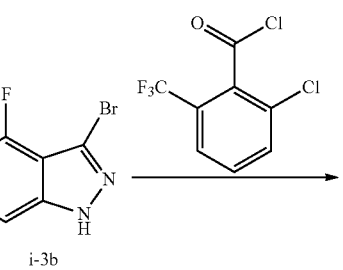

i-3b

Step 1. Preparation of 3-bromo-4-fluoro-1H-indazole (i-3b)

To a suspension of 4-fluoro-1H-indazole (i-3a) (5 g, 36.8 mmol) in 2M sodium hydroxide solution (100 ml) at room temperature was added a solution of bromine (5.8 g, 36.8 mmol) in 2M sodium hydroxide solution (60 ml). The reaction mixture was stirred at room temperature for 3 h. To the reaction mixture was added sodium bisulfite aqueous solution (10%, 100 mL). The solution was extracted with ethyl acetate (2×150 mL). The combined organic layer was washed with H$_2$O (3×100 mL) and brine (2×150 mL). The solution was dried over anhydrous Na$_2$SO$_4$ and evaporated. 5.47 g product was obtained. Yield 69%. LCMS (ESI) calc'd for C$_7$H$_4$BrFN$_2$ [M+H]$^+$: 215, found: 215.

Step 2 Preparation of (3-bromo-4-fluoro-1H-indazol-1-yl)(2-chloro-6-(trifluoromethyl)phenyl)methanone (i-3)

To a flask was added 3-bromo-4-fluoro-1H-indazole (i-3b) (3.2 g, 14.9 mmol), 2-chloro-6-(trifluoromethyl)benzoyl chloride (5.43 g, 22.35 mmol), DMAP (1.82 g, 14.9 mmol), and TEA (3.02 g, 29.8 mmol). The mixture was stirred at 40° C. for 3 h. The mixture was diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by flash chromatography (Petroleum/ EtOAc, 5/1) to afford 2.8 g (45%) of the title compound. LCMS (ESI) calc'd for C$_{15}$H$_6$BrClF$_4$N$_2$O [M+H]$^+$: 421, found: 421.

Example i-4

(4-chloro-3-iodo-1H-indazol-1-yl)(2-chloro-6-(trifluoromethyl)phenyl)methanone

Scheme i-4

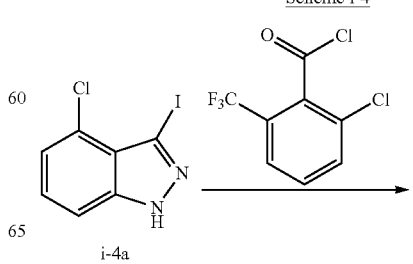

i-4a

-continued

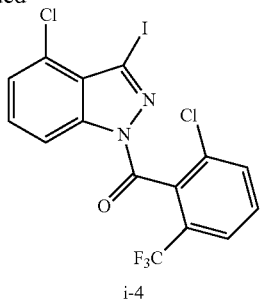

i-4

To a flask was added 4-chloro-3-iodo-1H-indazole (i-4a) (1 g, 3.59 mmol), 2-chloro-6-(trifluoromethyl)benzoyl chloride (1.05 g, 4.31 mmol), DMAP (0.44 g, 3.6 mmol), DCM (7.2 ml) and Et$_3$N (0.75 ml, 5.4 mmol) slowly. The reaction was allowed to stir at room temperature overnight. The mixture was diluted with ethyl acetate, washed 2× with aqueous sodium hydrogen carbonate and 1× with brine. Aqueous layers were back extracted once with ethyl acetate, and combined organic layers were dried over Na$_2$SO$_4$, filtered and the solvent was evaporated under reduced pressure. The residue was purified by flash chromatography (EtOAc/Hexane 0-50%) to give the desired product as a colorless solid (1.5 g, 86%). LCMS (ESI) calc'd for C$_{15}$H$_6$Cl$_2$F$_3$IN$_2$O [M+H]$^+$: 484.8, found: 484.8.

Example i-5

Preparation of 2-chloro-6-cyclopropylbenzoic acid

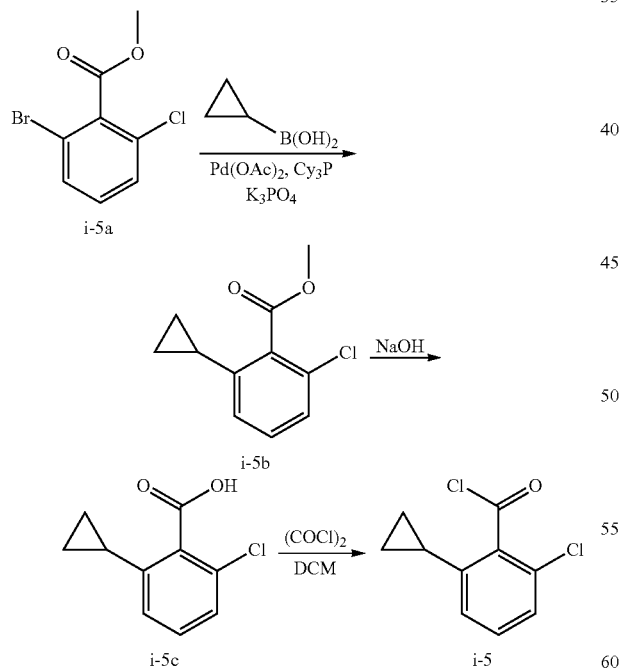

Step 1. Preparation of methyl 2-chloro-6-cyclopropylbenzoate (i-5b)

Methyl 2-bromo-6-chlorobenzoate (i-5a) (1.0 g, 4.0 mmol), cyclopropylboronic acid (516 mg, 6.0 mmol), Pd(OAc)$_2$ (90 mg, 0.4 mmol), Cy$_3$P (224 mg, 0.8 mmol) and K$_3$PO$_4$ (2.5 g, 12.0 mmol) were mixed in toluene (20 ml) and H$_2$O (2.5 ml). The mixture was stirred at 100° C. overnight under N$_2$ atmosphere. The mixture was cooled down and poured into water (50 ml). The mixture was extracted with EA (50 ml). The organic layer was dried over Na$_2$SO$_4$, filtered, and concentrated. The residue was purified by flash chromatography (Petroleum/EtOAc 15/1) to give 0.6 g (71%) of the title compound. LCMS (ESI) calc'd for C$_{11}$H$_{11}$ClO$_2$ [M+H]$^+$: 211, found: 211.

Step 2. Preparation of 2-chloro-6-cyclopropylbenzoic acid (i-5c)

NaOH (380 mg, 9.5 mmol) was added to a solution of methyl 2-chloro-6-cyclopropylbenzoate (i-5b) (200 mg, 0.95 mmol) in EtOH (15 ml) and H$_2$O (6 ml). The resulting solution was stirred at 80° C. overnight. The mixture was cooled down and acidified with diluted HCl to pH=2-3. The mixture was extracted with EA (50 ml). The organic layer was dried over Na$_2$SO$_4$ and concentrated to afford 160 mg (86%) of the title compound. LCMS (ESI) calc'd for C$_{10}$H$_9$ClO$_2$ [M+H]$^+$: 197, found: 197.

Step 3. Preparation of 2-chloro-6-cyclopropylbenzoyl chloride (i-5)

To a solution of 2-chloro-6-cyclopropylbenzoic acid (i-5c) (1 g, 7.19 mmol) in 50 mL of DCM was added oxalyl dichloride (13 mL) at 0° C. dropwise, and the mixture was stirred at 25° C. for 12 h. The mixture was evaporated to dryness. The residue was distilled under reduced pressure to afford 12 g (86%) of the title compound as a yellow oil. LCMS (ESI) calc'd for C$_{10}$H$_8$Cl$_2$O [M+H]$^+$: 215, found: 215.

Example i-6

Preparation of (2-chloro-6-cyclopropylphenyl)(4-fluoro-3-iodo-1H-indazol-1-yl)methanone

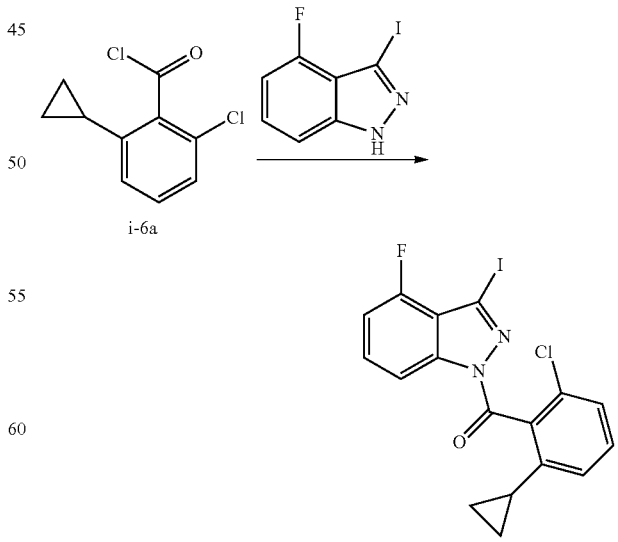

To a suspension of 4-fluoro-3-iodo-1H-indazole (1.14 g, 4.65 mmol) in 20 mL of THF was added NaH (279 mg, 6.9 mmol) at 0° C. The mixture was stirred at 0° C. for 30 minutes. A solution of 2-chloro-6-cyclopropylbenzoyl chloride (i-6a) (1 g, 4.65 mmol) in anhydrous THF (20 mL) was added dropwise to the mixture. The mixture was stirred at 25° C. for an additional 30 minutes. The reaction mixture was quenched with a sat. NH$_4$Cl solution, and was diluted with water (100 mL) and extracted with EtOAc (150 mL×3). The combined organic layers were washed with brine (50 mL×2), dried over Na$_2$SO$_4$ and evaporated to dryness. The residue was purified by column chromatography on silica gel (PE:EtOAc=5:1) to give 1.7 g (86.3%) of the title compound as a yellow solid. LCMS (ESI) calc'd for $C_{17}H_{11}ClFIN_2O$ [M+H]$^+$: 441, found: 441.

Example i-7

Preparation of 1-(2-chloro-6-cyclopropylbenzoyl)-3-iodo-1H-indazole-6-carboxylic acid Scheme i-7

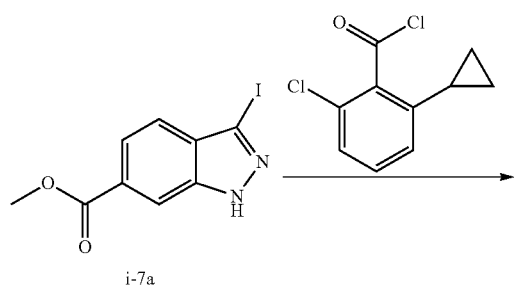

i-7a

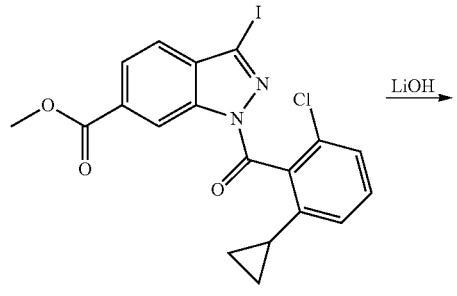

i-7b

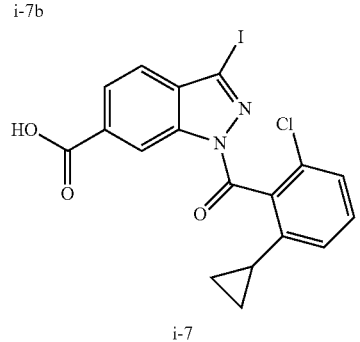

i-7

Step 1: Preparation of 1-(2-chloro-6-cyclopropylbenzoyl)-3-iodo-1H-indazole-6-carboxylate (i-7b)

To a flask was added methyl 3-iodo-1H-indazole-6-carboxylate (i-7a) (1.5 g, 4.97 mmol), TEA (1.730 ml, 12.41 mmol), DMAP (0.061 g, 0.497 mmol), and DCM (9.93 ml). To the solution was added a solution of 2-chloro-6-cyclopropylbenzoyl chloride (1.282 g, 5.96 mmol) in DCM (9.93 ml). The resulting solution was allowed to stir at room temperature for 3 hours. The mixture was diluted with ethyl acetate, washed 2× with aqueous sodium hydrogen carbonate and 1× with brine. Aqueous layers were back extracted once with ethyl acetate. Combined organic layers were dried with Na2SO4, filtered and the solvent was evaporated under reduced pressure. The residue was purified by flash chromatography (EtOAc/Hexane 10-75%) to give the title product as a colorless solid. (2.06 g, 87%) LCMS (ESI) calc'd for $C_{19}H_{14}ClIN_2O_3$ [M+H]$^+$: 480.9, found: 480.9.

Step 2: Preparation of 1-(2-chloro-6-cyclopropylbenzoyl)-3-iodo-1H-indazole-6-carboxylic acid (i-7)

To a vial was added methyl 1-(2-chloro-6-cyclopropylbenzoyl)-3-iodo-1H-indazole-6-carboxylate (i-7b) (1.1 g, 2.288 mmol), lithium hydroxide (1.096 g, 45.8 mmol), THF (3.81 ml), and water (3.81 ml). The reaction was allowed to stir at room temperature overnight. The reaction was concentrated and the residue was purified by flash chromatography (EtOAc/Hexane 0-100%) to give desired product as a colorless solid. (889 mg, 83%) LCMS (ESI) calc'd for $C_{18}H_{12}ClIN_2O_3$ [M+H]$^+$: 466.9, found: 466.9.

Example i-8

Preparation of 3-(4-(tert-butoxycarbonyl)cyclohex-1-en-1-yl)-1-(2-chloro-6-(trifluoromethyl)benzoyl)-1H-indazole-6-carboxylic acid Scheme i-8

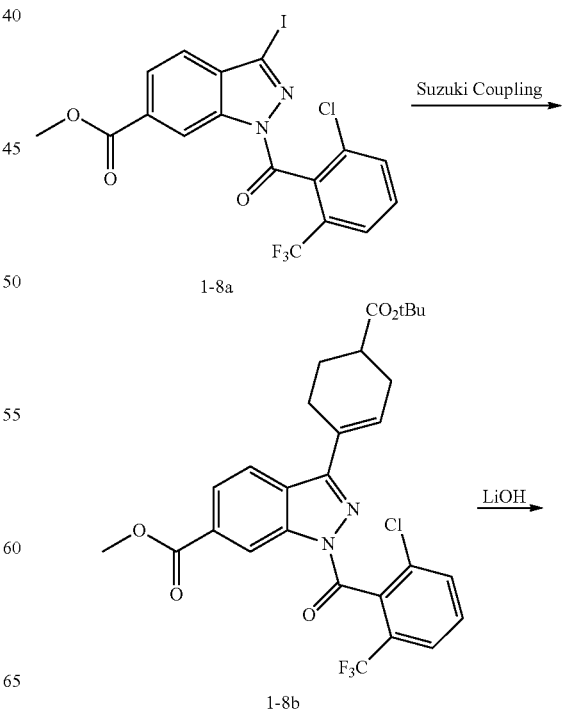

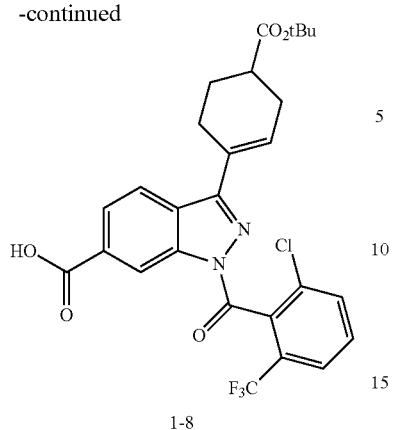

1-8

Step 1: methyl 3-(4-(tert-butoxycarbonyl)cyclohex-1-en-1-yl)-1-(2-chloro-6-(trifluoro methyl)benzoyl)-1H-indazole-6-carboxylate (i-8b)

To a microwave reaction vial was added methyl 1-(2-chloro-6-(trifluoromethyl)benzoyl)-3-iodo-1H-indazole-6-carboxylate (1 g, 1.97 mmol), tert-butyl 4-(4,4,5,5-tetramethyl-1,3,2-dioxaborolan-2-yl)cyclohex-3-enecarboxylate (0.91 g, 2.95 mmol), THF (9.8 ml), and 2M $Na_2CO_3$ (2.95 ml, 5.90 mmol). The mixture was degassed by bubbling $N_2$ for 5 min. 1,1'-bis(diphenylphosphino)ferrocene-palladium (ii)dichloride dichloro methane complex (0.16 g, 0.20 mmol) was added, and the mixture was heated at 50° C. for 2 h. The mixture was cooled down, diluted with $H_2O$, and extracted with EtOAc. The organic layer was washed with brine, dried over $MgSO_4$, and concentrated. The residue was purified by flash chromatography (0-50% EtOAc/hexanes) to give the title compound (0.8 g, 72%). LCMS (ESI) calc'd for: C28H27ClF3N2O5 $[M+H]^+$: 563, found: 563.

Step 2: Preparation of 3-(4-(tert-butoxycarbonyl)cyclohex-1-en-1-yl)-1-(2-chloro-6-(trifluoromethyl)benzoyl)-1H-indazole-6-carboxylic acid (i-8)

To a solution of methyl 3-(4-(tert-butoxycarbonyl)cyclohex-1-en-1-yl)-1-(2-chloro-6-(trifluoromethyl)benzoyl)-1H-indazole-6-carboxylate (i-8b) (0.8 g, 1.421 mmol) in THF (10.66 ml)/MeOH (3.55 ml) was added a solution of LiOH (1M, 2.8 ml). The mixture was stirred at room temperature for 14 h. The mixture was acidified with 2N HCl to pH 3-4, and extracted with EtOAc. The organic layer was washed with brine, dried over $MgSO_4$, and concentrated. The residue was used without purification. LCMS (ESI) calc'd for: $C_{27}H_{25}ClF_3N_2O_5$ $[M+H]^+$: 549, found: 549.

Example i-9

1-(2-chloro-6-(trifluoromethyl)benzoyl)-4-fluoro-N-methoxy-N-methyl-1H-indazole-3-carboxamide Scheme i-9

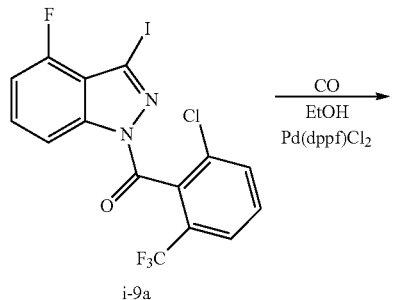

i-9a

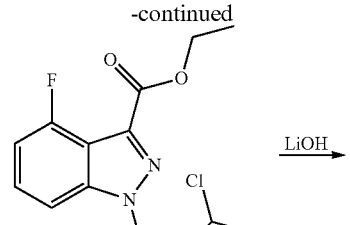

i-9b

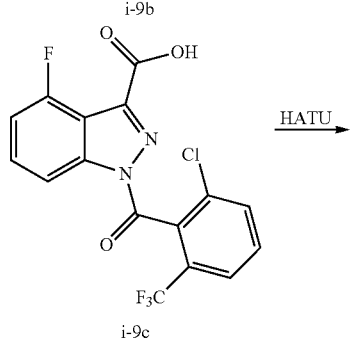

i-9c

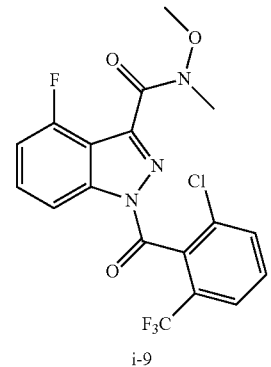

i-9

Step 1. Preparation of ethyl 1-(2-chloro-6-(trifluoromethyl)benzoyl)-4-fluoro-1H-indazole-3-carboxylate (i-9b)

A mixture of (2-chloro-6-(trifluoromethyl)phenyl)(4-fluoro-3-iodo-1H-indazol-1-yl)methanone (i-9a) (2.2 g, 4.72 mmol), $Et_3N$ (1.43 g, 14.2 mmol) and Pd(dppf)Cl$_2$ (200 mg) in EtOH (80 mL) was degassed with CO at 50 Psi and stirred at 80° C. for 20 hours. The mixture was then filtrated and concentrated. The residue was extracted with EA and dried over $Na_2SO_4$. The crude product was purified by column chromatography (PE:EA=10:1) to give the title compound as a white solid (1.3 g, yield: 66%). LCMS (ESI) calc'd for $C_{18}H_{11}ClF_4N_2O_3$ $[M+H]^+$: 415, found: 415.

Step 2. Preparation of 1-(2-chloro-6-(trifluoromethyl)benzoyl)-4-fluoro-1H-indazole-3-carboxylic acid (i-9c)

A solution of ethyl 1-(2-chloro-6-(trifluoromethyl)benzoyl)-4-fluoro-1H-indazole-3-carboxylate (i-9b) (500 mg, 1.21 mmol) and LiOH.H$_2$O (152 mg, 3.62 mmol) in THF/H$_2$O (5 mL/1 mL) was stirred at 25° C. for 10 hours. The mixture was acidified with HCl (a.q.) to pH=1 and was then extracted with EtOAc (100 mL×5). The combined organics were washed with brine and dried over Na$_2$SO$_4$. The title compound (420 mg, yield: 90%) was used in the next step without further purification. LCMS (ESI) calc'd for C$_{16}$H$_7$ClF$_4$N$_2$O$_3$ [M+H]$^+$: 387, found: 387.

Step 3. Preparation of 1-(2-chloro-6-(trifluoromethyl)benzoyl)-4-fluoro-N-methoxy-N-methyl-1H-indazole-3-carboxamide (i-9)

To a solution of 1-(2-chloro-6-(trifluoromethyl)benzoyl)-4-fluoro-1H-indazole-3-carboxylic acid (i-9c) (5 g, 12.95 mmol), HATU (7.38 g, 19.43 mmol) and N,O-dimethylhydroxylamine hydrochloride (1.89 g, 19.43 mmol) in THF (90 mL) was added Et$_3$N (2.62 g, 25.9 mmol) under N$_2$. The mixture was stirred at 25° C. for 10 hours. The mixture was quenched with H$_2$O and extracted with EtOAc (500 mL×5). The combined organic phase was washed with brine and dried over Na$_2$SO$_4$. The product was purified by column chromatography (PE:EA=10:1) to afford the title compound as a white solid (5 g, yield: 95%). LCMS (ESI) calc'd for C$_{18}$H$_{12}$ClF$_4$N$_3$O$_3$ [M+H]$^+$: 430, found: 430.

Example i-10

(2-chloro-6-(trifluoromethyl)phenyl)(3-iodo-1H-pyrazolo[4,3-b]pyridin-1-yl)methanone

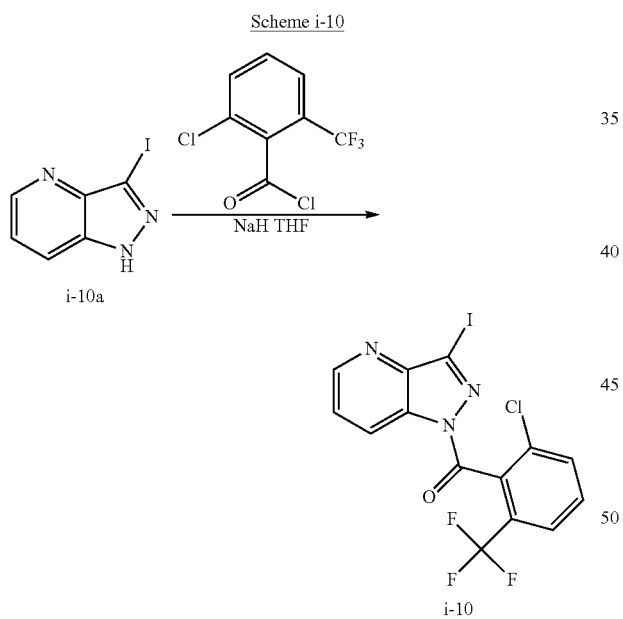

To a suspension of NaH (16 mg, 3.8 mmol, 60% in mineral oil) in 10 mL of dry THF was added 3-iodo-1H-pyrazolo[4,3-b]pyridine (i-10a) (400 mg, 1.6 mmol) portionwise at 0° C. After stirring for 30 min, 2-chloro-6-(trifluoromethyl)benzoyl chloride (480 mg, 1.9 mmol) was added dropwise and the mixture was stirred at 15° C. for 1 h. The resulting mixture was quenched with water (10 mL) and the aqueous layer was extracted with DCM (20 mL×3). The combined organic layer was washed with brine (25 mL), dried over anhydrous sodium sulfate, and concentrated in vacuo to afford the title compound (600 mg, 85%). LCMS (ESI) calc'd for C$_{14}$H$_6$ClF$_3$IN$_3$O [M+H]$^+$: 452, found: 452.

Example i-11

Preparation of ethyl 4-(1-(2-chloro-6-(trifluoromethyl)benzoyl)-4-fluoro-1H-indazol-3-yl)cyclohex-3-enecarboxylate

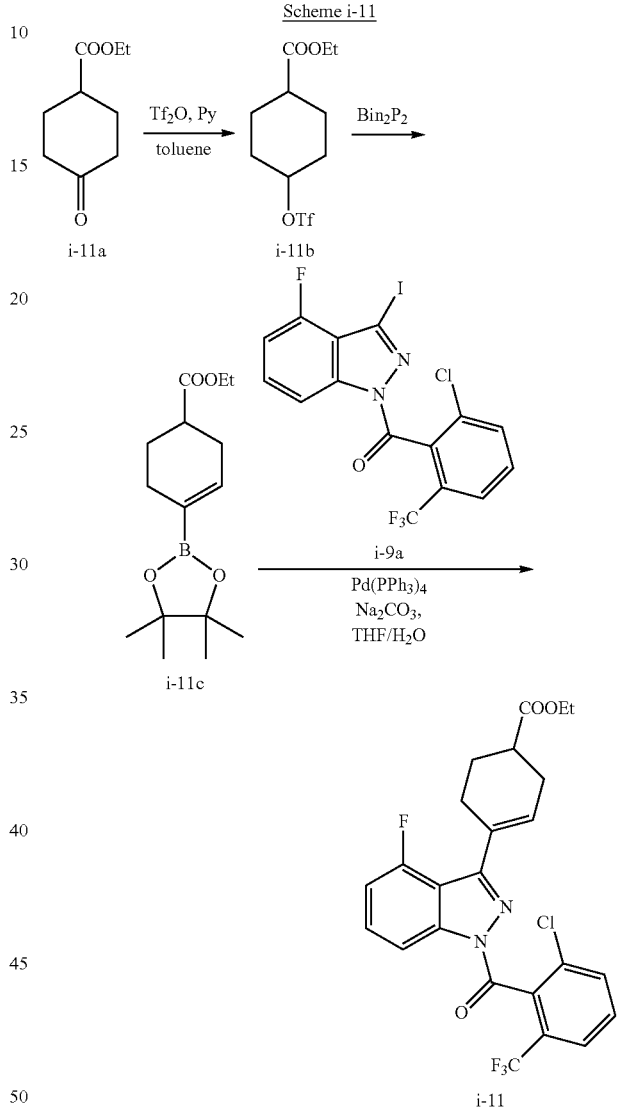

Step 1. ethyl 4-(((trifluoromethyl)sulfonyl)oxy)cyclohex-3-enecarboxylate (i-11b)

To a solution of pyridine (5.2 mL, 6.5 mmol)/toluene (150 mL) was added trifluoromethanesulfonic anhydride (11 mL, 6.5 mmol), over 30 minutes at 15° C., while under nitrogen. A solution of ethyl 4-oxocyclohexanecarboxylate (i-11a) (10 g, 5.88 mmol) in toluene (5 mL) was added, and the mixture was heated to 40° C. An additional batch of trifluoromethanesulfonic anhydride (0.05 mmol) was added after 10 h and 12 h respectively, to push the reaction to completion. The resulting mixture was poured into ice water (200 mL) and extracted with ethyl acetate (200 mL×3). The combined organic layer was washed with brine (200 mL), dried over anhydrous Na₂SO₄ and concentrated in vacuo. The residue was purified by column chromatography on silica gel (PE:EtOAc=30:1) to give the title compound (8 g, 47%) as a yellow oil. LCMS (ESI) calc'd for $C_{10}H_{13}F_3O_5S$ [M+H]⁺: 303. found: 303.

Step 2 Preparation of ethyl 4-(4,4,5,5-tetramethyl-1,3,2-dioxaborolan-2-yl)cyclohex-3-enecarboxylate (i-11c)

To a solution of ethyl 4-(((trifluoromethyl)sulfonyl)oxy)cyclohex-3-enecarboxylate (i-11b) (20 g, 66.2 mmol) in 1,4-dioxane (500 mL) was added bis(pinacolato)diboron (34 g, 132.4 mmol) and potassium acetate (19 g, 198 mmol). The mixture was purged with nitrogen for 20 minutes, Pd(dppf)Cl₂ (4.9 g, 6.6 mmol) was added and the reaction was stirred at 100° C. for 2 h. The resulting mixture was filtered over Celite and the filtrate was diluted with water (500 mL) and extracted with ethyl acetate (500 mL×3). The combined organic layer was washed with brine (500 mL), dried over anhydrous Na₂SO₄ and concentrated in vacuo. The residue was purified by column chromatography on silica gel (PE:EtOAc=20:1) to give the title compound (12 g, 67%) as a yellow oil. LCMS (ESI) calc'd for $C_{15}H_{25}BO_4$ [M+H]⁺: 281. found: 281.

Step 3 Preparation of ethyl 4-(1-(2-chloro-6-(trifluoromethyl)benzoyl)-4-fluoro-1H-indazol-3-yl)cyclohex-3-enecarboxylate (i-11)

To a mixture of (2-chloro-6-(trifluoromethyl)phenyl)(4-fluoro-3-iodo-1H-indazol-1-yl)methanone (i-9a) (1 g, 2.1 mol) in THF/H₂O (40 mL/10 mL) was added ethyl 4-(4,4,5,5-tetramethyl-1,3,2-dioxaborolan-2-yl)cyclohex-3-enecarboxylate (i-11c) (897 mg, 3.2 mmol) and Na₂CO₃ (667 mg, 6.3 mmol). The mixture was purged with nitrogen for 20 minutes, and then Pd(dppf)Cl₂ (726 mg, 0.63 mmol) was added. The reaction was stirred at 80° C. for 10 h. The resulting mixture was filtered over Celite and the filtrate was diluted with water (50 mL) and extracted with ethyl acetate (50 mL×3). The combined organic layer was washed with brine (50 mL), dried over anhydrous Na₂SO₄ and concentrated in vacuo. The product was purified by column chromatography on silica gel (PE:EtOAc=10:1) to give the title compound (300 mg, 29%) as a brown oil. LCMS (ESI) calc'd for $C_{24}H_{19}ClF_4N_2O_3$ [M+H]⁺: 495, found: 495.

Example i-12

Preparation of 3-(4-(((tert-butyldimethylsilyl)oxy)methyl)-1-methylcyclohexyl)-4-fluoro-1H-indazole Scheme i-12

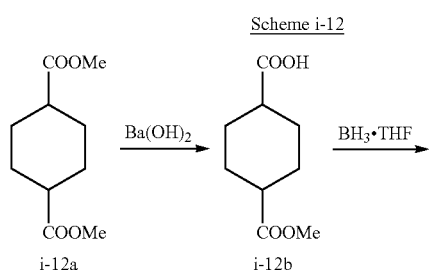

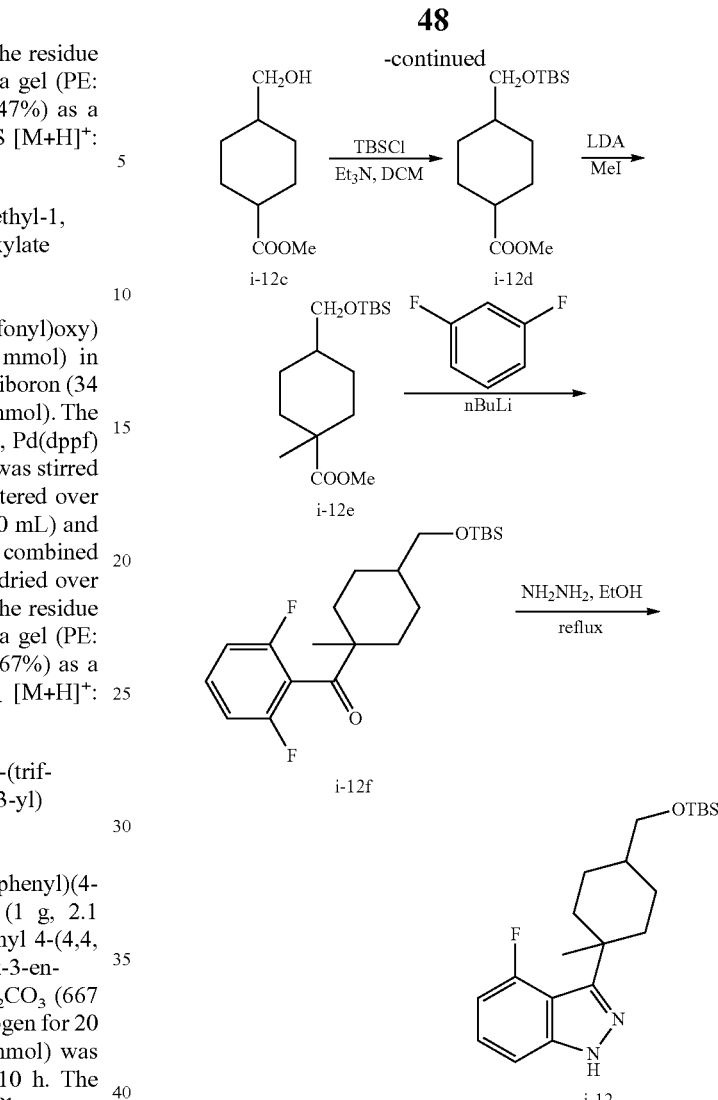

Step 1. Preparation of 4-(methoxycarbonyl)cyclohexanecarboxylic acid (i-12b)

A mixture of dimethyl cyclohexane-1,4-dicarboxylate (i-12a) (8 g, 40 mmol) and barium hydroxide (6.3 g, 20 mmol) in 80% aqueous methanol (150 mL) was stirred at 25° C. for 12 h. The mixture was diluted with water (200 mL) and washed with hexane (100 mL×2) to remove remaining starting material. The aqueous layer was then acidified with 2 M HCl to pH=3 and extracted with EtOAc (100 mL×3). The organic layer was washed with water (100 mL), dried over anhydrous Na₂SO₄, filtered and concentrated in vacuo. The mixture was purified by column chromatography on silica gel (PE:EtOAc=50:1 to 3:1) to afford the title compound (3.2 g, 43%) as a white solid. LCMS (ESI): calc'd for $C_9H_{14}O_4$ [M+H]⁺: 187. found: 187.

Step 2. Preparation of methyl 4-(hydroxymethyl)cyclohexanecarboxylate (i-12c)

To a solution of 4-(methoxycarbonyl)cyclohexanecarboxylic acid (i-12b) (1.5 g, 8.1 mmol) in 15 mL of THF was added dropwise, borane in dimethylsulfane (10 M, 1.6 mL, 16.0 mmol), while cooling to 15° C. in an ice bath. The reaction was stirred at 15° C. for 3 h. The reaction mixture was slowly poured into methanol (500 mL) (cooled in an ice bath), stirred at 15° C. for 30 min and concentrated in vacuo. The residue was partitioned with water (300 mL) and EtOAc (300 mL). The aqueous layer was extracted with EtOAc (300 mL×2) and the combined organic layer was washed with brine (100 mL×2), dried over anhydrous $Na_2SO_4$, filtered and concentrated in vacuo to afford the title compound (1.3 g, 90%) as a yellow oil. LCMS (ESI): calc'd for $C_9H_{16}O_3$ [M+H]$^+$: 173, found: 173.

Step 3. Preparation of methyl 4-(((tert-butyldimethylsilyl)oxy)methyl)cyclohexane carboxylate (i-12d)

To a solution of methyl 4-(hydroxymethyl)cyclohexanecarboxylate (i-12c) (1.3 g, 7.5 mmol) in 30 ml, of DCM, was added triethylamine (2.3 g, 22.6 mmol) and DMAP (46 mg, 0.37 mmol). The reaction was stirred at 15° C. for 30 min. Tert-butylchlorodimethylsilane (1.4 g, 9.1 mmol) was added dropwise, while cooling in an ice bath. The mixture was stirred at 15° C. for 12 h, and was then diluted with DCM (100 mL), and washed with water (100 mL×2). The organic layer was dried over anhydrous $Na_2SO_4$, filtered and concentrated in vacuo. The mixture was purified by column chromatography on silica gel (PE:EtOAc=50:1) to afford the title compound (2 g, 92%) as a yellow oil. LCMS (ESI): calc'd for $C_{15}H_{30}O_3Si$ [M+H]$^+$: 287, found: 287.

Step 4. Preparation of methyl 4-(((tert-butyldimethylsilyl)oxy)methyl)-1-methylcyclohexanecarboxylate (i-12e)

To a solution of 1,2-diisopropylhydrazine (14.1 g, 140 mmol) in 200 mL of anhydrous THF at 0° C., was added dropwise n-BuLi (47.5 mL, 118 mmol). The mixture was stirred at 0° C. for 20 min. A solution of methyl 4-(((tert-butyldimethylsilyl)oxy)methyl)cyclohexanecarboxylate (i-12d) (20 g, 70 mmol) in 100 mL of THF was added dropwise. The mixture was then stirred at 0° C. for 1 h. It was then cooled to −78° C., and iodomethane (19.8 g, 140 mmol) was added dropwise. After the addition was complete, the mixture was stirred at −78° C. for an additional 1 h and then stirred at 15° C. for 12 h. The resulting mixture was poured into saturated aq. $NH_4Cl$ (200 mL) solution, and extracted with EtOAc (300 mL×3). The combined organic layers were washed with brine (100 mL×2), dried over anhydrous $Na_2SO_4$, filtered and concentrated in vacuo to afford the title compound (20 g, 95%) as a yellow oil. LCMS (ESI): calc'd for $C_{16}H_{32}O_3Si$ [M+H]$^+$: 301, found: 301.

Step 5. Preparation of (4-(((tert-butyldimethylsilyl)oxy)methyl)-1-methylcyclohexyl)(2,6-difluorophenyl)methanone (i-12f)

To a solution of 1,3-difluorobenzene (4.6 g, 40 mmol) and TMEDA (3.8 g, 33.3 mmol) in 50 mL of THF was added s-BuLi (28.1 mL, 36.6 mmol) at −78° C. The mixture was stirred at −78° C. for 2 h. A solution of methyl 4-(((tert-butyldimethylsilyl)oxy)methyl)-1-methylcyclohexanecarboxylate (i-12e) (10 g, 33.3 mmol) in 50 mL of THF was added. The mixture was stirred at −78° C. for 1 h, and then warmed to 15° C. while stirring for 12 h. The resulting mixture was quenched with saturated aq. $NH_4Cl$ (200 mL), and extracted with EtOAc (300 mL×3). The combined organic layer was washed with brine (100 mL×2), dried over anhydrous $Na_2SO_4$, filtered and concentrated in vacuo to afford the title compound (11 g, 86%) as yellow oil. LCMS (ESI): calc'd for $C_{21}H_{32}F_2O_2Si$ [M+H]$^+$: 383, found: 383.

Step 6. Preparation of 3-(4-(((tert-butyldimethylsilyl)oxy)methyl)-1-methylcyclohexyl)-4-fluoro-1H-indazole (i-12)

A mixture of (4-(((tert-butyldimethylsilyl)oxy)methyl)-1-methylcyclohexyl)(2,6-difluorophenyl)methanone (i-12f) (1 g, 2.6 mmol) in 15 mL of $H_2N$—$NH_2$.$H_2O$ (85%) was stirred at 110° C. for 30 h. The resulting mixture was poured into 100 mL of water and extracted with EtOAc (300 mL×3). The organic layer was washed with brine (100 mL×2), dried over anhydrous $Na_2SO_4$, filtered and concentrated in vacuo. The mixture was purified by column chromatography on silica gel (PE to PE:EtOAc=20:1) to afford the title compound (300 mg, 31%) as a yellow oil. LCMS (ESI): calc'd for $C_{21}H_{33}FN_2OSi$ [M+H]$^+$: 377, found: 377.

Method for Preparation of the Compound

Example 1 A

Preparation of 4-(1-(2-chloro-6-(trifluoromethyl)benzoyl)-6-(dimethyl carbamoyl)-1H-indazol-3-yl)cyclohex-3-enecarboxylic acid (1A)

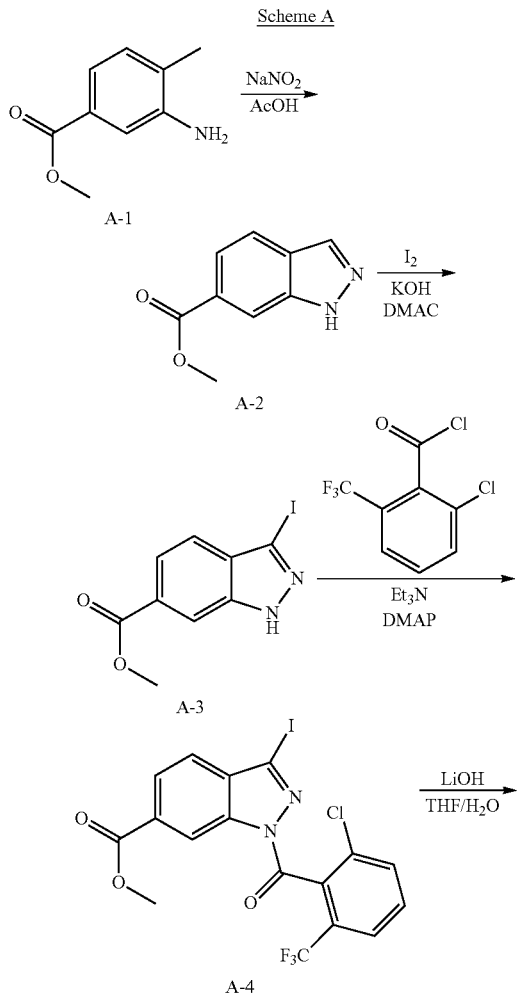

Scheme A

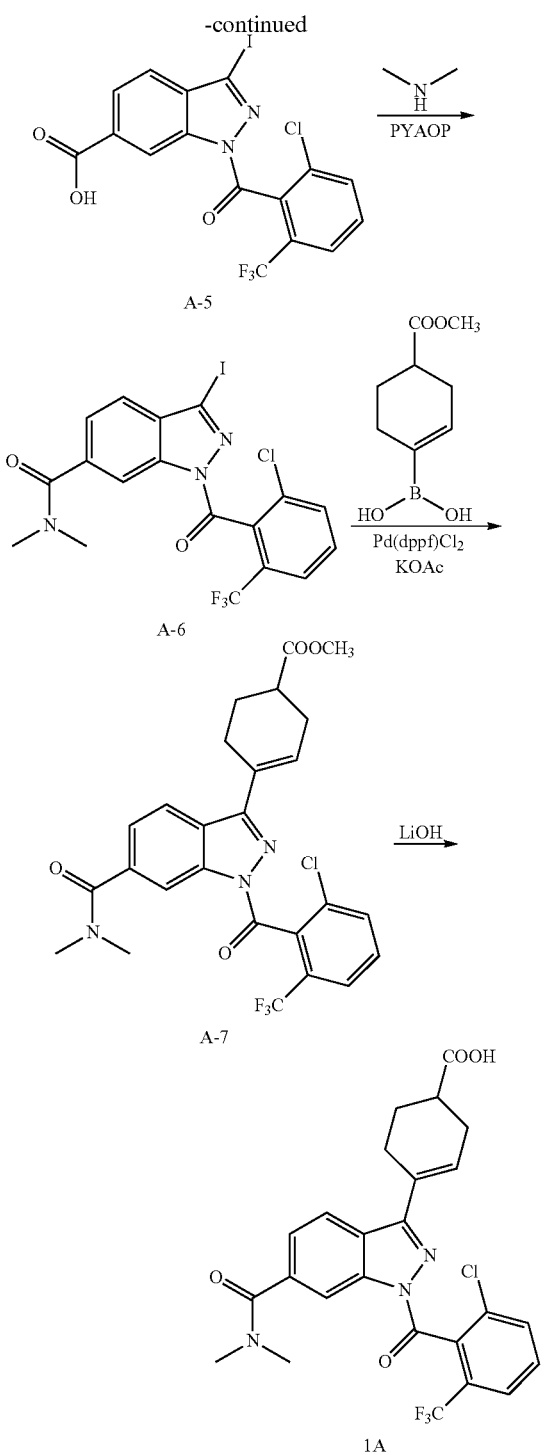

organics were washed with water and brine (2×200 mL), dried and evaporated to afford 2 (4.4 g), yield 83%. LCMS (ESI): calc'd for $C_9H_8N_2O_2$, $[M+H]^+$: 177, found: 177.

Step 2: Preparation of Methyl 3-iodo-1H-indazole-6-carboxylate (A-3)

Methyl 1H-indazole-6-carboxylate (A-2) (5.0 g, 28.3 mmol) was dissolved in anhydrous DMAC (50 mL). Iodine (14.4 g, 56.7 mmol) and potassium hydroxide (6.3 g, 113.5 mmol) were added in portions while stirring at 0° C. The ice bath was removed and the mixture was stirred at room temperature for 1 h. The reaction was monitored by TLC (25% MeOH in chloroform) then it was slowly quenched with $Na_2S_2O_3$ (sat. sol. in water, 100 mL), diluted with water (50 mL) and extracted with EtOAc (3×100 mL). The organic phase was evaporated and triturated with n-hexane. The precipitated material was filtered and dried to afford a brown solid 3 (5.3 g), yield 62%. LCMS(ESI): calc'd for C9H7IN2O2, [M+H]+: 303. found: 303.

Step 3: Preparation of methyl 1-(2-chloro-6-(trifluoromethyl)benzoyl)-3-iodo-1H-indazole-6-carboxylate (A-4)

To a 250 mL round-bottomed flask, was added Methyl 3-iodo-1H-indazole-6-carboxylate 3 (11.7 g, 38.7 mmol), 2-chloro-6-(trifluoromethyl)benzoyl chloride (A-3) (9.1 g, 38.7 mmol), DMAP (4.72 g, 38.7 mmol) and $CH_2Cl_2$ (30 mL). After stirring at room temperature for 3 minutes, TEA (11.2 mL, 77 mmol) was added slowly. The reaction mixture was stirred at room temperature overnight. LCMS indicated that the starting material had been consumed. The mixture was poured into 30 mL of water. The aqueous layer was extracted twice with 20 mL of $CH_2Cl_2$. The combined organic layer was washed with 20 mL×2 water followed by 10 mL of brine. The resulting organic phase was dried over anhydrous sodium sulfate, filtered and concentrated under reduced pressure to give a yellow solid. The residue was purified by column chromatography on 60 g of silica gel eluting with Petroleum ether/EtOAc from 50/1 to 10/1, to give a fawn solid (16.5 g), yield 84%. LCMS (ESI): calc'd for C17H9ClF3IN2O3, [M+H]+: 509, found: 509.

Step 4: Preparation of 1-(2-chloro-6-(trifluoromethyl)benzoyl)-3-iodo-1H-indazole-6-carboxylic acid (A-5)

A mixture of methyl 1-(2-chloro-6-(trifluoromethyl)benzoyl)-3-iodo-1H-indazole-6-carboxylate (A-4) (16.5 g, 32.48 mmol) and LiOH (3.40 g, 162.40 mmol) in 10 ml THF/50 ml $H_2O$ was stirred at room temperature overnight. The solvent was evaporated and the residue was dissolved in water. HCl (5% sol in water) was added to achieve pH=4-5. The precipitated solid was filtered, washed with water and n-hexane, and dried to afford an off-white solid 6 (16.0 g), yield 83%. LCMS(ESI): calc'd for $C_{16}H_7ClF_3IN_2O_3$, $[M+H]^+$: 495, found: 495.

Step 5: Preparation of 1-(2-chloro-6-(trifluoromethyl)benzoyl)-3-iodo-N,N-dimethyl-1H-indazole-6-carboxamide (A-6)

1-(2-chloro-6-(trifluoromethyl)benzoyl)-3-iodo-1H-indazole-6-carboxylic acid (A-5) (178 mg, 0.36 mmol) was dissolved in $CH_2Cl_2$ (15 mL). Dimethylamine (19 mg, 0.42 mmol) and PYAOP (374 mg, 0.72 mmol) were added and Step 1: Preparation of methyl 1H-indazole-6-carboxylate (A-2)

Methyl 3-amino-4-methylbenzoate (A-1) (5.0 g, 30.2 mmol) was dissolved in AcOH (140 mL). Sodium nitrite (2.1 g, 30.2 mmol) in water (3.5 mL) was added drop-wise to the solution while stirring at 0° C. The ice bath was removed and the mixture was stirred overnight. Solvents were evaporated, and the mixture was diluted with water (80 mL) and extracted with EtOAc (3×30 mL). The combined the mixture was stirred at room temperature for 2 minutes. TEA (0.16 mL, 1.08 mmol) was added and the mixture was stirred at room temperature for 2 h. The reaction mixture was diluted with EtOAc (20 ml), washed with brine (2×20 ml), dried over anhydrous $Na_2SO_4$, and concentrated to obtain a white solid 7 (191 mg), yield 97%. LCMS (ESI): calc'd for $C_{18}H_{12}ClF_3IN_3O_2$, $[M+H]^+$: 522, found: 522.

Step 6: Preparation of methyl 4-(1-(2-chloro-6-(trifluoromethyl)benzoyl)-6-(dimethylcarbamoyl)-1H-indazol-3-yl)cyclohex-3-enecarboxylate (A-7)

A mixture of 1-(2-chloro-6-(trifluoromethyl)benzoyl)-3-iodo-N,N-dimethyl-1H-indazole-6-carboxamide (A-6) (318 mg, 0.61 mmol), 4-(methoxycarbonyl)cyclohex-1-enylboronic acid (169 mg, 0.92 mmol), $Pd(dppf)Cl_2$ (50 mg, 0.061 mmol) and KOAc (181 mg, 1.83 mmol) in 10 ml Dioxane/2 ml $H_2O$ was heated to 95° C. for 2 h under microwave irradiation. The crude was diluted with EtOAc (50 ml), washed with brine (2×50 ml), dried over anhydrous $Na_2SO_4$, and concentrated. The mixture was purified by silica gel column (Petroleum ether/EtOAc=20/1) to afford a white solid 8, 192 mg (59%). LCMS (ESI): calc'd for $C_{26}H_{23}ClF_3N_3O_4$, $[M+H]^+$: 534, found: 534.

Step 7: Preparation of 4-(1-(2-chloro-6-(trifluoromethyl)benzoyl)-6-(dimethyl carbamoyl)-1H-indazol-3-yl)cyclohex-3-enecarboxylic acid (1A)

A mixture of methyl 4-(1-(2-chloro-6-(trifluoromethyl)benzoyl)-6-(dimethylcarbamoyl)-1H-indazol-3-yl)cyclohex-3-enecarboxylate (A-7) (37 mg, 0.07 mmol) and $LiOH.H_2O$ (16 mg, 0.37 mmmol) in 10 ml THF/10 ml $H_2O$ was stirred at room temperature for 2 hours. The solvent was evaporated and the residue was dissolved in water. HCl (5% sol in water) was added until pH=4-5 was achieved. The precipitated solid was filtered, washed with water (10 mL), n-hexane (10 mL), and dried to afford an off-white solid 1A. LCMS (ESI): calc'd for $C_{25}H_{21}ClF_3N_3O_4$, $[M+H]^+$: 520, found: 520; $^1$H NMR (400 MHz, MEOD) δ 8.60 (1H, s), 8.19-8.21 (1H, d, J=8.4 Hz), 7.83-7.87 (2H, m), 7.73-7.77 (1H, m), 7.57-7.59 (1H, m), 6.85 (1H, s), 3.21 (3H, s), 3.09 (3H, s), 2.48-2.67 (4H, m), 2.35-2.38 (1H, m), 2.09-2.12 (1H, m), 1.77-1.80 (1H, m).

Example 1B

Preparation of 4-(1-(2-chloro-6-(trifluoromethyl)benzoyl)-4-fluoro-1H-indazol-3-yl)cyclohex-3-enecarboxylic acid (1B)

Scheme B

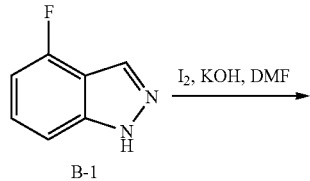
B-1

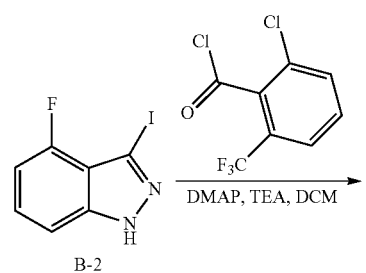
B-2

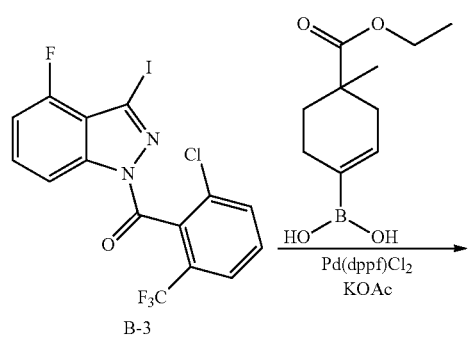
B-3

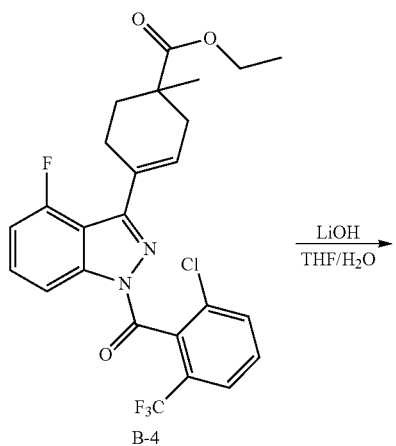
B-4

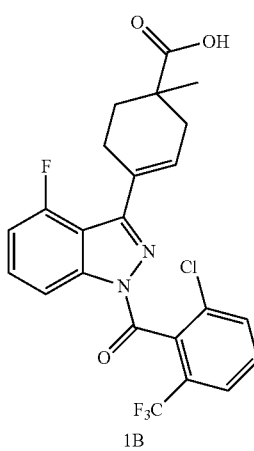
1B

Step 1: Preparation of 4-fluoro-3-iodo-1H-indazole (B-2)

To a solution of 4-fluoroindazole (B-1) (5.00 g, 36.73 mmol) in DMF (80 mL), was added $I_2$ (18.64 g, 73.46 mmol) and KOH (7.73 g, 137.7 mmol) at room temperature while stirring. After 2 hours, TLC indicated that the reaction was complete. The reaction mixture was poured into aq. $NaHSO_3$ (10%, 200 mL) and extracted with EA (3×200 mL). The combined organic layer was washed with $H_2O$ (100 mL) and brine (2×200 mL), dried over anhydrous $Na_2SO_4$, filtered and concentrated. The crude (solid) was washed with PE to give a yellow solid B-2 (8.33 g), yield 86.5%. Physical characterization data for B-2 was as follows: LCMS(ESI): calc. $C_7H_4FIN_2$, 261.9; obs. M+H=262.9.

Step 2: Preparation of (2-chloro-6-(trifluoromethyl)phenyl)(4-fluoro-3-iodo-1H-indazol-1-yl)methanone (B-3)

To a 250 mL round-bottomed flask was added compound B-2 (5.24 g, 20 mmol), 2-chloro-6-(trifluoromethyl)benzoyl chloride (4.86 g, 20 mmol), DMAP (2.44 g, 20 mmol) and DCM (30 mL). The reaction was stirred at room temperature for 3 minutes. TEA (5.8 mL, 40 mmol) was then added slowly. The reaction mixture was stirred at room temperature overnight. LCMS indicated little starting material remaining. The mixture was poured into water (30 mL). The aqueous phase was extracted twice with DCM (20 mL). The combined organic phase was washed with water (2×20 mL), followed by brine (10 mL). The organic phase was dried over anhydrous sodium sulfate, filtered and concentrated under reduced pressure to give a yellow solid. The residue was purified by column chromatography on 30 g of silica gel eluting with PE/EA from 50/1 to 10/1, to give a fawn solid B-3 (7.8 g), yield 83%. LCMS(ESI): calc'd for $C_{15}H_6ClF_4IN_2O$, [M+H]$^+$: 469. Found: 469.

Step 3: Preparation of methyl 4-(1-(2-chloro-6-(trifluoromethyl)benzoyl)-4-fluoro-1H-indazol-3-yl)cyclohex-3-enecarboxylatee (B-4)

A mixture of B-3 (300 mg, 0.64 mmol), 4-(ethoxycarbonyl)-4-methylcyclohex-1-enylboronic acid (203 mg, 0.96 mmol), Pd(dppf)Cl$_2$ (52.2 mg, 0.064 mmol) and KOAc (190 mg, 1.92 mmol) in Dioxane (10 ml)/H$_2$O (2 mL) was heated to 90° C. for 2 h under microwave irradiation. The mixture was diluted with CH$_2$Cl$_2$ (50 ml), washed with brine (2×50 ml), dried over anhydrous Na$_2$SO$_4$, and concentrated. The mixture was purified by silica gel column (PE/EA=20/1) to afford 172 mg of a yellow solid B-4. LCMS(ESI): calc'd for $C_{25}H_{21}ClF_4N_2O_3$, [M+H]$^+$: 509. Found, 509.

Step 4: Preparation of 4-(1-(2-chloro-6-(trifluoromethyl)benzoyl)-4-fluoro-1H-indazol-3-yl)cyclohex-3-enecarboxylic acid (B-5)

A mixture of B-4 (182 mg, 0.36 mmol) and LiOH (350 mg, 1.44 mmol) in 5 ml THF/5 ml H$_2$O was stirred at room temperature for one week. HCl (2 mol/L) was added slowly to maintain the PH<7. The mixture was concentrated under reduced pressure, and filtered to afford a white solid. The white solid was washed with H$_2$O and dried to yield 100 mg of white solid 1B. LCMS(ESI): calc'd for $C_{23}H_{17}ClF_4N_2O_3$, [M+H]$^+$: 481. Found, 481. $^1$H NMR (400 MHz, MeOD) δ 8.39(1H, d, J=8.0 Hz), 7.86-7.83(2H, m), 7.77-7.70(2H, m), 7.27-7.22(1H, m), 6.66(1H, s), 2.84-2.78(1H, m), 2.39-2.38(2H, m), 2.20-2.14(1H, m), 2.07-1.95(1H, m), 1.71-1.64(1H, m), 1.27(3H, d, J=0.8 Hz).

The following examples shown in TABLE 1 were prepared following similar procedures described for Examples 1A in Scheme A and Example 1B in Scheme B, which can be achieved by those of ordinary skill in the art of organic synthesis in light of the present disclosure.

TABLE 1

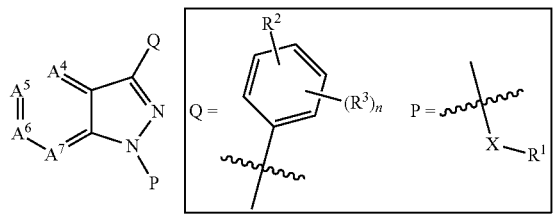

| | Chemical Name | A ring | P | Q | LCMS [M + H]$^+$ Found |
|---|---|---|---|---|---|
| 1C | 4-(1-(2-chloro-6-(trifluoromethyl)benzoyl)-4-fluoro-1H-indazol-3-yl)cyclohex-3-enecarboxylic acid | F | | Cl, F$_3$C | 467 |

TABLE 1-continued

| | Chemical Name | A ring | P | Q | LCMS [M + H]+ Found |
|---|---|---|---|---|---|
| 1D | 4-(1-(2-chloro-6-(trifluoromethyl)benzoyl)-6-(2-hydroxyethylcarbamoyl)-1H-indazol-3-yl)cyclohex-3-enecarboxylic acid | | | | 536 |
| 1E | 4-(1-(2-chloro-6-(trifluoromethyl)benzoyl)-1H-pyrazolo[4,3-b]pyridin-3-yl)cyclohex-3-enecarboxylic acid | | | | 450 |
| 1F | 4-(1-(2-chloro-6-(trifluoromethyl)benzoyl)-1H-pyrazolo[4,3-b]pyridin-3-yl)-1-methylcyclohex-3-enecarboxylic acid | | | | 464 |
| 1G | 4-(1-(2-chloro-6-(trifluoromethyl)benzoyl)-1H-pyrazolo[4,3-b]pyridin-3-yl)-2-methylcyclohex-3-enecarboxylic acid | | | | 464 |
| 1H | 4-(1-(2-chloro-6-(trifluoromethyl)benzoyl)-1H-indazol-3-yl)cyclohex-3-enecarboxylic acid | | | | 449 |

TABLE 1-continued

| | Chemical Name | A ring | P | Q | LCMS [M + H]+ Found |
|---|---|---|---|---|---|
| 1I | 4-(4-chloro-1-(2-chloro-6-(trifluoromethyl)benzoyl)-1H-indazol-3-yl)-1-methylcyclohex-3-enecarboxylic acid | | | | 497 |
| 1J | 4-(1-(2-chloro-6-cyclopropylbenzoyl)-4-fluoro-1H-indazol-3-yl)-1-methylcyclohex-3-enecarboxylic acid | | | | 453 |
| 1K | 4-(1-(2-chloro-6-methylbenzoyl)-4-fluoro-1H-indazol-3-yl)cyclo-hex-3-enecarboxylic acid | | | | 413 |
| 1L | 4-(1-(2-chloro-6-methylbenzoyl)-1H-pyrazolo[4,3-b]pyridine-3-yl)cyclohex-3-enecarboxylic acid | | | | 396 |

Example 2A and 2B
Preparation of (R or S)-4-(1-(2-chloro-6-cyclopropylbenzoyl)-6-(3-methoxy azetidine-1-carbonyl)-1H-indazol-3-yl)cyclohex-3-enecarboxylic acid (2A) and (S or R)-4-(1-(2-chloro-6-cyclopropylbenzoyl)-6-(3-methoxy azetidine-1-carbonyl)-1H-indazol-3-yl)cyclohex-3-enecarboxylic acid (2B)
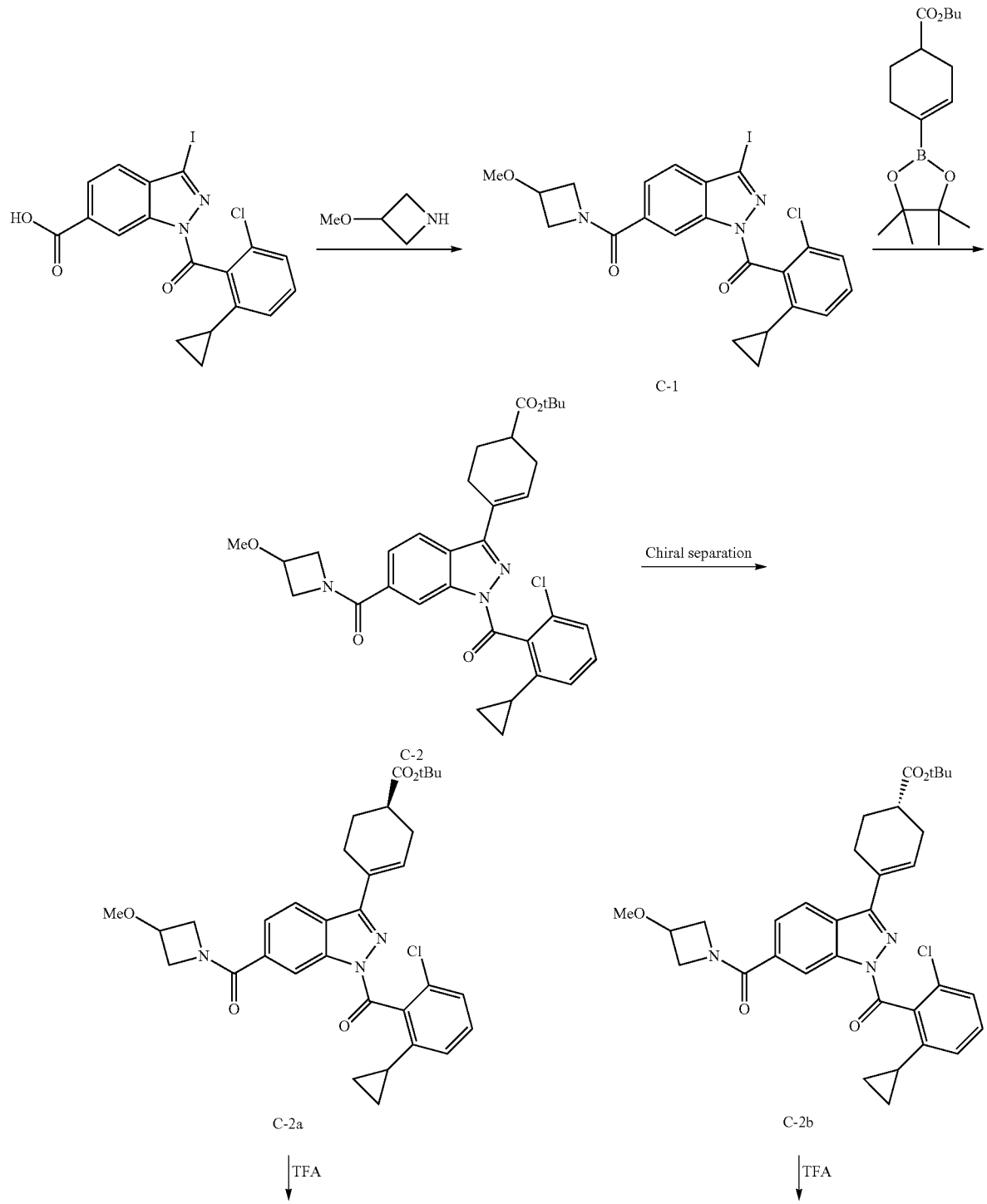
Scheme C

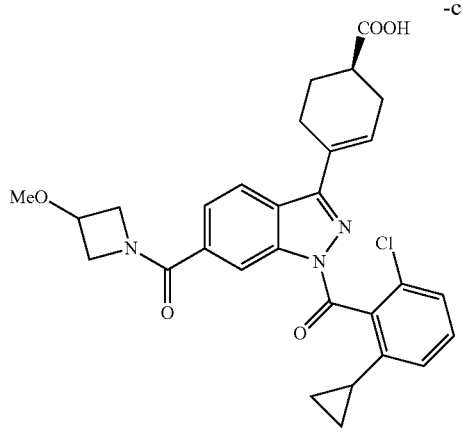

2A

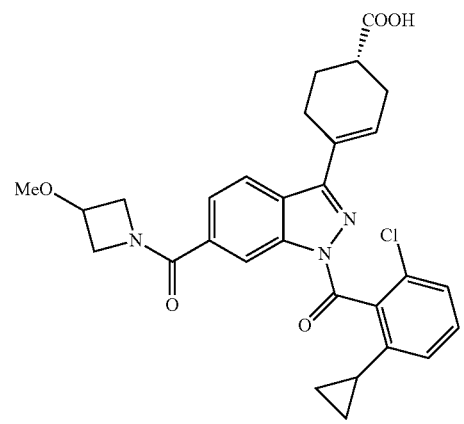

2B

Step 1: Preparation of (1-(2-chloro-6-cyclopropyl-benzoyl)-3-iodo-1H-indazol-6-yl)(3-methoxyazeti-din-1-yl)methanone (C-1)

To a vial was added 1-(2-chloro-6-cyclopropylbenzoyl)-3-iodo-1H-indazole-6-carboxylic acid (889 mg, 1.905 mmol), 3-methoxyazetidine hydrochloride (330 mg, 2.67 mmol), HATU (1449 mg, 3.81 mmol), DIPEA (1331 μl, 7.62 mmol), and DMF (3810 μl). The solution was stirred at room temperature overnight. The mixture was diluted with ethyl acetate, washed 2× with aqueous sodium hydrogen carbonate and 1× with brine. The aqueous layer was back extracted once with ethyl acetate, combined organic layers were dried with Na2SO4, filtered and the solvent was evaporated under reduced pressure. The residue was purified by flash chromatography (EtOAc/Hexane 10-95%) to give desired product as a yellow solid. (1.02 g, 100%) LCMS (ESI) calc'd for $C_{22}H_{19}ClIN_3O_3$ [M+H]$^+$: 536, found: 536.

Step 2: Preparation of tert-butyl 4-(1-(2-chloro-6-cyclopropylbenzoyl)-6-(3-methoxy azetidine-1-carbonyl)-1H-indazol-3-yl)cyclohex-3-enecarboxylate (C-2)

To a vial was added (1-(2-chloro-6-cyclopropylbenzoyl)-3-iodo-1H-indazol-6-yl)(3-methoxyazetidin-1-yl)methanone (C-1) (300 mg, 0.560 mmol), tert-butyl 4-(4,4,5,5-tetramethyl-1,3,2-dioxaborolan-2-yl)cyclohex-3-enecarboxylate (259 mg, 0.840 mmol), (2-dicyclohexylphosphino-2',4',6'-triisopropyl-1,1'-biphenyl)[2-(2-aminoethyl)phenyl]palladium(ii) chloride (83 mg, 0.112 mmol), and THF (2800 μl). The reaction was degassed with argon for 5 minutes. To the solution was added potassium phosphate tribasic (700 μl, 1.400 mmol) and the resulting solution was heated to 80° C. overnight. The mixture was cooled, diluted with ethyl acetate, washed 2× with aqueous sodium hydrogen carbonate and 1× with brine. Aqueous layers were back extracted once with ethyl acetate, combined organic layers were dried over Na2SO4, filtered and the solvent was evaporated under reduced pressure. The residue was purified by Prep-HPLC (Acetonitrile/Water+ 0.10% TFA 50-100%) to give the desired product as a colorless solid. Chiral separation afforded two separate enantiomers: (Peak 1—C-2a, 126.9 mg, 38%) (Peak 2—C-2b, 136 mg, 41%) LCMS (ESI) calc'd for $C_{33}H_{36}ClN_3O_5$ [M+H]$^+$: 590, found: 590.

Step 3: Preparation of (R or S)-4-(1-(2-chloro-6-cyclopropylbenzoyl)-6-(3-methoxy azetidine-1-carbonyl)-1H-indazol-3-yl)cyclohex-3-enecarboxylic acid (2A)

To a vial was added tert-butyl 4-(1-(2-chloro-6-cyclopropylbenzoyl)-6-(3-methoxyazetidine-1-carbonyl)-1H-indazol-3-yl)cyclohex-3-enecarboxylate (peak1, C-2a, 126 mg, 0.214 mmol), DCM (1601 μl), TFA (534 μl) and the solution was allowed to stir for 2 hours. The reaction was concentrated and the residue was purified by Prep-HPLC (Acetonitrile/Water+0.10% TFA 35-100%) to give the title compound as a colorless solid. (48 mg, 42%) LCMS (ESI) calc'd for $C_{29}H_{28}ClN_3O_5$ [M+H]$^+$: 534, found: 534. $^1$H NMR (600 MHz, DMSO) δ 8.71 (s, 1H), 8.16 (d, J=8.3 Hz, 1H), 7.71 (d, J=8.3 Hz, 1H), 7.41 (t, J=7.8 Hz, 1H), 7.37 (d, J=7.9 Hz, 1H), 7.05 (d, J=7.7 Hz, 1H), 6.78 (s, 1H), 4.46 (s, 1H), 4.32-4.20 (m, 2H), 4.13 (d, J=7.9 Hz, 1H), 3.88 (d, J=8.4 Hz, 1H), 3.2 (s, 3H), 2.59-2.48 (m, 2H), 2.41-2.18 (m, 3H), 1.96 (d, J=12.1 Hz, 1H), 1.72-1.51 (m, 2H), 0.86-0.48 (m, 4H).

Step 4: Preparation of (S or R)-4-(1-(2-chloro-6-cyclopropylbenzoyl)-6-(3-methoxy azetidine-1-carbonyl)-1H-indazol-3-yl)cyclohex-3-enecarboxylic acid (2B)

Preparation was similar to that for the other enantiomeric ester (peak2, C-2b), and can be achieved by those of ordinary skill in the art of organic synthesis in light of the present disclosure.

The following examples shown in Table 2 were made using the same procedures described for Example 2A and 2B, which can be achieved by those of ordinary skill in the art of organic synthesis in light of the present disclosure.

TABLE 2

| | Chemical Name | Structure | LCMS [M + H]+ Found |
|---|---|---|---|
| 2C | (R or S)-4-(1-(2-chloro-6-cyclopropylbenzoyl)-6-(3-methoxyazetidine-1-carbonyl)-1H-indazol-3-yl)-1-methylcyclohex-3-enecarboxylic acid | chiral | 548 |
| 2D | (S or R)-4-(1-(2-chloro-6-cyclopropylbenzoyl)-6-(3-methoxyazetidine-1-carbonyl)-1H-indazol-3-yl)-1-methylcyclohex-3-enecarboxylic acid | chiral | 548 |

Example 3A and 3B

Preparation (R or S)-4-(1-(2-chloro-6-cyclopropyl-benzoyl)-4-fluoro-1H-indazol-3-yl)cyclohex-3-enecarboxylic acid (3A) and (S or R)-4-(1-(2-chloro-6-cyclopropylbenzoyl)-4-fluoro-1H-indazol-3-yl)cyclohex-3-enecarboxylic acid (3B)

Scheme D

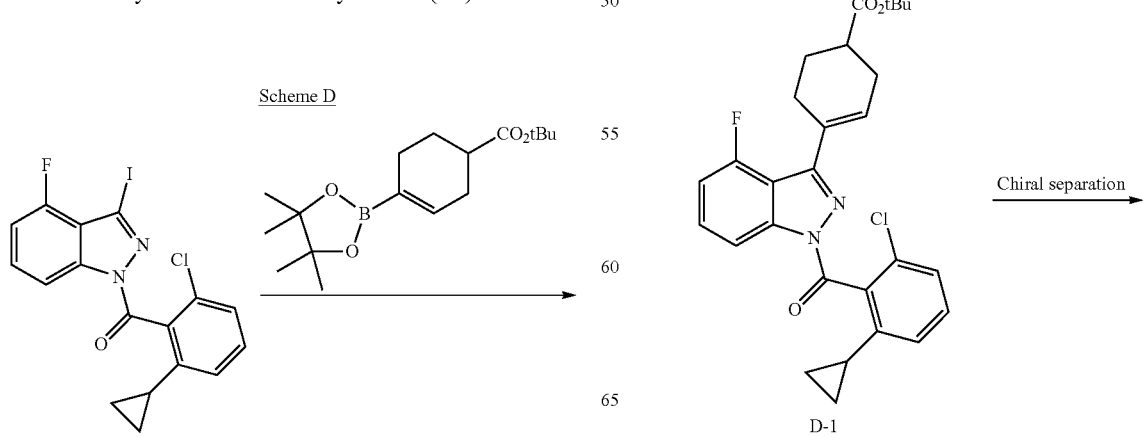

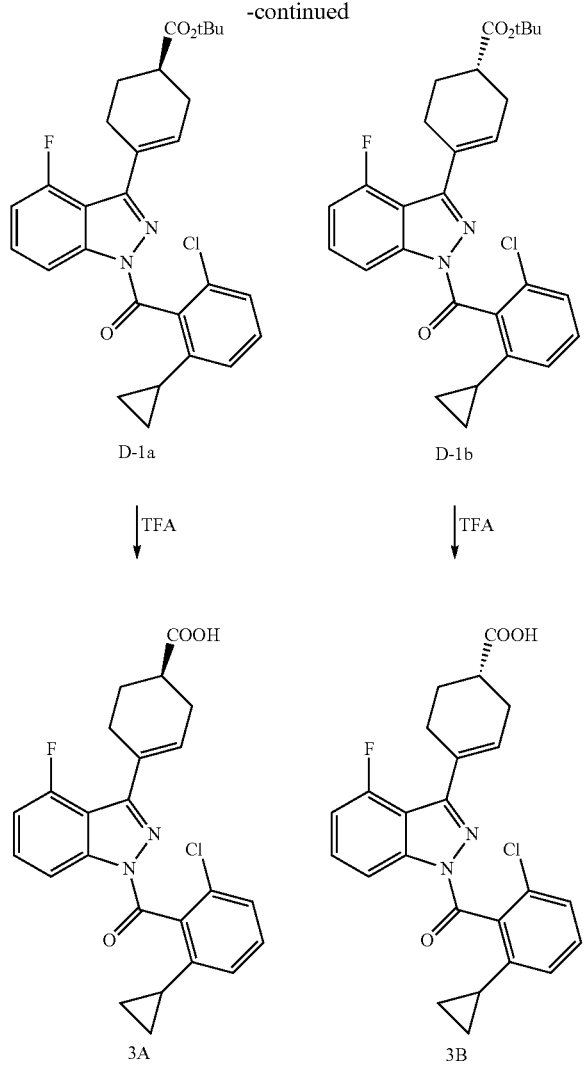

D-1a    D-1b

↓ TFA    ↓ TFA 3A    3B

Step 1: Preparation of tert-butyl 4-(1-(2-chloro-6-cyclopropylbenzoyl)-4-fluoro-1H-indazol-3-yl)cyclohex-3-enecarboxylate (D-1)

To a vial was added (2-chloro-6-cyclopropyl phenyl)(4-fluoro-3-iodo-1H-indazol-1-yl)methanone (220 mg, 0.499 mmol), tert-butyl 4-(4,4,5,5-tetramethyl-1,3,2-dioxaborolan-2-yl)cyclohex-3-enecarboxylate (231 mg, 0.749 mmol), PdCl$_2$(dppf)-CH$_2$Cl$_2$ adduct (82 mg, 0.100 mmol), sodium carbonate (159 mg, 1.498 mmol), and THF (2496 µl). The reaction was degassed with argon for 5 minutes. The reaction was then heated to 80° C. overnight. The next morning the mixture was cooled, diluted with ethyl acetate, washed 2× with aqueous sodium hydrogen carbonate and 1× with brine. The aqueous layer was back extracted once with ethyl acetate, combined organics were dried with Na2SO4, filtered and the solvent was evaporated under reduced pressure. The residue was purified by Prep-HPLC (Acetonitrile/Water+0.10% TFA 65-100%) to give the desired product as a brown solid. Chiral purification afforded two separate enantiomers. (Peak 1—D-1a, 26 mg, 10%) (Peak 2—D-1b, 25 mg, 10%) LCMS (ESI) calc'd for C$_{28}$H$_{28}$ClFN$_2$O$_3$ [M+H]$^+$: 495, found: 495.

Step 2: Preparation (R or S)-4-(1-(2-chloro-6-cyclopropylbenzoyl)-4-fluoro-1H-indazol-3-yl)cyclohex-3-enecarboxylic acid (3A)

To a vial was added tert-butyl 4-(1-(2-chloro-6-cyclopropylbenzoyl)-4-fluoro-1H-indazol-3-yl)cyclohex-3-enecarboxylate (peak1, D-1a, 26 mg, 0.053 mmol), DCM (2 mL), and TFA (0.202 mL, 2.63 mmol). The solution was stirred for two days. The reaction was concentrated and the residue was brought up in methanol, and submitted for Prep-HPLC purification (Acetonitrile/Water+0.10% TFA) to give the product as a colorless solid. (7.6 mg, 33%) LCMS (ESI) calc'd for C$_{24}$H$_{20}$ClFN$_2$O$_3$ [M+H]$^+$: 439. found: 439. $^1$H NMR (600 MHz, DMSO) δ 12.21 (s, 1H), 8.35 (s, 1H), 7.73 (s, 1H), 7.47-7.25 (m, 3H), 7.04 (s, 1H), 6.51 (s, 1H), 2.42-2.19 (m, 5H), 1.94 (s, 1H), 1.62 (s, 2H), 0.83-0.48 (m, 4H).

Step 4: Preparation (S or R)-4-(1-(2-chloro-6-cyclopropylbenzoyl)-4-fluoro-1H-indazol-3-yl)cyclohex-3-enecarboxylic acid (3B)

Preparation was similar to that for the other enantiomeric ester (peak2, D-1b), and can be achieved by those of ordinary skill in the art of organic synthesis in light of the present disclosure.

Example 4A

Preparation of 4-(1-(2-chloro-6-(trifluoromethyl)benzoyl)-6-(3,3-difluoroazetidine-1-carbonyl)-1H-indazol-3-yl)cyclohex-3-enecarboxylic acid Scheme E

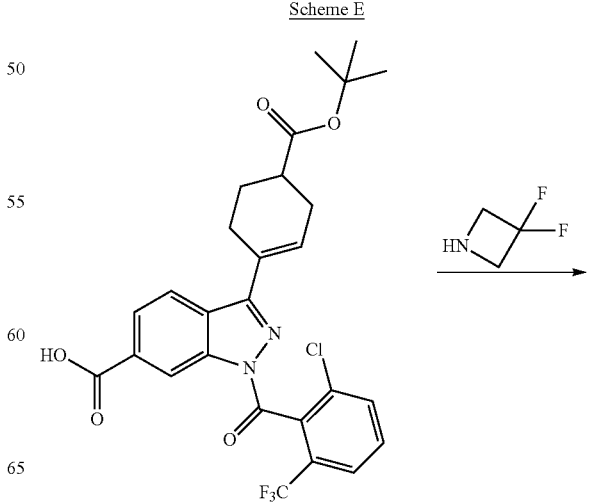

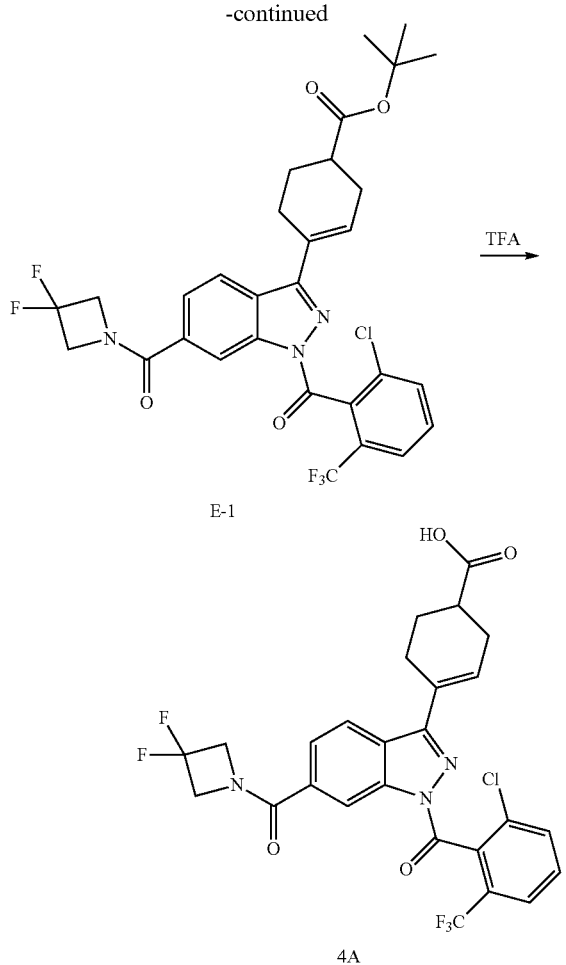

Step 1: Preparation of tert-Butyl 4-(1-(2-chloro-6-(trifluoromethyl)benzoyl)-6-(3,3-difluoroazetidine-1-carbonyl)-1H-indazol-3-yl)cyclohex-3-enecarboxylate (E-1)

To a vial containing 3,3-difluoroazetidine hydrogen chloride salt (11.5 mg, 0.089 mmol) dissolved in DMA (1.0 mL) was added 3-(4-(tert-butoxycarbonyl)cyclohex-1-en-1-yl)-1-(2-chloro-6-(trifluoromethyl)benzoyl)-1H-indazole-6-carboxylic acid (30 mg, 0.055 mmol), N-ethyl-N-isopropylpropan-2-amine (0.050 ml, 0.055 mmol) and HATU (25 mg, 0.066 mmol). The reaction mixture was stirred at room temperature overnight. The following morning the solvent was evaporated under reduced pressure and the material was carried into step 2 without purification. LCMS (ESI) calc'd for $C_{30}H_{28}ClF_5N_3O_4$ [M+H]+: 624, found: 624.

Step 2: Preparation of 4-(1-(2-chloro-6-(trifluoromethyl)benzoyl)-6-(3,3-difluoroazetidine-1-carbonyl)-1H-indazol-3-yl)cyclohex-3-enecarboxylic acid (4A)

Tert-Butyl 4-(1-(2-chloro-6-(trifluoromethyl)benzoyl)-6-(3,3-difluoroazetidine-1-carbonyl)-1H-indazol-3-yl)cyclohex-3-enecarboxylate (E-1) was dissolved in a 1:1 solution of DCM:TFA (0.5 mL) and stirred at room temperature for 1.5 hours. The solvent was evaporated under reduced pressure. DMSO (1.2 mL) was added to dissolve the crude sample and the material was purified by mass triggered prep-HPLC (CH$_3$CN/H$_2$O) to obtain 17.9 mg (57%) of the title compound. LCMS (ESI) calc'd for $C_{26}H_{20}ClF_5N_3O_4$ [M+H]+: 568, found: 568.

The following examples shown in TABLE 3 were prepared following similar procedures described for Examples 4A in Scheme E, which can be achieved by those of ordinary skill in the art of organic synthesis in light of the present disclosure.

TABLE 3

| | IUPAC Name | Structure | LCMS [M + H]+ Found |
|---|---|---|---|
| 4B | 4-(1-(2-chloro-6-(trifluoromethyl)benzoyl)-6-(cyclopropylcarbamoyl)-1H-indazol-3-yl)cyclohex-3-enecarboxylic acid | 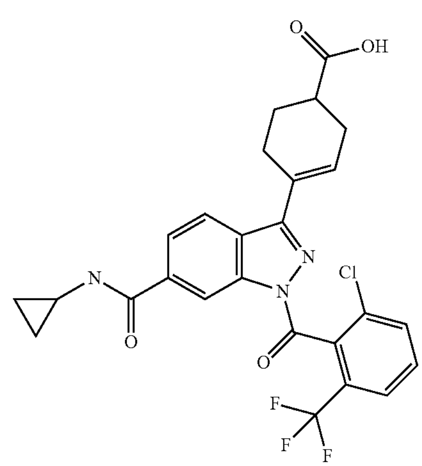 [SMILES: O=C(NC1CC1)c1ccc2c(C3=CCC(C(=O)O)CC3)nn(C(=O)c3c(Cl)cccc3C(F)(F)F)c2c1] | 532 |

TABLE 3-continued

| | IUPAC Name | Structure | LCMS [M + H]+ Found |
|---|---|---|---|
| 4C | 4-(1-(2-chloro-6-(trifluoromethyl)benzoyl)-6-(cyclopropyl(methyl)carbamoyl)-1H-indazol-3-yl)cyclohex-3-enecarboxylic acid | 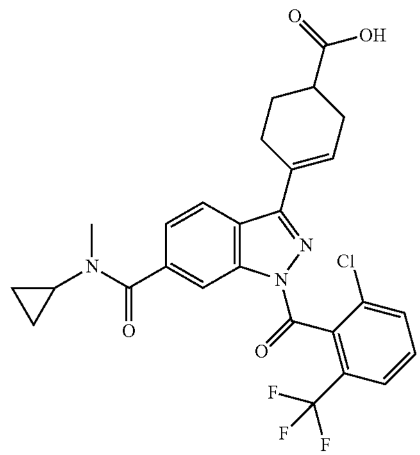 [SMILES: CN(C(=O)c1ccc2c(C3=CCC(C(=O)O)CC3)nn(C(=O)c3c(Cl)cccc3C(F)(F)F)c2c1)C1CC1] | 546 |
| 4D | 4-(6-(azetidine-1-carbonyl)-1-(2-chloro-6-(trifluoromethyl)benzoyl)-1H-indazol-3-yl)cyclohex-3-enecarboxylic acid | 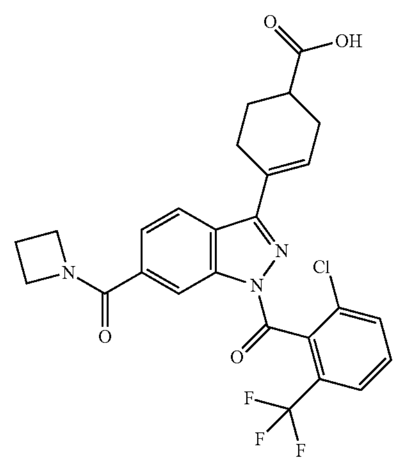 [SMILES: O=C(O)C1CC=C(c2nn(C(=O)c3c(Cl)cccc3C(F)(F)F)c3cc(C(=O)N4CCC4)ccc23)CC1] | 532 |
| 4E | 4-(1-(2-chloro-6-(trifluoromethyl)benzoyl)-6-(3-methoxyazetidine-1-carbonyl)-1H-indazol-3-yl)cyclohex-3-enecarboxylic acid | 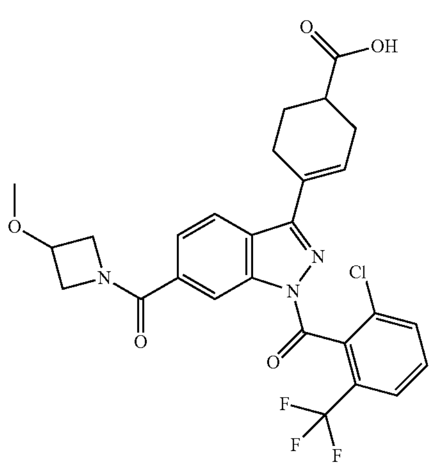 [SMILES: COC1CN(C(=O)c2ccc3c(C4=CCC(C(=O)O)CC4)nn(C(=O)c4c(Cl)cccc4C(F)(F)F)c3c2)C1] | 562 |

TABLE 3-continued

| | IUPAC Name | Structure | LCMS [M + H]+ Found |
|---|---|---|---|
| 4F | 4-(1-(2-chloro-6-(trifluoromethyl)benzoyl)-6-(pyrrolidine-1-carbonyl)-1H-indazol-3-yl)cyclohex-3-enecarboxylic acid | 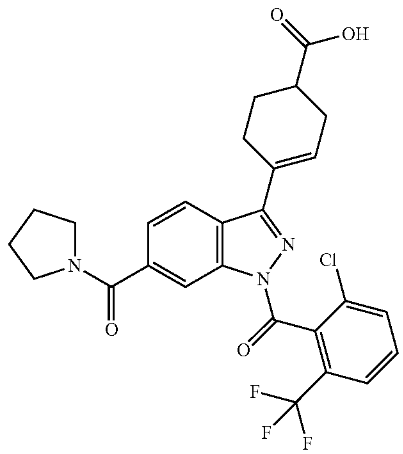 [SMILES: O=C(O)C1CC=C(c2nn(C(=O)c3c(Cl)cccc3C(F)(F)F)c3cc(C(=O)N4CCCC4)ccc23)CC1] | 546 |
| 4G | 4-(1-(2-chloro-6-(trifluoromethyl)benzoyl)-6-((S)-2-methylpyrrolidine-1-carbonyl)-1H-indazol-3-yl)cyclohex-3-enecarboxylic acid | 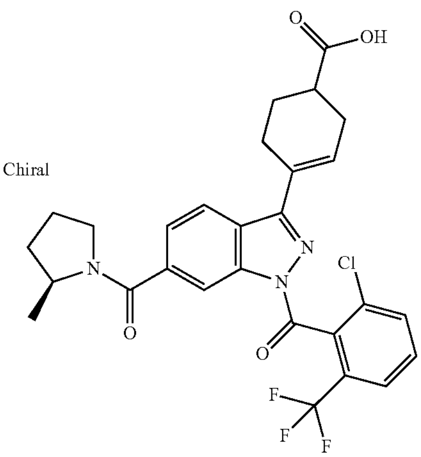 [SMILES: C[C@H]1CCCN1C(=O)c1ccc2c(C3=CCC(C(=O)O)CC3)nn(C(=O)c3c(Cl)cccc3C(F)(F)F)c2c1] | 560 |
| 4H | 4-(1-(2-chloro-6-(trifluoromethyl)benzoyl)-6-((R)-2-methylpyrrolidine-1-carbonyl)-1H-indazol-3-yl)cyclohex-3-enecarboxylic acid | 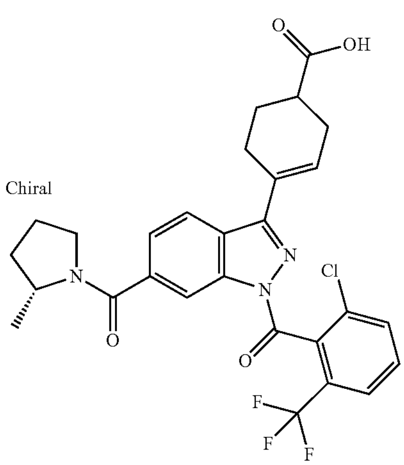 [SMILES: C[C@@H]1CCCN1C(=O)c1ccc2c(C3=CCC(C(=O)O)CC3)nn(C(=O)c3c(Cl)cccc3C(F)(F)F)c2c1] | 560 |

TABLE 3-continued

| | IUPAC Name | Structure | LCMS [M + H]+ Found |
|---|---|---|---|
| 4I | 4-(1-(2-chloro-6-(trifluoromethyl)benzoyl)-6-(3-methoxypyrrolidine-1-carbonyl)-1H-indazol-3-yl)cyclohex-3-enecarboxylic acid | 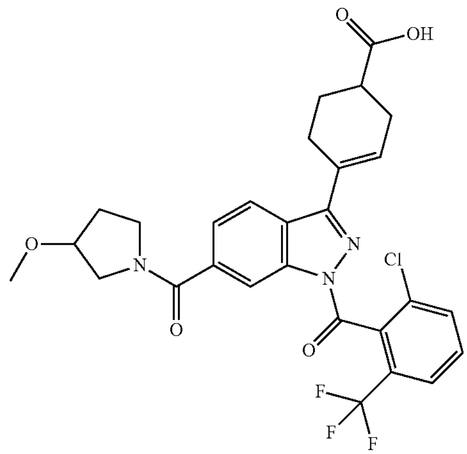 [SMILES: COC1CCN(C(=O)c2ccc3c(C4=CCC(C(=O)O)CC4)nn(C(=O)c4c(Cl)cccc4C(F)(F)F)c3c2)C1] | 576 |
| 4J | 4-(1-(2-chloro-6-(trifluoromethyl)benzoyl)-6-(2-methylmorpholine-4-carbonyl)-1H-indazol-3-yl)cyclohex-3-enecarboxylic acid | 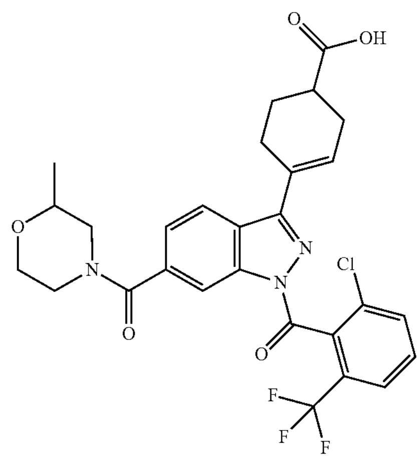 [SMILES: CC1CN(C(=O)c2ccc3c(C4=CCC(C(=O)O)CC4)nn(C(=O)c4c(Cl)cccc4C(F)(F)F)c3c2)CCO1] | 576 |
| 4K | 4-(1-(2-chloro-6-(trifluoromethyl)benzoyl)-6-(cyclohexyl(methyl)carbamoyl)-1H-indazol-3-yl)cyclohex-3-enecarboxylic acid | 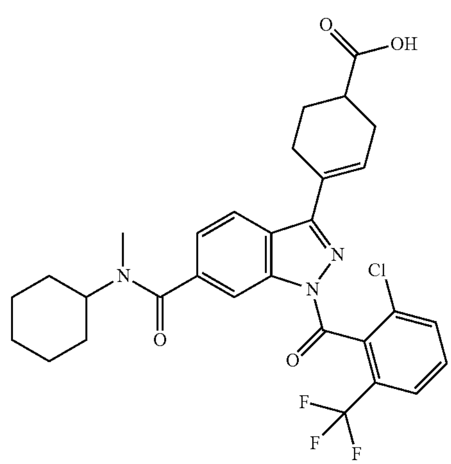 [SMILES: CN(C(=O)c1ccc2c(C3=CCC(C(=O)O)CC3)nn(C(=O)c3c(Cl)cccc3C(F)(F)F)c2c1)C1CCCCC1] | 588 |

TABLE 3-continued

| | IUPAC Name | Structure | LCMS [M + H]+ Found |
|---|---|---|---|
| 4L | 4-(1-(2-chloro-6-(trifluoromethyl)benzoyl)-6-(morpholine-4-carbonyl)-1H-indazol-3-yl)cyclohex-3-enecarboxylic acid | 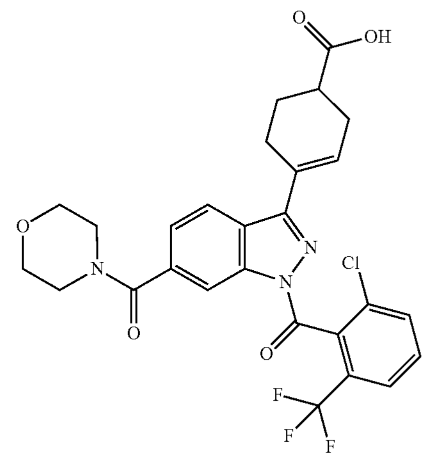 [SMILES: O=C(O)C1CC=C(c2nn(C(=O)c3c(Cl)cccc3C(F)(F)F)c3cc(C(=O)N4CCOCC4)ccc23)CC1] | 562 |
| 4M | 4-(1-(2-chloro-6-(trifluoromethyl)benzoyl)-6-((2R,6S)-2,6-dimethylmorpholine-4-carbonyl)-1H-indazol-3-yl)cyclohex-3-enecarboxylic acid | 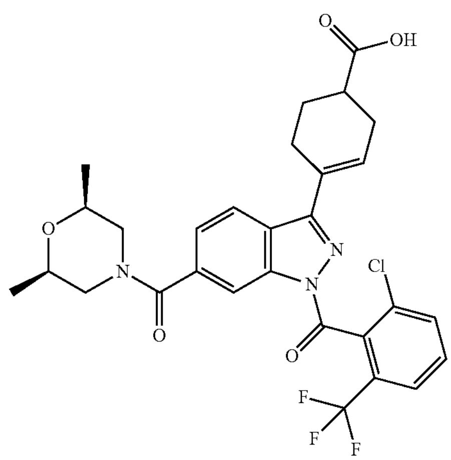 [SMILES: C[C@@H]1CN(C(=O)c2ccc3c(C4=CCC(C(=O)O)CC4)nn(C(=O)c4c(Cl)cccc4C(F)(F)F)c3c2)C[C@H](C)O1] | 590 |
| 4N | 4-(1-(2-chloro-6-(trifluoromethyl)benzoyl)-6-(4-methyl-3-oxopiperazine-1-carbonyl)-1H-indazol-3-yl)cyclohex-3-enecarboxylic acid | 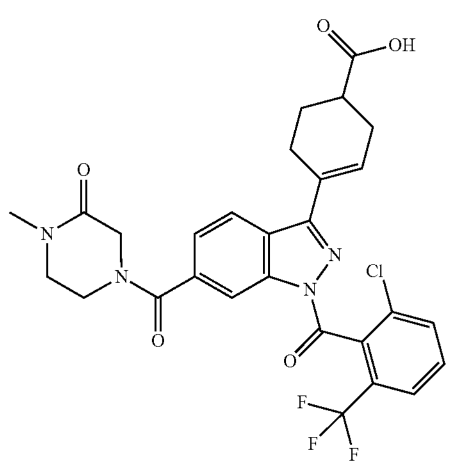 [SMILES: CN1CCN(C(=O)c2ccc3c(C4=CCC(C(=O)O)CC4)nn(C(=O)c4c(Cl)cccc4C(F)(F)F)c3c2)CC1=O] | 589 |

TABLE 3-continued

| | IUPAC Name | Structure | LCMS [M + H]+ Found |
|---|---|---|---|
| 4O | 4-(1-(2-chloro-6-(trifluoromethyl)benzoyl)-6-((S)-3-methylmorpholine-4-carbonyl)-1H-indazol-3-yl)cyclohex-3-enecarboxylic acid | 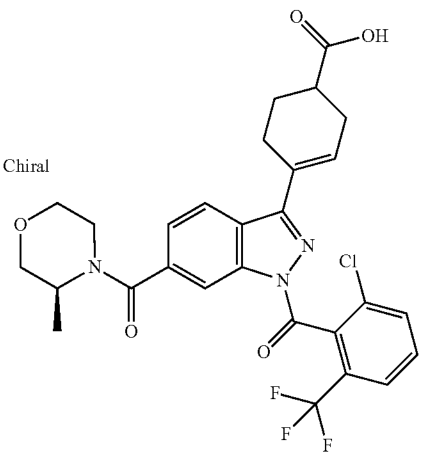 [SMILES: "Chiral" ; C[C@H]1COCCN1C(=O)c1ccc2c(C3=CCC(C(=O)O)CC3)nn(C(=O)c3c(Cl)cccc3C(F)(F)F)c2c1] | 576 |
| 4P | 4-(1-(2-chloro-6-(trifluoromethyl)benzoyl)-6-(methyl(tetrahydro-2H-pyran-4-yl)carbamoyl)-1H-indazol-3-yl)cyclohex-3-enecarboxylic acid | 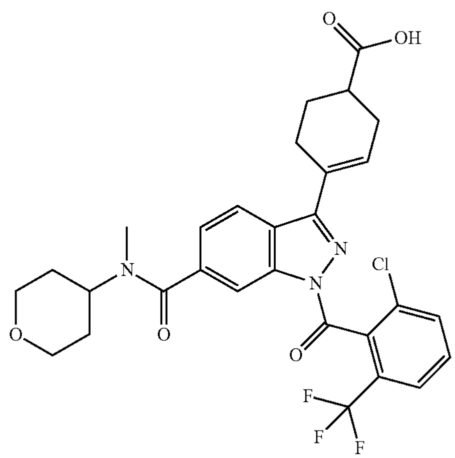 [SMILES: CN(C(=O)c1ccc2c(C3=CCC(C(=O)O)CC3)nn(C(=O)c3c(Cl)cccc3C(F)(F)F)c2c1)C1CCOCC1] | 590 |
| 4Q | 4-(1-(2-chloro-6-(trifluoromethyl)benzoyl)-6-((R)-3-methylmorpholine-4-carbonyl)-1H-indazol-3-yl)cyclohex-3-enecarboxylic acid | 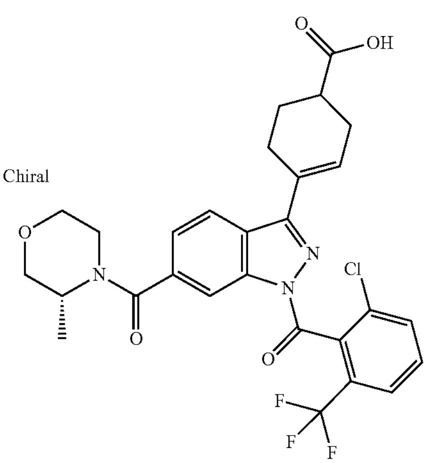 [SMILES: C[C@@H]1COCCN1C(=O)c1ccc2c(C3=CCC(C(=O)O)CC3)nn(C(=O)c3c(Cl)cccc3C(F)(F)F)c2c1] | 576 |

TABLE 3-continued

| | IUPAC Name | Structure | LCMS [M + H]+ Found |
|---|---|---|---|
| 4R | 4-(1-(2-chloro-6-(trifluoromethyl)benzoyl)-6-((S)-2-methylmorpholine-4-carbonyl)-1H-indazol-3-yl)cyclohex-3-enecarboxylic acid | Chiral | 576 |
| 4S | 4-(1-(2-chloro-6-(trifluoromethyl)benzoyl)-6-((2-hydroxyethyl)(methyl)carbamoyl)-1H-indazol-3-yl)cyclohex-3-enecarboxylic acid | 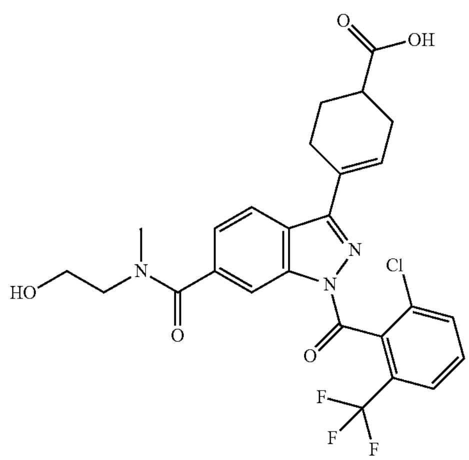 [SMILES: CN(CCO)C(=O)c1ccc2c(C3=CCC(C(=O)O)CC3)nn(C(=O)c3c(Cl)cccc3C(F)(F)F)c2c1] | 550 |
| 4T | 4-(1-(2-chloro-6-(trifluoromethyl)benzoyl)-6-(isopropylcarbamoyl)-1H-indazol-3-yl)cyclohex-3-enecarboxylic acid | 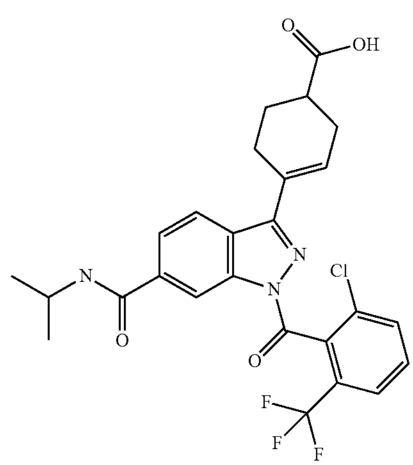 [SMILES: CC(C)NC(=O)c1ccc2c(C3=CCC(C(=O)O)CC3)nn(C(=O)c3c(Cl)cccc3C(F)(F)F)c2c1] | 534 |

TABLE 3-continued

| | IUPAC Name | Structure | LCMS [M + H]+ Found |
|---|---|---|---|
| 4U | 4-(1-(2-chloro-6-(trifluoromethyl)benzoyl)-6-(isopropyl(methyl)carbamoyl)-1H-indazol-3-yl)cyclohex-3-enecarboxylic acid | 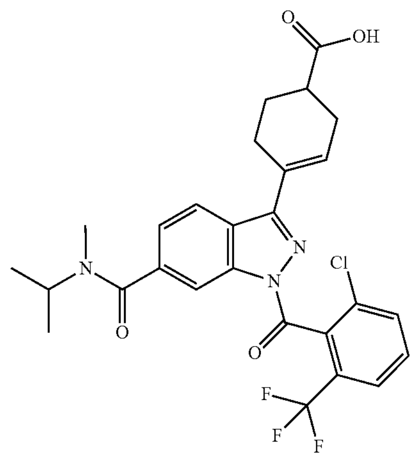 [SMILES: CC(C)N(C)C(=O)c1ccc2c(C3=CCC(C(=O)O)CC3)nn(C(=O)c3c(Cl)cccc3C(F)(F)F)c2c1] | 548 |
| 4V | 4-(1-(2-chloro-6-(trifluoromethyl)benzoyl)-6-((2-methoxyethyl)(methyl)carbamoyl)-1H-indazol-3-yl)cyclohex-3-enecarboxylic acid | 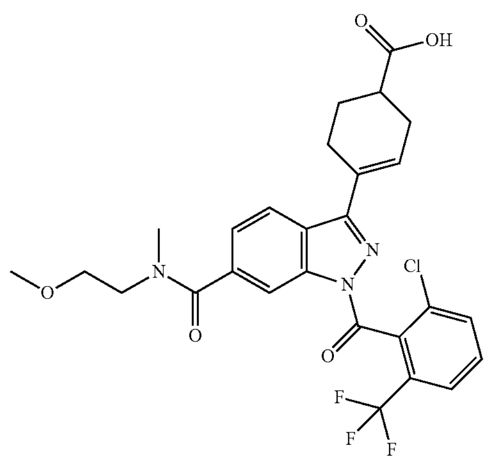 [SMILES: COCCN(C)C(=O)c1ccc2c(C3=CCC(C(=O)O)CC3)nn(C(=O)c3c(Cl)cccc3C(F)(F)F)c2c1] | 564 |
| 4W | 4-(1-(2-chloro-6-(trifluoromethyl)benzoyl)-6-(3-hydroxyazetidine-1-carbonyl)-1H-indazol-3-yl)cyclohex-3-enecarboxylic acid | 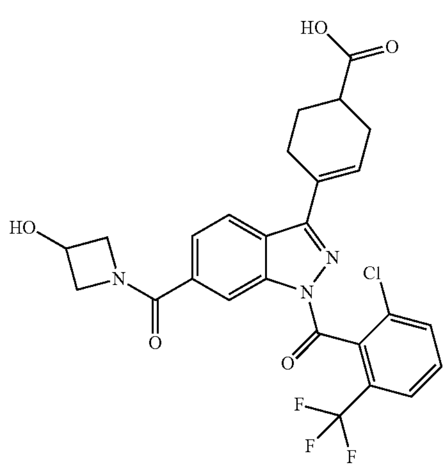 [SMILES: O=C(O)C1CC=C(c2nn(C(=O)c3c(Cl)cccc3C(F)(F)F)c3cc(C(=O)N4CC(O)C4)ccc23)CC1] | 548 |

TABLE 3-continued

| | IUPAC Name | Structure | LCMS [M + H]+ Found |
|---|---|---|---|
| 4X | 4-(1-(2-chloro-6-(trifluoromethyl)benzoyl)-6-(3-fluoroazetidine-1-carbonyl)-1H-indazol-3-yl)cyclohex-3-enecarboxylic acid | 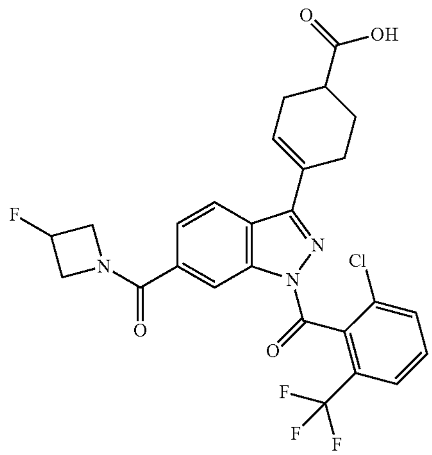 [SMILES: O=C(O)C1CC=C(c2nn(C(=O)c3c(Cl)cccc3C(F)(F)F)c3cc(C(=O)N4CC(F)C4)ccc23)CC1] | 550 |
| 4Y | 4-(1-(2-chloro-6-(trifluoromethyl)benzoyl)-6-(piperidine-1-carbonyl)-1H-indazol-3-yl)cyclohex-3-enecarboxylic acid | 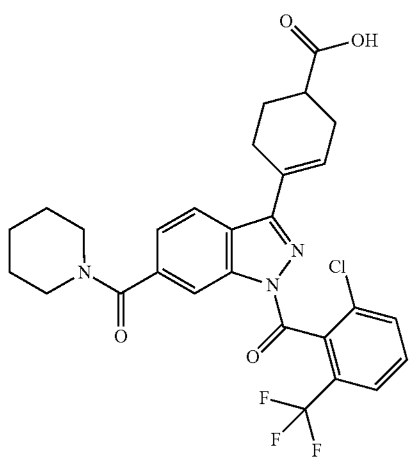 [SMILES: O=C(O)C1CC=C(c2nn(C(=O)c3c(Cl)cccc3C(F)(F)F)c3cc(C(=O)N4CCCCC4)ccc23)CC1] | 560 |
| 4Z | 4-(1-(2-chloro-6-(trifluoromethyl)benzoyl)-6-(((1-hydroxy-3-(methylamino)propan-2-yl)oxy)carbonyl)-1H-indazol-3-yl)cyclohex-3-enecarboxylic acid | 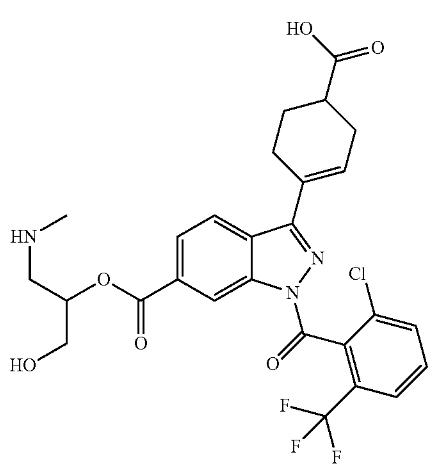 [SMILES: CNCC(CO)OC(=O)c1ccc2c(C3=CCC(C(=O)O)CC3)nn(C(=O)c3c(Cl)cccc3C(F)(F)F)c2c1] | 580 |

TABLE 3-continued

| | IUPAC Name | Structure | LCMS [M + H]+ Found |
|---|---|---|---|
| 4AA | Enantiomer 1: 4-(1-(2-chloro-6-(trifluoromethyl)benzoyl)-6-((S)-3-methoxypyrrolidine-1-carbonyl)-1H-indazol-3-yl)cyclohex-3-enecarboxylic acid | 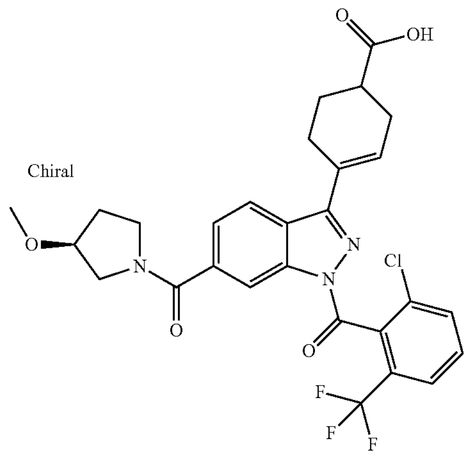 | 576 |
| 4AB | Enantiomer 2: 4-(1-(2-chloro-6-(trifluoromethyl)benzoyl)-6-((R)-3-methoxypyrrolidine-1-carbonyl)-1H-indazol-3-yl)cyclohex-3-enecarboxylic acid | 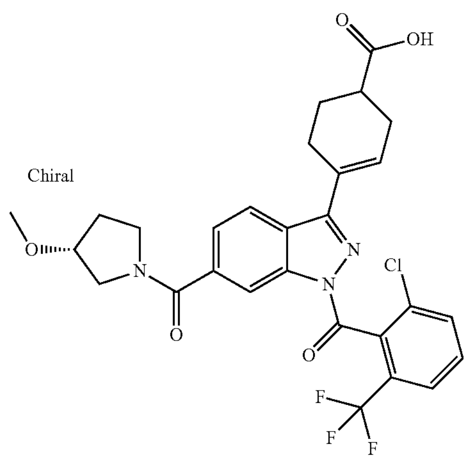 | 576 |

Example 5A

Preparation of 4-(1-(2-chloro-6-(trifluoromethyl)benzoyl)-4-fluoro-1H-indol-3-yl)cyclohex-3-enecarboxylic acid -continued

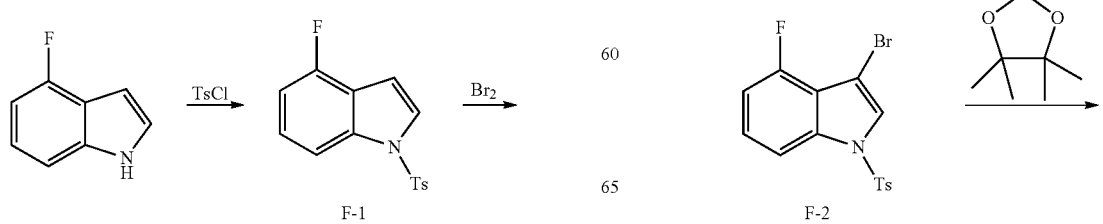

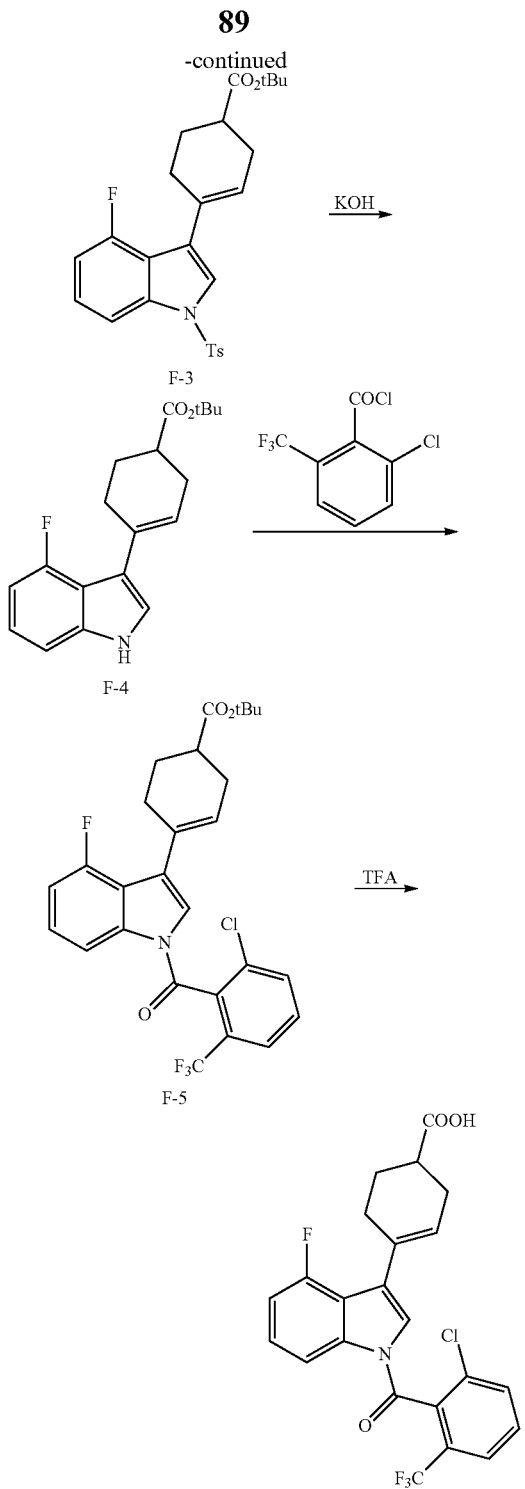

Step 1: Preparation of 4-fluoro-1-tosyl-1H-indole (F-1)

To a flask was added 4-fluoro-1H-indole (1000 mg, 7.40 mmol), sodium hydride (326 mg, 8.14 mmol), and DMF (14.8 mL). The solution was allowed to stir at room temperature for 30 min. 4-methylbenzene-1-sulfonyl chloride (2116 mg, 11.10 mmol) was then added to the flask and the resulting solution was allowed to stir for 3 hours. The mixture was diluted with ethyl acetate, washed 2× with aqueous sodium hydrogen carbonate and 1× with brine. The combined aqueous layer was back extracted once with ethyl acetate, combined organic layers were dried with $Na_2SO_4$, filtered and the solvent was evaporated under reduced pressure. The residue was purified by flash chromatography (EtOAc/Hexane 0-75%) to give the desired product as a colorless solid. (1.76 g, 82%) LCMS (ESI) calc'd for $C_{15}H_{12}FNO_2S$ [M+H]$^+$: 290. found: 290.

Step 2: Preparation of 3-bromo-4-fluoro-1-tosyl-1H-indole (F-2)

To a flask was added 4-fluoro-1-tosyl-1H-indole (F-1) (784 mg, 2.71 mmol) and DCM (8 mL) and the reaction was cooled to 0° C. A solution of bromine (0.154 mL, 2.98 mmol) in DCM (8 mL) was added dropwise and the resulting solution was allowed to stir for 1 hour. The mixture was diluted with ethyl acetate, washed 2× with aqueous sodium hydrogen carbonate and 1× with brine. The combined aqueous layer was back extracted once with ethyl acetate, and the combined organics were dried over Na2SO4, filtered and the solvent was evaporated under reduced pressure. The residue was purified by flash chromatography (EtOAc/Hexane 0-75%) to give the desired product as a colorless solid. (358 mg, 35%) LCMS (ESI) calc'd for $C_{15}H_{11}BrFNO_2S$ [M+H]$^+$: 367.9, found: 367.9.

Step 3: Preparation of tert-butyl 4-(4-fluoro-1-tosyl-1H-indol-3-yl)cyclohex-3-ene carboxylate (F-3)

To a flask was added 3-bromo-4-fluoro-1-tosyl-1H-indole (F-2) (471 mg, 1.279 mmol), (2-dicyclohexylphosphino-2',4',6'-trissopropyl-1,1'-biphenyl)[2-(2-aminoethyl)phenyl] palladium (II) chloride (94 mg, 0.128 mmol), THF (6396 μl) and the vial was thoroughly degassed with argon. Potassium phosphate tribasic (2558 μl, 2.56 mmol) was added and the reaction was heated to 80° C. and allowed to stir overnight. The mixture was cooled, diluted with ethyl acetate, washed 2× with aqueous sodium hydrogen carbonate and 1× with brine. The combined aqueous layer was back extracted once with ethyl acetate, and the combined organics were dried over Na2SO4, filtered and the solvent was evaporated under reduced pressure. The residue was purified by flash chromatography (EtOAc/Hexane 10-75%) to give the desired product as a colorless solid. LCMS (ESI) calc'd for $C_{26}H_{28}FNO_4S$ [M−tBu]$^+$: 414. found: 414.

Step 4: Preparation of tert-butyl 4-(4-fluoro-1H-indol-3-yl)cyclohex-3-enecarboxylate (F-4)

To a flask was added tert-butyl 4-(4-fluoro-1-tosyl-1H-indol-3-yl)cyclohex-3-enecarboxylate (F-3) (550 mg, 1.171 mmol), THF (3904 μl), ethanol (7809 μl) and KOH (657 mg, 11.71 mmol) and the reaction was allowed to stir at room temperature for 2 hours. The reaction mixture was diluted with methanol and filtered. The resulting solution was concentrated and the residue was diluted with ethyl acetate, washed 2× with aqueous sodium hydrogen carbonate and 1× with brine. The combined aqueous layer was back extracted once with ethyl acetate, and the combined organics were dried with Na2SO4, filtered and the solvent was evaporated under reduced pressure. The residue was purified by flash chromatography (EtOAc/Hexane 10-75%) to give the desired product as a colorless solid. (217 mg, 53% over two steps) LCMS (ESI) calc'd for $C_{19}H_{22}FNO_2$ [M−tBu]$^+$: 260, found: 260.

Step 5: Preparation of tert-butyl 4-(1-(2-chloro-6-(trifluoromethyl)benzoyl)-4-fluoro-1H-indol-3-yl)cyclohex-3-enecarboxylate (F-5)

To a vial was added tert-butyl 4-(4-fluoro-1H-indol-3-yl)cyclohex-3-enecarboxylate (F-4) (58 mg, 0.184 mmol), and DMF (1839 µl), followed by sodium hydride (8.83 mg, 0.221 mmol) portionwise. The reaction was stirred for 30 min at room temperature. 2-chloro-6-(trifluoromethyl)benzoyl chloride (53.6 mg, 0.221 mmol) was added dropwise to the solution and the resulting mixture was stirred for an additional hour. The mixture was diluted with ethyl acetate, washed 2× with aqueous sodium hydrogen carbonate and 1× with brine. The combined aqueous layer was back extracted once with ethyl acetate, and the combined organics were dried with Na2SO4, filtered, and the solvent was evaporated under reduced pressure. The residue was purified by flash chromatography (EtOAc/Hexane 10-75%) to give the desired product. (93 mg, 98%) LCMS (ESI) calc'd for $C_{27}H_{24}ClF_4NO_3$ [M−tBu]$^+$: 466. found: 466.

Step 6: Preparation of 4-(1-(2-chloro-6-(trifluoromethyl)benzoyl)-4-fluoro-1H-indol-3-yl)cyclohex-3-enecarboxylic acid (5A)

To a vial was added tert-butyl 4-(1-(2-chloro-6-(trifluoromethyl)benzoyl)-4-fluoro-1H-indol-3-yl)cyclohex-3-enecarboxylate (F-5) (90 mg, 0.172 mmol), DCM (1724 µl), and TFA (332 µl, 4.31 mmol); the solution was stirred at room temperature for 2 hours. The reaction was concentrated and the residue was purified by Prep-HPLC (Acetonitrile/Water+0.10% TFA 60-95%) to obtain the desired product as a colorless solid. (41 mg, 51%) LCMS (ESI) calc'd for $C_{23}H_{16}ClF_4NO_3$ [M+H]$^+$: 466, found: 466. $^1$H NMR (600 MHz, DMSO) δ 8.31 (d, J=8.2, 1H), 8.00 (d, J=8.2, 1H), 7.96 (d, J=8.1, 1H), 7.84 (t, J=8.1, 1H), 7.49-7.41 (m, 1H), 7.23-7.16 (m, 1H), 7.04 (d, J=3.6, 1H), 5.90 (s, 1H), 2.36-2.13 (m, 5H), 2.00-1.91 (m, 1H), 1.65-1.52 (m, 1H).

Example 6A and 6B

Preparation of 4-(1-(2-chloro-6-(trifluoromethyl)benzoyl)-4-fluoro-1H-indazol-3-yl)-2-hydroxycyclohex-3-enecarboxylic acid (6A) and 4-(1-(2-chloro-6-(trifluoromethyl)benzoyl)-4-fluoro-1H-indazol-3-yl)-6-hydroxycyclohex-3-enecarboxylic acid (6B)

Scheme G

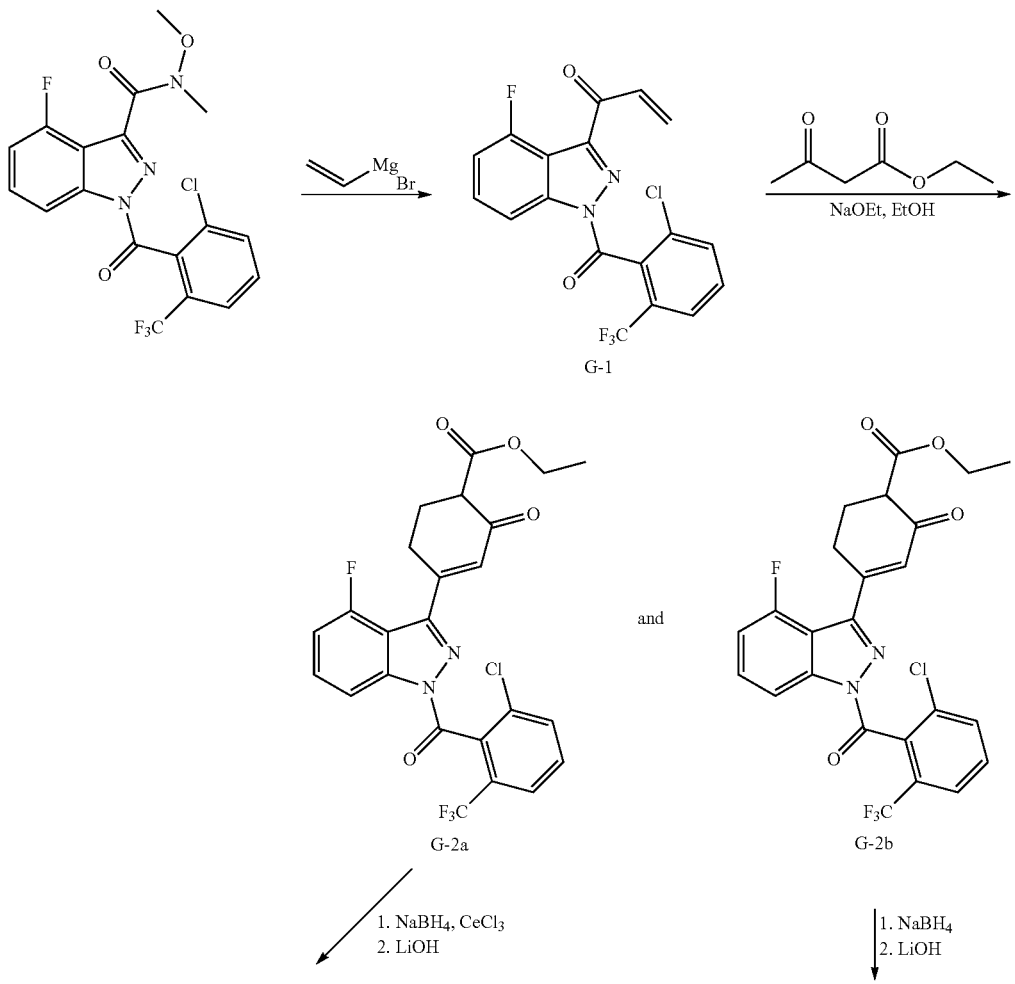

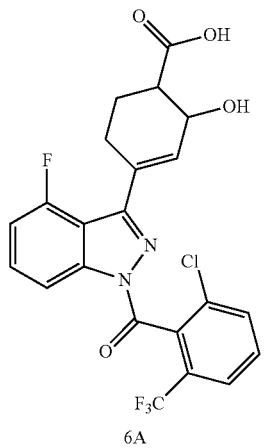

6A

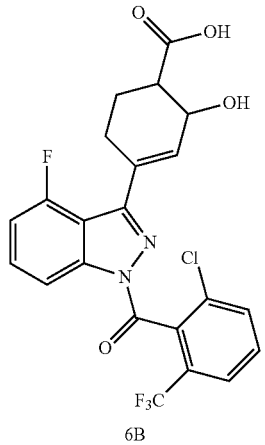

6B

Step 1. Preparation of 1-(1-(2-chloro-6-(trifluoromethyl)benzoyl)-4-fluoro-1H-indazol-3-yl)prop-2-en-1-one (G-1)

To a solution of 1-(2-chloro-6-(trifluoromethyl)benzoyl)-4-fluoro-N-methoxy-N-methyl-1H-indazole-3-carboxamide (3.2 g, 7.44 mmol) in THF (32 mL) was added vinylmagnesium bromide (26 mL, 26 mmol) under $N_2$ at 10-20° C. After 15-20 mins, the mixture was poured into a mixture of ice and aqueous HCl. Extracted with DCM (500 mL×5) and the combined organic phase was washed with brine and dried over $Na_2SO_4$. The crude product was purified with column chromatography (PE:DCM=3:1) to give the title compound (2.5 g, yield: 74%) as a white solid. LCMS (ESI): calc'd for $C_{18}H_9ClF_4N_2O_2$ $[M+H]^+$: 397, found: 397.

Step 2. Preparation of ethyl 4-(1-(2-chloro-6-(trifluoromethyl)benzoyl)-4-fluoro-1H-indazol-3-yl)-2-oxocyclohex-3-enecarboxylate (G-2a) and ethyl 4-(1-(2-chloro-6-(trifluoromethyl)benzoyl)-4-fluoro-1H-indazol-3-yl)-6-oxocyclohex-3-enecarboxylate (G-2b)

To a solution of 1-(1-(2-chloro-6-(trifluoromethyl)benzoyl)-4-fluoro-1H-indazol-3-yl)prop-2-en-1-one (G-1) (2.35 g, 6.43 mmol) in EtOH (306 mL) was added ethyl 3-oxobutanoate (837 mg, 6.43 mmol) and EtONa (437 mg, 6.43 mmol) while stirring under $N_2$. The reaction was heated to 80° C. for 10 hours, and then concentrated to remove EtOH. The residue was diluted with $H_2O$ and extracted with EtOAc (500 mL×5). The combined organic phase was washed with brine and dried over $Na_2SO_4$. The crude product was purified by column chromatography (PE:EA=50:1, 30:1 to 10:1) to give the title compound (G-2a) (600 mg, yield: 18%) as colorless oil and (G-2b) (300 mg, yield: 9%) as a white solid. LCMS (ESI): calc'd for $C_{24}H_{17}ClF_4N_2O_4$ $[M+H]^+$: 509, found: 509.

Step 3. Preparation of ethyl 4-(1-(2-chloro-6-(trifluoromethyl)benzoyl)-4-fluoro-1H-indazol-3-yl)-2-hydroxycyclohex-3-enecarboxylate (G-3)

To a solution of ethyl 4-(1-(2-chloro-6-(trifluoromethyl)benzoyl)-4-fluoro-1H-indazol-3-yl)-2-oxocyclohex-3-enecarboxylate (G-2) (285 mg, 0.56 mmol) in MeOH (5 mL) was added $CeCl_3.7H_2O$ (1.0 g, 2.80 mmol) and $NaBH_4$ (66 mg, 1.75 mmol) at 0° C. under $N_2$. The mixture was stirred for 0.5 h and then quenched with $H_2O$, and extracted with EtOAc (50 mL×5). The combined organics were washed with brine and dried over $Na_2SO_4$. The crude product was purified by prep-TLC (PE:EA=3:1) to give the title compound (260 mg, yield: 90%) as a colorless oil. LCMS (ESI): calc'd for $C_{24}H_{19}ClF_4N_2O_4$ $[M+H]^+$: 511, found: 493.

Step 4. Preparation of 4-(1-(2-chloro-6-(trifluoromethyl)benzoyl)-4-fluoro-1H-indazol-3-yl)-2-hydroxycyclohex-3-enecarboxylic acid (6A)

To a solution of ethyl 4-(1-(2-chloro-6-(trifluoromethyl)benzoyl)-4-fluoro-1H-indazol-3-yl)-2-hydroxycyclohex-3-enecarboxylate (G-3) (60 mg, 0.12 mmol) in THF/$H_2O$ (3 mL/1 mL) was added LiOH.$H_2O$ (25 mg, 0.59 mmol) under $N_2$. The reaction was stirred at 20° C. for 10 hours and was then quenched with $H_2O$ and extracted with EtOAc (50 mL×3). The combined organics were washed with brine and dried over $Na_2SO_4$. The product was purified to give the title compound as a white solid (40 mg, yield: 71%) with prep-TLC (PE:EA=1:1). LCMS (ESI): calc'd for $C_{22}H_{15}ClF_4N_2O_4$ $[M+H]^+$: 483, found: 465; $^1$H-NMR (400 MHz, Methanol-$d_4$) δ 8.38 (1H, d, J=8.0 Hz), 7.72~7.85 (4H, m), 7.23~7.28 (1H, m), 6.70 (0.6H, s), 6.60 (0.4H, s), 4.59~4.62 (1H, m), 1.81~2.66 (5H, m).

Step 5. Preparation of 4-(1-(2-chloro-6-(trifluoromethyl)benzoyl)-4-fluoro-1H-indazol-3-yl)-6-hydroxycyclohex-3-enecarboxylic acid (6B)

Preparation from the other regioisomer G-2b was similar to the preparation of 6A, and can be achieved by those of ordinary skill in the art of organic synthesis in light of the present disclosure.

The following example shown in TABLE 4 was prepared following similar procedures described for Example 6A and 6B in Scheme G, which can be achieved by those of ordinary skill in the art of organic synthesis in light of the present disclosure.

TABLE 4

| | Chemical Name | Structure | LCMS [M + H]+ Found |
|---|---|---|---|
| 6C | 4-(1-(2-chloro-6-(trifluoromethyl)benzoyl)-4-fluoro-1H-indazol-3-yl)-2-hydroxy-6-methylcyclohex-3-enecarboxylic acid | 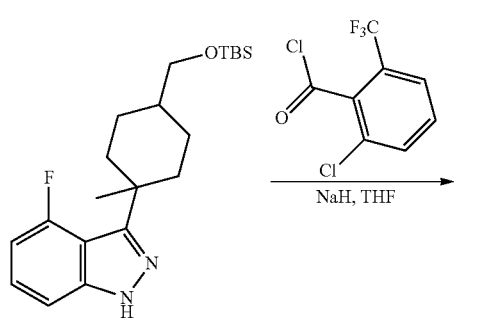 | 479 |

Example 7A, 7B and 7C

Preparation of 4-(1-(2-chloro-6-(trifluoromethyl)benzoyl)-4-fluoro-1H-indazol-3-yl)-4-methylcyclohexanecarboxylic acid (7A)

Scheme H

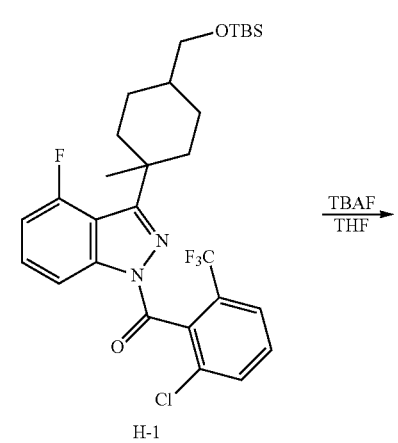

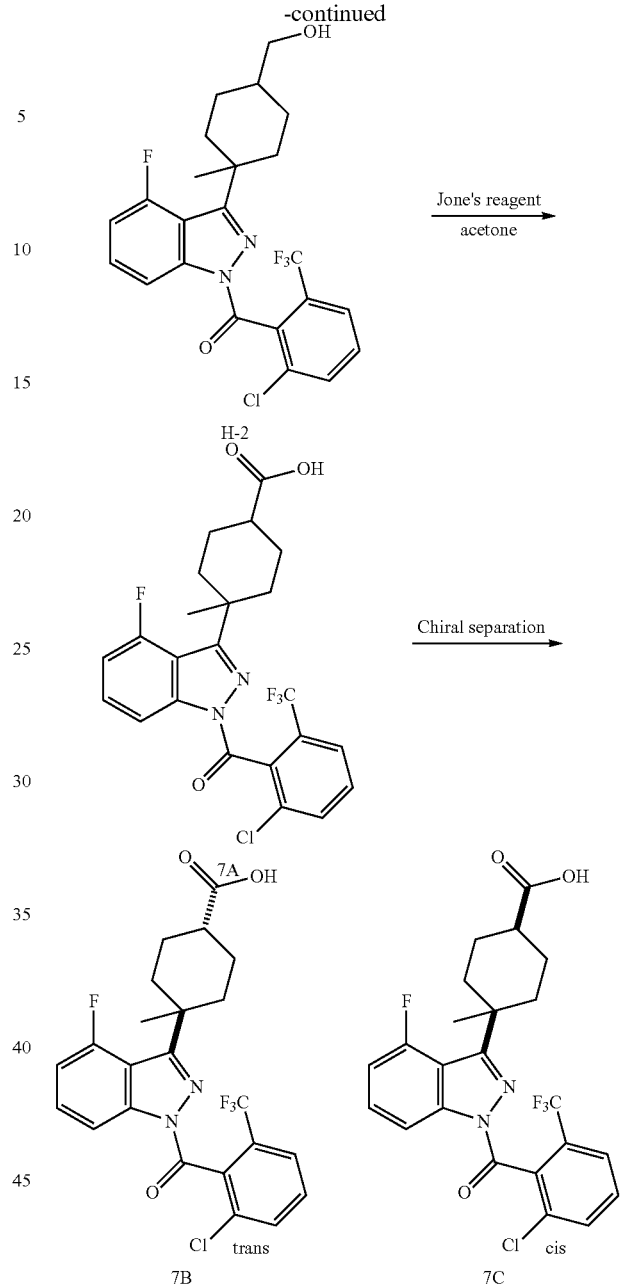

Step 1. Preparation of (3-(4-(((tert-butyldimethylsilyl)oxy)methyl)-1-methylcyclohexyl)-4-fluoro-1H-indazol-1-yl)(2-chloro-6-(trifluoromethyl)phenyl)methanone (H-1)

To a solution of compound 3-(4-(((tert-butyldimethylsilyl)oxy)methyl)-1-methylcyclohexyl)-4-fluoro-1H-indazole (300 mg, 0.8 mmol) in 10 mL of THF, was added NaH (39 mg, 1.0 mmol, 60% in mineral oil) at 0° C. The mixture was stirred at 15° C. for 30 min. 2-chloro-6-(trifluoromethyl)benzoyl chloride (212 mg, 0.9 mmol) in 5 mL of THF was added dropwise at 0° C. The mixture was stirred at 15° C. for 2 h, poured into water (150 mL) and extracted with EtOAc (100 mL×3). The combined organic layer was washed with brine (100 mL×2), dried over anhydrous Na2SO4, filtered and concentrated in vacuo. The crude was purified by column chromatography on silica gel (PE:EtOAc=100:1 to PE:EtOAc=20:1) to afford the title compound (400 mg, 86.4%) as a yellow solid. LCMS (ESI): calc'd for C29H35ClF4N2O2Si [M+H]+: 583, found: 583.

Step 2. Preparation of (2-chloro-6-(trifluoromethyl) phenyl)(4-fluoro-3-(4-(hydroxyl methyl)-1-methyl-cyclohexyl)-1H-indazol-1-yl)methanone (H-2)

To a solution of compound (3-(4-(((tert-butyldimethylsilyl)oxy)methyl)-1-methylcyclohexyl)-4-fluoro-1H-indazol-1-yl)(2-chloro-6-(trifluoromethyl)phenyl)methanone (H-1) (360 mg, 0.6 mmol) in 10 mL of THF was added TBAF (323 mg, 1.2 mmol) dropwise, while cooling the reaction to 0° C. The mixture was stirred at 15° C. for 24 h. The resulting mixture was poured into 100 mL of water and extracted with EtOAc (200 mL×3). The combined organics were washed with brine (100 mL×2), dried over anhydrous $Na_2SO_4$, filtered and concentrated in vacuo. The crude was purified by column chromatography on silica gel (PE:EtOAc=100:1 to PE:EtOAc=1:1) to afford the title compound (250 mg, 86%) as a yellow oil. LCMS (ESI): calc'd for $C_{23}H_{21}ClF_4N_2O_2$ [M+H]$^+$: 469, found: 469.

Step 3. Preparation of 4-(1-(2-chloro-6-(trifluoromethyl)benzoyl)-4-fluoro-1H-indazol-3-yl)-4-methyl-cyclohexanecarboxylic acid (7A)

To a solution of (2-chloro-6-(trifluoromethyl)phenyl)(4-fluoro-3-(4-(hydroxymethyl)-1-methylcyclohexyl)-1H-indazol-1-yl)methanone (H-2) (100 mg, 0.2 mmol) in acetone (10 mL) was added dropwise 0.2 mL of Jones reagent, while cooling to 0° C. The mixture was stirred at 15° C. for 20 min. The resulting mixture was quenched with 10 mL of propan-2-ol, diluted with 100 mL of water and extracted with EtOAc (100 mL×3). The organic layer was washed with brine (100 mL×2), dried over anhydrous $Na_2SO_4$, filtered and concentrated in vacuo. The crude was purified by column chromatography on silica gel (PE:EtOAc=100:1 to PE:EtOAc=5:1) to afford the title compound (76 mg, 75%) as a white solid. LCMS (ESI): calc'd for $C_{23}H_{19}ClF_4N_2O_3$ [M+H]$^+$: 483, found: 483. $^1$H NMR (400 MHz, CDCl$_3$) δ 1.27-1.47 (7H, d), 1.65 (2H, dd, J=19.32, 15.31 Hz), 2.21-2.37 (2H, m), 2.42 (1H, d, J=13.56 Hz), 7.11 (1H, dd, J=10.80, 8.28 Hz), 7.51-7.68 (4H, m), 8.42 (1H, d, J=8.04 Hz).

Further separation by SFC afforded two isomers: (trans)-4-(1-(2-chloro-6-(trifluoromethyl)benzoyl)-4-fluoro-1H-indazol-3-yl)-4-methyl cyclohexanecarboxylic acid (7B) and (cis)-4-(1-(2-chloro-6-(trifluoromethyl) benzoyl)-4-fluoro-1H-indazol-3-yl)-4-methylcyclohexanecarboxylic acid (7C)

Example 8A and 8B

Preparation of (trans)-4-(1-(2-chloro-6-(trifluoromethyl)benzoyl)-4-fluoro-1H-indazol-3-yl)cyclohexanecarboxylic acid (8A) and (cis)-4-(1-(2-chloro-6-(trifluoromethyl)benzoyl)-4-fluoro-1H-indazol-3-yl)cyclohexanecarboxylic acid (8B)

Scheme I

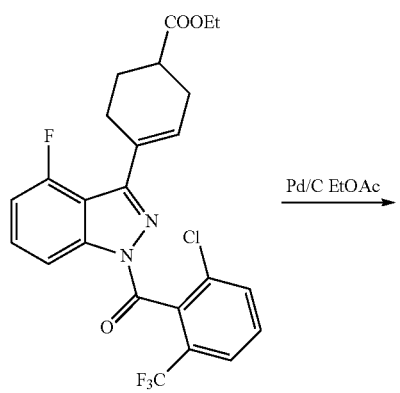

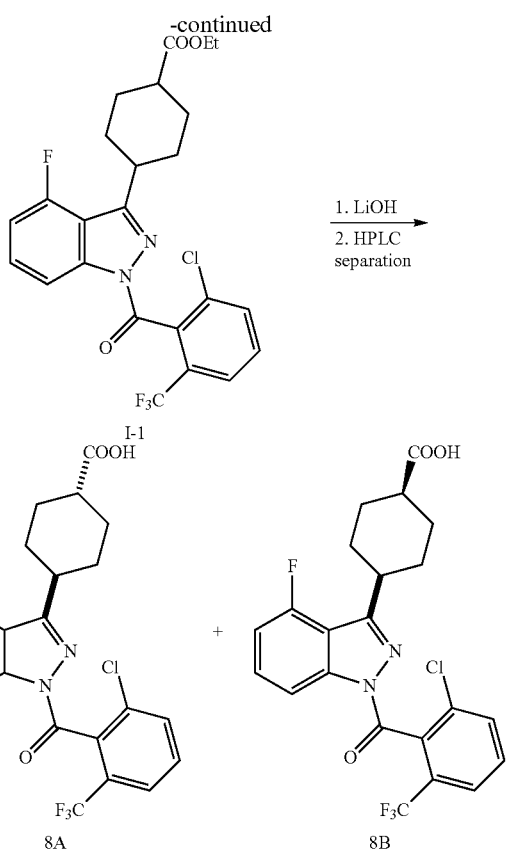

Step 1. Preparation of (Racemic) ethyl 4-(1-(2-chloro-6-(trifluoromethyl)benzoyl)-4-fluoro-1H-indazol-3-yl)cyclohexanecarboxylate (I-1)

To a solution of (Racemic) ethyl 4-(1-(2-chloro-6-(trifluoromethyl)benzoyl)-4-fluoro-1H-indazol-3-yl)cyclohex-3-enecarboxylate (100 mg, 0.2 mmol) in ethyl acetate (20 mL) was added 10% Pd/C (20 mg) while stirring under nitrogen. The suspension was degassed and purged with H$_2$ several times, and then stirred under H$_2$ (balloon) at 40° C. for 4 h. The resulting mixture was filtered over Celite, rinsing with ethyl acetate (50 mL). The combined organic layers were concentrated in vacuo to dryness to give the crude product, which was further purified by column chromatography on silica gel (PE:EtOAc=10:1) to afford the title compound (60 mg, 60%) as a colorless oil. LCMS (ESI) calc'd for $C_{24}H_{21}ClF_4N_2O_3$ [M+H]$^+$: 497, found: 497.

Step 2. Preparation of (trans)-4-(1-(2-chloro-6-(trifluoromethyl)benzoyl)-4-fluoro-1H-indazol-3-yl) cyclohexanecarboxylic acid (8A) and (cis)-4-(1-(2-chloro-6-(trifluoromethyl)benzoyl)-4-fluoro-1H-indazol-3-yl)cyclohexanecarboxylic acid (8B)

To a mixture of (Racemic) ethyl 4-(1-(2-chloro-6-(trifluoromethyl)benzoyl)-4-fluoro-1H-indazol-3-yl)cyclohexanecarboxylate (I-1) (150 mg, 0.30 mmol) in EtOH (5 mL) was added LiOH (22 mg, 0.91 mmol). The reaction was stirred at 20° C. for 4 h. The resulting mixture was concentrated in vacuo and water (15 mL) was added. The aqueous solution was washed with ethyl acetate (15 mL), and acidified with 2 M HCl to pH=2. The precipitate was collected by filtration to give the crude product (70 mg, cis: trans=3:1) as a white solid, which was separated by prep-HPLC (acetonitrile+0.75% trifluoroacetic acid in water) to afford two isomers:

(trans)-4-(1-(2-chloro-6-(trifluoromethyl)benzoyl)-4-fluoro-1H-indazol-3-yl)cyclohexanecarboxylic acid (8A) (2 mg). LCMS (ESI) calc'd for $C_{22}H_{17}ClF_4N_2O_3$ [M+H]$^+$: 469, found: 469. $^1$H NMR (400 MHz CDCl$_3$) δ 8.35 (1 H, d, J=8.53 Hz), 7.67-7.70 (2 H, m), 7.55-7.60 (2H, m), 7.06-7.11 (1 H, m), 3.04-3.09 (1H, m), 2.35-2.40 (1H, t, J=11.2 Hz), 2.10 (4 H, br s.), 1.51-1.64 (4 H, m).

(cis)-4-(1-(2-chloro-6-(trifluoromethyl)benzoyl)-4-fluoro-1H-indazol-3-yl)cyclohexanecarboxylic acid (8B) (6 mg). LCMS (ESI) calc'd for $C_{22}H_{17}ClF_4N_2O_3$ [M+H]$^+$: 469, found: 469. $^1$H NMR (400 MHz, CDCl$_3$) δ 8.35 (1 H, d, J=8.28 Hz), 7.37-7.74 (4 H, m), 6.92-7.13 (1H, m), 3.37 (1H, br.s.), 2.52 (1H, br.s.), 1.76-2.00 (6H, m), 1.66 (2H, d, J=4.52 Hz).

Example 9A and 9B

Preparation of (trans)-4-(1-(2-chloro-6-(trifluoromethyl)benzoyl)-4-fluoro-1H-indazol-3-yl)-1-methylcyclohexanecarboxylic acid (9A) and (cis)-4-(1-(2-chloro-6-(trifluoromethyl)benzoyl)-4-fluoro-1H-indazol-3-yl)-1-methylcyclohexanecarboxylic acid (9B)

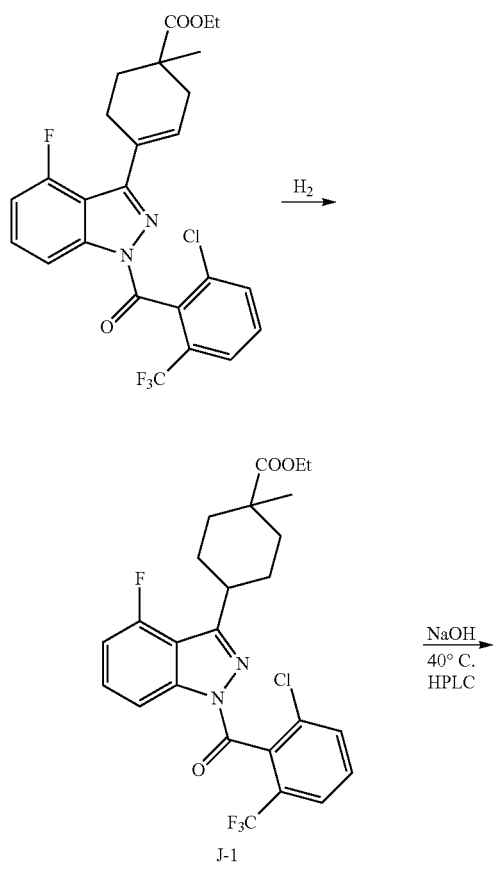

Scheme J

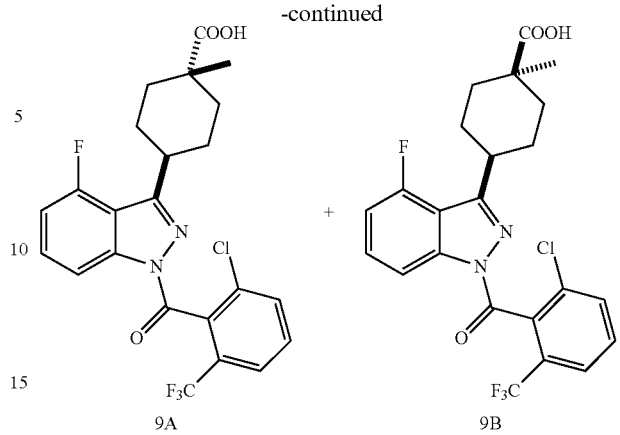

Step 1: Preparation of ethyl 4-(1-(2-chloro-6-(trifluoromethyl)benzoyl)-4-fluoro-1H-indazol-3-yl)-1-methylcyclohexanecarboxylate (J-1)

To a cis/trans mixture of ethyl 4-(1-(2-chloro-6-(trifluoromethyl)benzoyl)-4-fluoro-1H-indazol-3-yl)-1-methylcyclohex-3-enecarboxylate (300 mg, 0.606 mmol) in EtOAc (30 mL) was added Pd/C (6.5 mg, 0.061 mmol) while stirring under nitrogen. The suspension was degassed in vacuo and purged with H$_2$ several times, and then stirred under H$_2$ (balloon) at 40° C. for 4 h. The resulting mixture was filtered over a Celite pad, rinsing with ethyl acetate (50 mL). The combined filtrates were concentrated in vacuo to dryness. The crude product was purified by column chromatography on silica gel (ethyl acetate/petroleum ether=1/10) to afford the title compound (150 mg, yield: 47.3%) as a colorless oil. LCMS (ESI) calc'd for $C_{25}H_{23}ClF_4N_2O_3$ [M+H]$^+$: 511, found: 511.

Step 2: Preparation of (trans)-4-(1-(2-chloro-6-(trifluoromethyl)benzoyl)-4-fluoro-1H-indazol-3-yl)-1-methylcyclohexanecarboxylic acid (9A) and (cis)-4-(1-(2-chloro-6-(trifluoromethyl)benzoyl)-4-fluoro-1H-indazol-3-yl)-1-methylcyclohexanecarboxylic acid (9B)

To a mixture of ethyl 4-(1-(2-chloro-6-(trifluoromethyl)benzoyl)-4-fluoro-1H-indazol-3-yl)-1-methylcyclohexanecarboxylate (J-1) (100 mg, 0.196 mmol) in EtOH (10 mL) was added NaOH (24 mg, 0.59 mmol) and the reaction was stirred at 40° C. for 12 h. The resulting mixture was concentrated in vacuo, diluted with water (10 mL), and washed with ethyl acetate (10 mL×2). The aqueous layer was acidified with 2 M HCl to pH=2. The precipitate was collected by filtration and purified by preparative HPLC (acetonitrile+0.75% trifluoroacetic acid in water) to give two separate isomers:

(trans)-4-(1-(2-chloro-6-(trifluoromethyl)benzoyl)-4-fluoro-1H-indazol-3-yl)-1-methylcyclohexanecarboxylic acid (9A): 5 mg, LCMS (ESI) calc'd for $C_{23}H_{19}ClF_4N_2O_3$ [M+H]$^+$: 483, found: 483. $^1$H NMR (400 MHz, CDCl$_3$) δ 8.35 (1H, d, J=8.03 Hz,), 7.69 (2H, J=7.78 Hz), 7.53-7.63 (2H, m), 6.91-7.16 (1H, m), 3.21 (1H, br.s.), 1.72-1.96 (6H, m), 1.61 (2H, br.s.), 1.18 (3H, s).

(cis)-4-(1-(2-chloro-6-(trifluoromethyl)benzoyl)-4-fluoro-1H-indazol-3-yl)-1-methylcyclohexanecarboxylic acid (9B): 6 mg, LCMS (ESI) calc'd for $C_{23}H_{19}ClF_4N_2O_3$ [M+H]$^+$: 483, found: 483. $^1$H NMR (400 MHz, CDCl$_3$) δ 8.35 (1H, d, J=8.53 Hz), 7.60-7.69 (2H, m), 7.47-7.60 (2H, m), 6.95-7.10 (1H, m,), 3.50 (1H, s), 2.82-3.15 (1H, m), 2.28 (2H, J=13.05 Hz, d), 1.92 (2H, d, J=12.55 Hz), 1.67 (1H, t, J=10.29 Hz), 1.28-1.38 (2H, m), 1.27 (3H, s).

Example 10A and 10B

Preparation of (R and S)-4-(1-(2-chloro-6-(trifluoromethyl)benzoyl)-4-fluoro-1H-indazol-3-yl)-2,2-dimethylcyclohex-3-enecarboxylic acid (10A) and (R and S) 4-(1-(2-chloro-6-(trifluoromethyl)benzoyl)-4-fluoro-1H-indazol-3-yl)-6,6-dimethylcyclohex-3-enecarboxylic acid (10B)

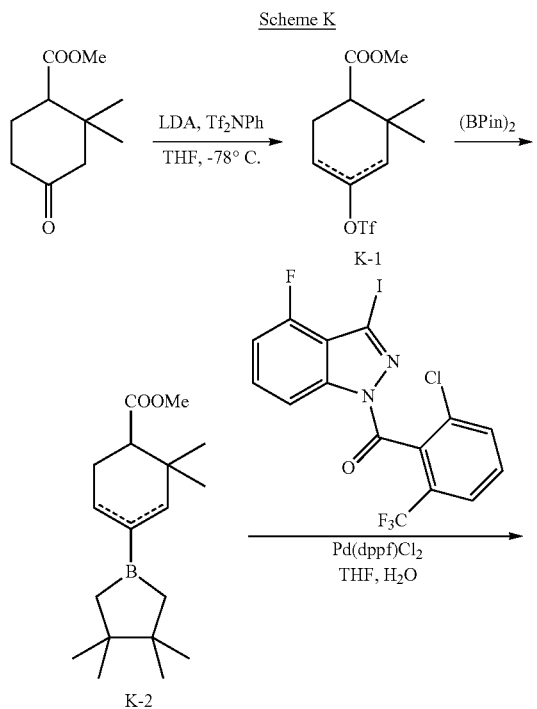

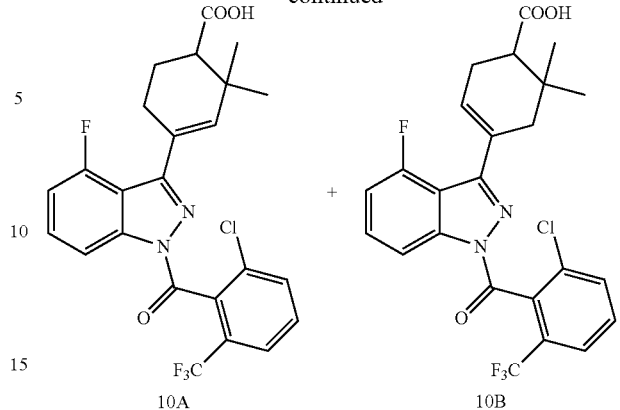

Step 1: Preparation of mixture of methyl 2,2-dimethyl-4-(((trifluoromethyl)sulfonyl)oxy)cyclohex-3-enecarboxylate and methyl 6,6-dimethyl-4-(((trifluoromethyl)sulfonyl)oxy)cyclohex-3-enecarboxylate (K-1)

To a solution of methyl 2,2-dimethyl-4-oxocyclohexanecarboxylate (1.5 g, 8.14 mmol) in THF (15 mL), was added dropwise LDA (10 mL, 10 mmol) at −78° C. for 15 min. Tf$_2$NPh (3.78 g, 10.6 mmol) in THF (10 mL) was added dropwise. The mixture was stirred at −78° C. for 2 h and stirred at 20° C. for additional 10 h. The resulting mixture was quenched with 30 mL of saturated aqueous NH4Cl and extracted with ethyl acetate (15 mL×2). The combined organic fractions were washed with brine (saturated, 10 mL), dried over Na$_2$SO$_4$, filtered and concentrated under reduced pressure. The residue was purified by column chromatography on silica gel (ethyl acetate/petroleum ether=1/20) to give the title compounds (ratio=1:6, 1 g, yield: 34.9%) as yellow oils.

Step 2: Preparation of mixture of methyl 2,2-dimethyl-4-(4,4,5,5-tetramethyl-1,3,2-dioxaborolan-2-yl)cyclohex-3-enecarboxylate and methyl 6,6-dimethyl-4-(4,4,5,5-tetramethyl-1,3,2-dioxaborolan-2-yl)cyclohex-3-enecarboxylate (K-2)

To a mixture of methyl 2,2-dimethyl-4-(((trifluoromethyl)sulfonyl)oxy)cyclohex-3-enecarboxylate and methyl 6,6-dimethyl-4-(((trifluoromethyl)sulfonyl)oxy)cyclohex-3-enecarboxylate (K-1, ratio=1:6, 900 mg, 2.85 mmol) in 1,4-dioxane (50 mL) was added Bis(pinacolato)diboron (723 mg, 2.85 mmol) and potassium acetate (838 mg, 8.54 mmol). The mixture was purged with nitrogen for 20 minutes, and PdCl$_2$(dppf)-CH$_2$Cl$_2$ (697 mg, 0.854 mmol) and dppf (4732 mg, 8.54 mmol) were added. The mixture was stirred at 100° C. for 2 h. The resulting mixture was filtered over a Celite pad and the filtrate was diluted with water (50 mL) and extracted with ethyl acetate (50 mL×3). The combined organic layers were washed with brine, dried over anhydrous Na$_2$SO$_4$ and concentrated in vacuo. The crude product was purified by column chromatography on silica gel (ethyl acetate/petroleum=1/20) to give the title compound (ratio=1:6, 400 mg, yield: 43%) as a yellow oil. LCMS (ESI) calc'd for $C_{16}H_{27}BO_4$ [M+H]$^+$: 295, found: 295.

Step 3: Preparation of mixture of methyl 4-(1-(2-chloro-6-(trifluoromethyl)benzoyl)-4-fluoro-1H-indazol-3-yl)-2,2-dimethylcyclohex-3-enecarboxylate and methyl 4-(1-(2-chloro-6-(trifluoromethyl)benzoyl)-4-fluoro-1H-indazol-3-yl)-6,6-dimethylcyclohex-3-enecarboxylate (K-3)

To a solution of (2-chloro-6-(trifluoromethyl)phenyl)(4-fluoro-3-iodo-1H-indazol-1-yl)methanone (510 mg, 1.088 mmol) in THF/H$_2$O (40 mL/10 mL) was added a mixture of methyl 2,2-dimethyl-4-(4,4,5,5-tetramethyl-1,3,2-dioxaborolan-2-yl)cyclohex-3-enecarboxylate and methyl 6,6-dimethyl-4-(4,4,5,5-tetramethyl-1,3,2-dioxaborolan-2-yl)cyclohex-3-enecarboxylate (K-2, ratio=1:6, 400 mg, 1.36 mmol) and Na$_2$CO$_3$ (432 mg, 4.08 mmol). The mixture was purged with nitrogen for 20 minutes, Pd(dppf)Cl$_2$ (298 mg, 0.408 mmol) was added and the mixture was stirred at 80° C. for 10 h. The resulting mixture was filtered over a Celite pad, and the filtrate was diluted with water (40 mL) and extracted with ethyl acetate (60 mL×3). The combined organic layers were washed with brine, dried over anhydrous Na$_2$SO$_4$ and concentrated in vacuo. The crude product was purified by column chromatography on silica gel (ethyl acetate/petroleum ether=1/10) to give the title compound (ratio: 1:6, 191 mg, yield: 26.4%) as a yellow oil. LCMS (ESI) calc'd for C$_{25}$H$_{21}$ClF$_4$N$_2$O$_3$ [M+H]$^+$: 509, found: 509.

Step 4: Preparation of (R and S)-4-(1-(2-chloro-6-(trifluoromethyl)benzoyl)-4-fluoro-1H-indazol-3-yl)-2,2-dimethylcyclohex-3-enecarboxylic acid (10A) and (R and S)-4-(1-(2-chloro-6-(trifluoromethyl)benzoyl)-4-fluoro-1H-indazol-3-yl)-6,6-dimethylcyclohex-3-enecarboxylic acid (10B)

A mixture of methyl 4-(1-(2-chloro-6-(trifluoromethyl)benzoyl)-4-fluoro-1H-indazol-3-yl)-2,2-dimethylcyclohex-3-enecarboxylate, methyl 4-(1-(2-chloro-6-(trifluoromethyl)benzoyl)-4-fluoro-1H-indazol-3-yl)-6,6-dimethylcyclohex-3-enecarboxylate (K-3, ratio=1:6, 200 mg, 0.39 mmol), NaOH (47.2 mg, 1.18 mmol) and methanol (10 mL) was stirred at 40° C. for 10 h. The resulting mixture was concentrated in vacuo, diluted with water (10 mL) and washed with ethyl acetate (10 mL×2). The aqueous layer was acidified with 2 M HCl to pH=2. The precipitate was collected by filtration and dried in vacuo. The desired product was purified by prep-HPLC (acetonitrile+0.75% trifluoroacetic acid in water) to give two separate isomers:

(R and S)-4-(1-(2-chloro-6-(trifluoromethyl)benzoyl)-4-fluoro-1H-indazol-3-yl)-2,2-dimethyl yclohex-3-enecarboxylic acid (10A): 5 mg, LCMS (ESI) calc'd for C$_{24}$H$_{19}$ClF$_4$N$_2$O$_3$ [M+H]$^+$: 495, found: 495. $^1$H NMR (400 MHz, CDCl$_3$) δ 8.43 (1H, d, J=8.53 Hz), 7.65-7.75 (2H, m), 7.51-7.64 (2H, m), 7.11 (1H, dd, J=11.04, 8.03 Hz), 6.57 (1H, br.s.), 2.48-2.55 (2H, m), 2.23 (2H, d, J=8.03 Hz), 1.08 (3H, s), 2.18 (1H, s), 1.02 (3H, d, J=3.01 Hz).

(R and S)-4-(1-(2-chloro-6-(trifluoromethyl)benzoyl)-4-fluoro-1H-indazol-3-yl)-6,6-dimethylcyclohex-3-enecarboxylic acid (10B): 20 mg, LCMS (ESI) calc'd for C$_{24}$H$_{19}$ClF$_4$N$_2$O$_3$ [M+H]$^+$: 495, found: 495. $^1$H NMR (400 MHz, CDCl$_3$) δ 8.43 (1H, d, J=8.53 Hz), 7.65-7.74 (2H, m), 7.52-7.63 (2H, m), 7.11 (1H, dd, J=10.54, 8.03 Hz), 6.37 (1H, br.s.), 2.44-2.60 (2H, m), 2.14-2.28 (3H, m), 1.08 (3H, s), 1.02 (3H, d, J=3.01 Hz).

Example 11A and 11B

Preparation of (trans)-4-(1-(2-chloro-6-(trifluoromethyl)benzoyl)-1H-pyrazolo[4,3-b]pyridin-3-yl)cyclohexanecarboxylic acid (11A) and (cis)-4-(1-(2-chloro-6-(trifluoromethyl)benzoyl)-1H-pyrazolo[4,3-b]pyridin-3-yl)cyclohexanecarboxylic acid (11B)

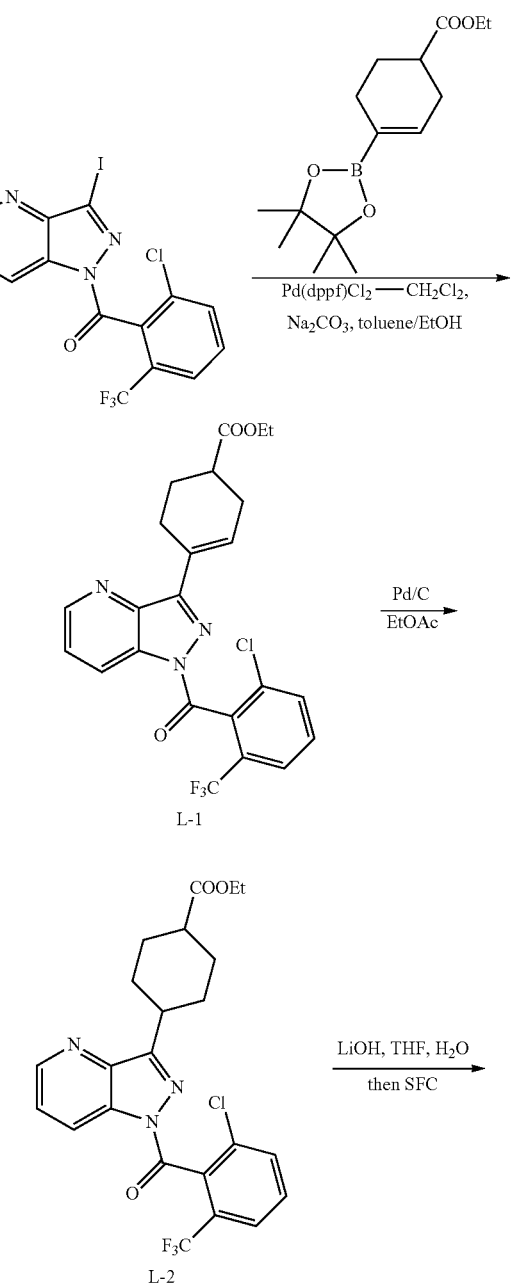

Scheme L

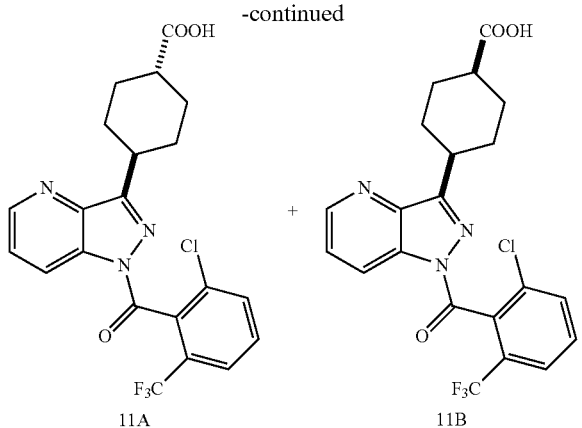

Step 1: Preparation of ethyl 4-(1-(2-chloro-6-(trifluoromethyl)benzoyl)-1H-pyrazolo[4,3-b]pyridin-3-yl)cyclohex-3-enecarboxylate (L-1)

To a mixture of (2-chloro-6-(trifluoromethyl)phenyl)(3-iodo-1H-pyrazolo[4,3-b]pyridin-1-yl)methanone (1 g, 2.2 mmol) and ethyl 4-(4,4,5,5-tetramethyl-1,3,2-dioxaborolan-2-yl)cyclohex-3-enecarboxylate (0.8 g, 2.8 mmol) in 40 mL of toluene/EtOH (1:1), was added 1.6 mL of a saturated Na$_2$CO$_3$ solution and Pd(dppf)Cl$_2$—CH$_2$Cl$_2$ (182 mg, 0.22 mmol) while stirring under N$_2$. The reaction mixture was heated to 120° C. for 6 h. Upon completion, the mixture was filtered and the organic layer was concentrated in vacuo. The product was purified by silica gel chromatography, eluting with PE:EA=100:1 to PE:EA=10:1 to afford the title compound (500 mg, 47%) as a yellow solid. LCMS (ESI) calc'd for C$_{23}$H$_{19}$ClF$_3$N$_3$O$_3$ [M+H]$^+$: 478, found: 478.

Step 2: Preparation of ethyl 4-(1-(2-chloro-6-(trifluoromethyl)benzoyl)-1H-pyrazolo[4,3-b]pyridin-3-yl)cyclohexanecarboxylate (L-2)

To a solution of ethyl 4-(1-(2-chloro-6-(trifluoromethyl)benzoyl)-1H-pyrazolo[4,3-b]pyridin-3-yl)cyclohex-3-enecarboxylate (L-1) (500 mg, 1.05 mmol) in EtOAc (30 mL), was added Pd/C (50 mg). The resulting reaction mixture was stirred under H$_2$ (1 atm) for 24 h at 40° C. The reaction mixture was filtered, and the filtrate was evaporated to give the title compound (500 mg, yield: 99%) as a yellow oil. LCMS (ESI) calc'd for C$_{23}$H$_{21}$ClF$_3$N$_3$O$_3$ [M+H]$^+$: 480. found: 480.

Step 3: Preparation of (trans)-4-(1-(2-chloro-6-(trifluoromethyl)benzoyl)-1H-pyrazolo[4,3-b]pyridin-3-yl)cyclohexanecarboxylic acid (11A) and (cis)-4-(1-(2-chloro-6-(trifluoromethyl)benzoyl)-1H-pyrazolo[4,3-b]pyridin-3-yl)cyclohexanecarboxylic acid (11B)

To a solution of ethyl 4-(1-(2-chloro-6-(trifluoromethyl)benzoyl)-1H-pyrazolo[4,3-b]pyridin-3-yl)cyclohexanecarboxylate (L-2) (500 mg, 1.04 mmol) in 10 mL of THF/H$_2$O (4:1) was added lithium hydroxide monohydrate (175 mg, 4.16 mmol). The reaction mixture was stirred for 24 h at 30° C. Upon completion, the reaction was diluted with 10 mL of water and extracted with PE (200 mL×2). The aqueous layer was acidified with 2 M HCl to pH=3, then extracted with EtOAc (300 mL×3). The combined organics were washed with brine (200 mL×2), dried over Na$_2$SO$_4$ and concentrated to afford product (300 mg, 64%) as a yellow solid, which was further separated by SFC to afford two separate isomers (Column: Chiralcel OJ-H 250×4.6 mm I.D., 5 um; Mobile phase: ethanol (0.05% DEA) in CO$_2$ from 5% to 40%) to give two isomers, LCMS (ESI) calc'd for C$_{21}$H$_{17}$ClF$_3$N$_3$O$_3$ [M+H]$^+$: 452, found: 452.

(trans)-4-(1-(2-chloro-6-(trifluoromethyl)benzoyl)-1H-pyrazolo[4,3-b]pyridin-3-yl)cyclohexane carboxylic acid (11A): $^1$H NMR (400 MHz CDCl$_3$) δ 8.91 (1H, J=8.54 Hz, d), 8.83 (1H, d, J=4.02 Hz), 7.62-7.72 (3H, m), 7.48-7.59 (1H, m), 3.51 (1H, br. s.), 2.55 (1H, br. s.), 1.86-2.01 (6H, m), 1.66-1.76 (2H, m).

(cis)-4-(1-(2-chloro-6-(trifluoromethyl)benzoyl)-1H-pyrazolo[4,3-b]pyridin-3-yl)cyclohexanecarboxylic acid (11B): $^1$H NMR (400 MHz CDCl$_3$) δ 8.75-8.83 (2H, m), 7.67-7.72 (2H, m), 7.60 (1H, d, J=8.04 Hz), 7.54 (1H, dd, J=8.54, 4.52 Hz,), 3.13-3.23 (1H, m), 2.38-2.49 (1H, m), 2.10-2.19 (4H, m), 1.59-1.74 (4H, m).

Example 12A

Preparation of 4-(1-(2-chloro-6-(trifluoromethyl)benzoyl)-4-fluoro-1H-indazol-3-yl)-5-methylcyclohex-3-enecarboxylic acid Scheme M

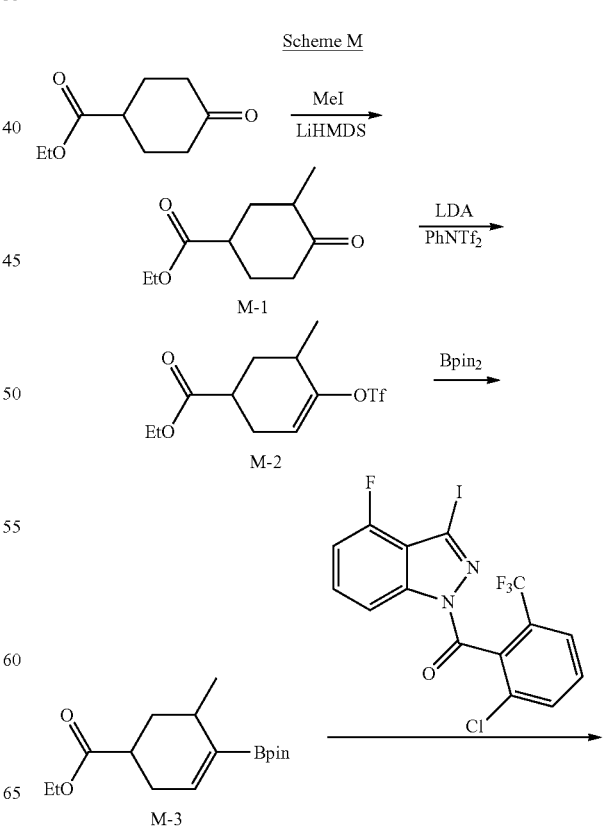

-continued

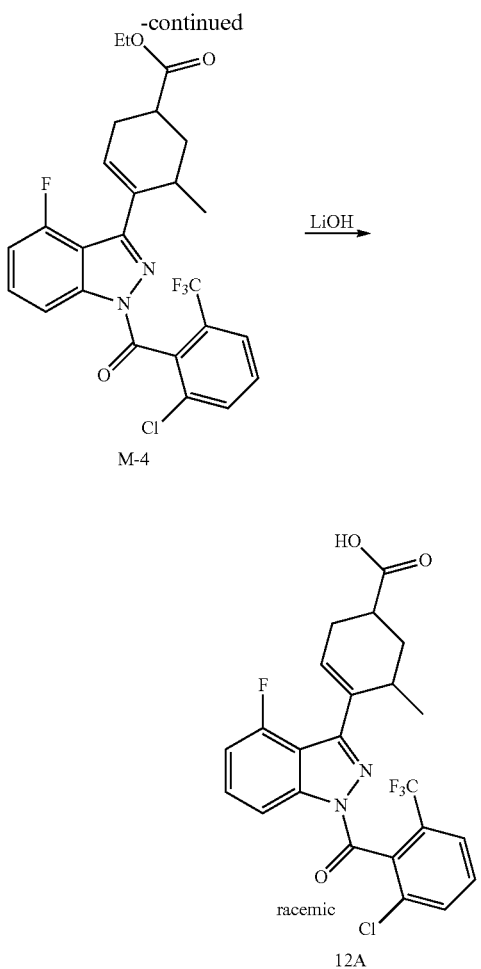

M-4

12A racemic

Step 1: Preparation of ethyl 3-methyl-4-oxocyclohexanecarboxylate (M-1)

To a solution of ethyl 4-oxocyclohexanecarboxylate (10 g, 58 mmol) in THF (100 mL) was added LiHMDS (65 mL, 65 mmol) portionwise, while stirring at −78° C. under $N_2$. After stirring for 1 h, iodomethane (8.34 g, 58 mmol) was added dropwise. The mixture was stirred at ambient temperature for 2 h. The mixture was diluted with water (150 mL) and extracted with EtOAc (100 mL×3). The combined organics were washed with brine, dried over $Na_2SO_4$ and evaporated. The residue was purified by silica gel chromatography, eluting with PE:EA=30:1 to afford the title compound (4 g, yield: 37%). LCMS (ESI) calc'd for $C_{10}H_{16}O_3$ $[M+H]^+$: 185, found: 185.

Step 2: Preparation of ethyl 5-methyl-4-(((trifluoromethyl)sulfonyl)oxy)cyclohex-3-enecarboxylate (M-2)

To a solution of ethyl 3-methyl-4-oxocyclohexanecarboxylate (M-1) (5 g, 27 mmol) in THF (60 mL) was added LDA (13.5 mL, 2.5M in THF, 27 mmol) portionwise while stirring at 0° C. under $N_2$. After stirring for 1 h, PhNTf$_2$ (9.64 g, 27 mmol) was added dropwise. The mixture was stirred at ambient temperature for 12 h. The mixture was quenched with water (150 mL) and extracted with EtOAc (50 mL×3). The combined organic layer was washed with brine, dried over $Na_2SO_4$ and evaporated. The residue was purified by silica gel chromatography, eluting with PE:EA=100:1 to afford the title compound (5 g, yield: 63%). LCMS (ESI) calc'd for $C_{11}H_{15}F_3O_5S$ $[M+H]^+$: 317, found: 317.

Step 3: Preparation of ethyl 5-methyl-4-(4,4,5,5-tetramethyl-1,3,2-dioxaborolan-2-yl)cyclohex-3-enecarboxylate (M-3)

To a mixture of ethyl 5-methyl-4-(((trifluoromethyl)sulfonyl)oxy)cyclohex-3-enecarboxylate (M-2) (3.0 g, 9.5 mmol), (Bpin)$_2$ (2.65 g, 10.4 mmol), KOAc (2.8 g, 28.5 mmol), and Dioxane (50 mL) was added Pd(dppf)Cl$_2$.CH$_2$Cl$_2$ (700 mg) while purging with nitrogen. The mixture was heated at 100° C. for 3 h. The solution was cooled and filtered over Celite. The solution was evaporated and purified by column chromatography on silica gel (PE:EA=200:1) to give the title compound (1 g, yield: 36%). LCMS (ESI) calc'd for $C_{16}H_{27}BO_4$ $[M+H]^+$: 295, found: 295.

Step 4: Preparation of ethyl 4-(1-(2-chloro-6-(trifluoromethyl)benzoyl)-4-fluoro-1H-indazol-3-yl)-5-methylcyclohex-3-enecarboxylate (M-4)

A solution of (2-chloro-6-(trifluoromethyl)phenyl)(4-fluoro-3-iodo-1H-indazol-1-yl)methanone (2.2 g, 4.6 mmol), ethyl 5-methyl-4-(4,4,5,5-tetramethyl-1,3,2-dioxaborolan-2-yl)cyclohex-3-enecarboxylate (M-3) (1.5 g, 5.1 mmol), Pd(dppf)Cl$_2$.CH$_2$Cl$_2$ (340 mg) and Cs$_2$CO$_3$ (4.5 g, 13.8 mmol) in THF (30 mL) under $N_2$ was stirred at 100° C. for 4 h. After 4 hours, the reaction was filtered, and the filtrate was concentrated and purified by column chromatography (PE:EA=50:1) to give the title compound (1.4 g, yield: 61%). LCMS (ESI) calc'd for $C_{25}H_{21}ClF_4N_2O_3$ $[M+H]^+$: 509, found: 509.

Step 5: Preparation of 4-(1-(2-chloro-6-(trifluoromethyl)benzoyl)-4-fluoro-1H-indazol-3-yl)-5-methylcyclohex-3-enecarboxylic acid (12A)

A solution of ethyl 4-(1-(2-chloro-6-(trifluoromethyl)benzoyl)-4-fluoro-1H-indazol-3-yl)-5-methylcyclohex-3-enecarboxylate (M-4) (100 mg, 0.2 mmol) and LiOH.H$_2$O (34 mg, 0.8 mmol) in THF/H$_2$O (3/1 mL) was stirred at room temperature overnight. The next morning the reaction was concentrated, and the residue was diluted with 15 mL of water and acidified with 1 M HCl to pH=3-4; was then extracted with EA. The combined organics were washed with brine (200 mL×2), dried over $Na_2SO_4$ and concentrated. The residue was purified by prep-TLC to give the title compound as a racemate (50 mg, yield: 52%). LCMS (ESI) calc'd for $C_{23}H_{17}ClF_4N_2O_3$ $[M+H]^+$: 481, found: 481. $^1$H-NMR (400 MHz, CDCl$_3$) δ 8.39-8.43 (1H, m), 7.56-7.68 (4H, m), 7.06-7.11 (1H, m), 6.21-6.51 (1H, m), 2.17-2.95 (5H, m), 1.38-1.58 (1H, m), 0.84-0.97 (3H, m).

Example 13A

Preparation of 4-(1-(2-chloro-6-(trifluoromethyl)benzoyl)-4-fluoro-1H-indazol-3-yl)-4-hydroxycyclohexanecarboxylic acid Scheme N

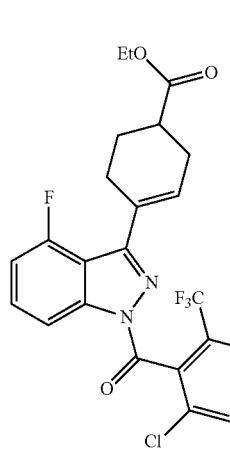

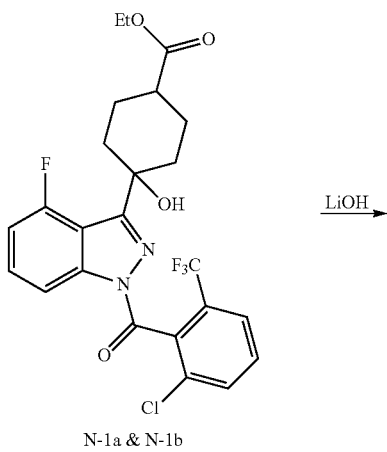

N-1a & N-1b

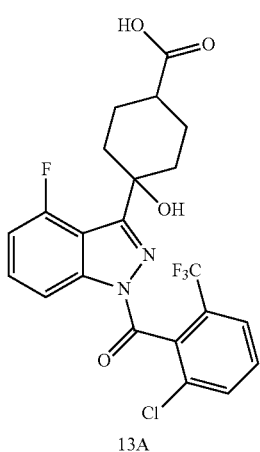

13A

Step 1: Preparation of (trans or cis) ethyl 4-(1-(2-chloro-6-(trifluoromethyl)benzoyl)-4-fluoro-1H-indazol-3-yl)-4-hydroxycyclohexanecarboxylate (N-1a) and (cis or trans)-ethyl 4-(1-(2-chloro-6-(trifluoromethyl)benzoyl)-4-fluoro-1H-indazol-3-yl)-4-hydroxycyclohexanecarboxylate (N-1b)

To a solution of ethyl 4-(1-(2-chloro-6-(trifluoromethyl)benzoyl)-4-fluoro-1H-indazol-3-yl)cyclohex-3-enecarboxylate (500 mg, 1 mmol) in THF (10 mL) was added $BH_3 \cdot Me_2S$ (228 mg, 3 mmol). The reaction mixture was stirred at room temperature overnight. Then a.q. NaOH (1 mL, 3M) solution and $H_2O_2$ (0.5 mL, 30%) was added. The reaction mixture was stirred at room temperature for 3 h. The mixture was extracted with EtOAc. The organic layer was washed with $H_2O$, brine, dried over $Na_2SO_4$ and concentrated. The crude product was purified by prep-HPLC (acetonitrile+0.75% trifluoroacetic acid in water) to give the title compounds (Peak 1—N-1a, 70 mg, 27%) (Peak 2—N-1b, 70 mg, 27%). LCMS (ESI) calc'd for $C_{24}H_{21}ClF_4N_2O_4$ $[M+H]^+$: 513, found: 513.

Step 2: Preparation of 4-(1-(2-chloro-6-(trifluoromethyl)benzoyl)-4-fluoro-1H-indazol-3-yl)-4-hydroxycyclohexanecarboxylic acid (13A)

A solution of (cis or trans)-ethyl 4-(1-(2-chloro-6-(trifluoromethyl)benzoyl)-4-fluoro-1H-indazol-3-yl)-4-hydroxycyclohexanecarboxy late (Peak 2—N-1b, 70 mg, 0.2 mmol) and $LiOH \cdot H_2O$ (35 mg, 0.83 mmol) in $THF/H_2O$ (3/1 mL) was stirred at room temperature overnight. The mixture was concentrated, and the residue was diluted in 5 mL of water and acidified with 1 M HCl to pH=3-4 and then extracted with EA. The combined organics were washed with brine (200 mL×2), dried over $Na_2SO_4$ and concentrated. The residue was purified by prep-TLC to give the title compound (10 mg, yield: 15%). LCMS (ESI): calc'd for $C_{22}H_{17}ClF_4N_2O_4$ $[M+H]^+$: 485, found: 485. $^1$H-NMR (400 MHz $CDCl_3$) δ 8.42 (1H, d, J=8.4 Hz), 7.55-7.67 (4H, m), 7.11-7.16 (1H, m), 2.50-2.54 (1H, m), 2.33-2.38 (2H, m), 1.89-1.92 (2H, m), 1.68-1.76 (4H, m).

Biological Assays

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., *Methods* 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was expressed in SF9 cells using a baculovirus expression system. The RORγ-LBD protein was purified by glutathione sepharose chromatography. Separately, SF9 cells not expressing any recombinant protein were lysed and the lysate was added to the purified RORγ-LBD at 0.25 μl lysate (from 10,000 SF9 cells)/nM purified protein. The mixture was then diluted in assay buffer (50 mM Tris pH 7.0, 50 mM KCl, 1 mM EDTA, 0.1 mM DTT) to obtain RORγ-LBD final concentration of 3 nM in 384-well assay plate.

Compounds to be tested were injected to the assay plate using Acoustic Droplet Ejection technology by Echo 550 liquid handler (Labcyte, Calif.).

A stock of biotinylated-LXXLL peptide from coactivator SRC1 (Biotin-CPSSHSSLTERHKILHRLLQEGSPS) (SEQ ID NO:2) was prepared in assay buffer and added to each well (100 nM final concentration). A solution of Europium tagged anti-HIS antibody (1.25 nM final concentration) and APC conjugated streptavidin (8 nM final concentration) were also added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

Biological Data

The following table tabulates the biological data disclosed for the instant invention

| Examples | Fret IC$_{50}$ (nM) |
|---|---|
| 1A | 18 |
| 1B | 21 |
| 1C | 13 |
| 1D | 774 |
| 1E | 76 |
| 1F | 170 |
| 1G | 182 |
| 1H | 20 |
| 1I | 14 |
| 1J | 7 |
| 1K | 31 |
| 1L | 123 |
| 2A | 2 |
| 2B | 2 |
| 2C | 4 |
| 2D | 5 |
| 3A | 6 |
| 3B | 5 |
| 4A | 5 |
| 4B | 143 |
| 4C | 9 |
| 4D | 177 |
| 4E | 2 |
| 4F | 30 |
| 4G | 6 |
| 4H | 115 |
| 4I | 3 |
| 4J | 24 |
| 4K | 94 |
| 4L | 36 |
| 4M | 21 |
| 4N | 3 |
| 4O | 308 |
| 4P | 41 |
| 4Q | 380 |
| 4R | 21 |
| 4S | 40 |
| 4T | 1116 |
| 4U | 164 |
| 4V | 31 |
| 4W | 3 |
| 4X | 3 |
| 4Y | 159 |
| 4Z | 258 |
| 4AA | 7 |
| 4AB | 8 |
| 5A | 4 |
| 6A | 2 |
| 6B | 15 |
| 6C | 5 |
| 7A | 1879 |
| 7B | 663 |
| 7C | 872 |
| 8A | 16 |
| 8B | 505 |
| 9A | 50 |
| 9B | 5022 |
| 10A | 343 |
| 10B | 96 |
| 11A | 207 |
| 11B | 10000 |
| 12A | 54 |
| 13A | 2474 |

The invention claimed is:

1. A compound according to Formula I

I or a pharmaceutically acceptable salt or solvate thereof, wherein:

a is a bond or no bond;
X is C(O);
Y is $N^a$;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than two of $A^4$-$A^7$ can be N;
$R^1$ is
  (i) $(C_{3-12})$carbocyclyl; or
  (ii) a 4- to 12-membered heterocyclyl,
  both (i) and (ii) optionally substituted with one, two, three, four or five $R^8$;
$R^2$ is hydroxycarbonyl, or carbamoyl;
$R^3$ is hydrogen, halogen, cyano, nitro, hydroxy, $(C_{1-3})$alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;
$R^4$-$R^7$ independently are H, halogen, amino, cyano, hydroxy, $(C_{1-3})$alkoxy, $(C_{1-4})$alkyl, $(C_{0-10}$alkyl)aminocarbonyl, (di)$(C_{1-6})$alkylaminocarbonyl or amino$(C_{1-4})$alkyl, wherein $(C_{1-3})$alkoxy, $(C_{1-4})$alkyl, $(C_{0-10}$alkyl)aminocarbonyl, (di)$(C_{1-6})$alkylaminocarbonyl and amino$(C_{1-4})$alkyl are optionally substituted with one or more halogen, hydroxyl or $(C_{1-3})$alkoxy; or a group having the formula optionally substituted with one or more of the following: $(C_{1-10})$alkyl, halogen, amino, cyano, hydroxy, $(C_{1-3})$alkoxy, and
wherein m is 1, 2, 3, or 4;
$R^8$ is halogen, cyano, amino, nitro, hydroxy, $H_2NC(O)$—, $(C_{1-3})$alkoxycarbonyl, (di)$(C_{1-6})$alkylaminocarbonyl, $(C_{1-4})$alkyl, $(C_{3-7})$cycloalkyl, $(C_{3-5})$heterocycloalkyl, (C1-3)alkoxyaminocarbonyl, 4- to 8-membered heterocyclylcarbonyl, (C3-6)cycloalkylaminocarbonyl, amino(C1-4)alkyloxycarbonyl or $(C_{1-3})$alkoxy, wherein $(C_{1-3})$alkoxycarbonyl, (di)$(C_{1-6})$alkylaminocarbonyl, $(C_{1-4})$alkyl, (C1-3)alkoxyaminocarbonyl, 4- to 8-membered heterocyclylcarbonyl, (C3-6)cycloalkylaminocarbonyl, amino$(C_{1-4})$alkyloxycarbonyl and $(C_{1-3})$alkoxy are optionally substituted with oxo, $(C_{1-4})$alkyl, hydroxy$(C_{1-3})$alkyl, or one, two or three halogens.

2. A compound having Formula Ix

Ix or a pharmaceutically acceptable salt or solvate thereof wherein,
X is $CH_2$ or C(O);
Y is CH, N, or $CR^a$;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than two of $A^4$-$A^7$ can be N;
$R^a$ is $(C_{1-4})$alkyl;
$R^1$ is
  (i) $(C_{3-12})$carbocyclyl; or
  (ii) a 4- to 12-membered heterocyclyl,
  both (i) and (ii) optionally substituted with one, two, three, four or five $R^8$;
$R^2$ is hydroxycarbonyl, hydroxycarbonyl$(C_{1-10})$alkyl, or carbamoyl;
$R^3$ is hydrogen, halogen, cyano, nitro, hydroxy, $(C_{1-3})$alkylC(O)O—, $(C_{1-4})$alkyl, or $(C_{1-4})$alkoxy, wherein $(C_{1-4})$alkyl and $(C_{1-4})$alkoxy are optionally substituted with one or more halogen;

$R^4$-$R^7$ independently are H, halogen, amino, cyano, hydroxy, $(C_{1-3})$alkoxy, $(C_{1-4})$alkyl, $(C_{0-10})$alkyl)aminocarbonyl, $(di)(C_{1-6})$alkylaminocarbonyl or amino$(C_{1-4})$alkyl, wherein $(C_{1-3})$alkoxy, $(C_{1-4})$alkyl, $(C_{0-10})$alkyl)aminocarbonyl, $(di)(C_{1-6})$alkylaminocarbonyl and amino$(C_{1-4})$alkyl are optionally substituted with one or more halogen, hydroxyl or $(C_{1-3})$alkoxy; or a group having the formula

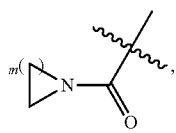

optionally substituted with one or more of the following: $(C_{1-10})$alkyl, halogen, amino, cyano, hydroxy, $(C_{1-3})$alkoxy, and wherein m is 1, 2, 3, or 4;

$R^8$ is halogen, cyano, amino, nitro, hydroxy, $H_2NC(O)$—, $(C_{1-3})$alkoxycarbonyl, $(di)(C_{1-6})$alkylaminocarbonyl, $(C_{1-4})$alkyl, $(C_{3-7})$cycloalkyl, $(C_{3-5})$heterocycloalkyl, $(C_{1-3})$alkoxyaminocarbonyl, 4- to 8-membered heterocyclylcarbonyl, $(C_{3-6})$cycloalkylaminocarbonyl, amino$(C_{1-4})$alkyloxycarbonyl or $(C_{1-3})$alkoxy, wherein $(C_{1-3})$alkoxycarbonyl, $(di)(C_{1-6})$alkylaminocarbonyl, $(C_{1-4})$alkyl, $(C_{1-3})$alkoxyaminocarbonyl, 4- to 8-membered heterocyclylcarbonyl, $(C_{3-6})$cycloalkylaminocarbonyl, amino$(C_{1-4})$alkyloxycarbonyl and $(C_{1-3})$alkoxy are optionally substituted with oxo, $(C_{1-4})$alkyl, hydroxy$(C_{1-3})$alkyl, or one, two or three halogens.

3. The compound of claim 2 having Formula Ia

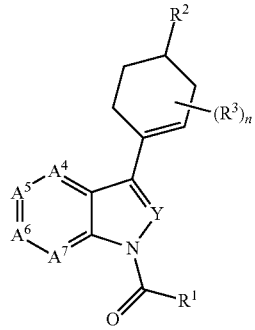

or a pharmaceutically acceptable salt or solvate thereof.

4. The compound of claim 2 having Formula Ib

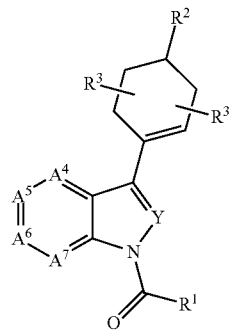

or a pharmaceutically acceptable salt or solvate thereof.

5. The compound of claim 4, wherein Y is N.

6. The compound of claim 4 having Formula Ic

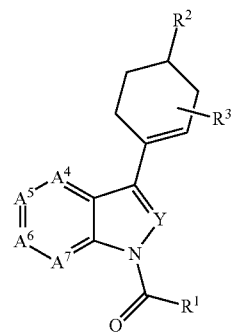

or a pharmaceutically acceptable salt or solvate thereof.

7. The compound of claim 3 having Formula Id

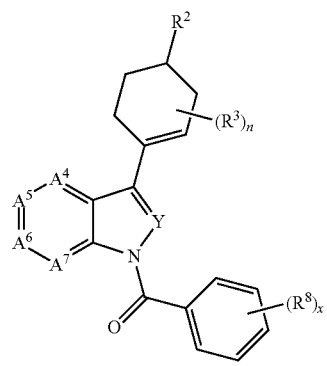

wherein x is 1, 2, 3, 4 or 5, or a pharmaceutically acceptable salt or solvate thereof.

8. The compound of claim 7 having Formula Ie

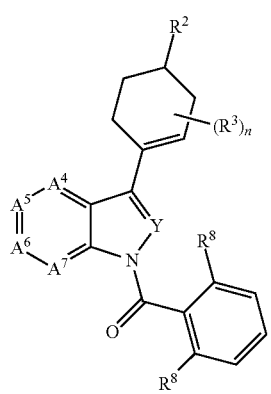

or a pharmaceutically acceptable salt or solvate thereof.

9. The compound of claim 8 having Formula If

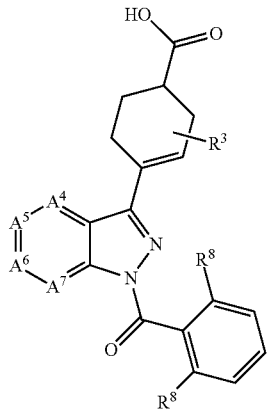

or a pharmaceutically acceptable salt or solvate thereof.

10. The compound of claim 2 having Formula Ig

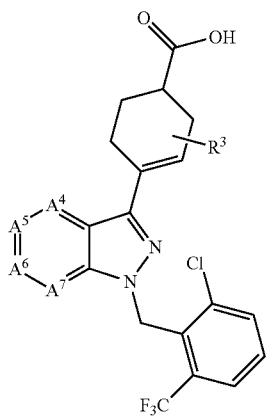

or a pharmaceutically acceptable salt or solvate thereof.

11. The compound of claim 1, wherein $A^4$, $A^5$, $A^6$, $A^7$ is (i) $CR^4$, $CR^5$, $CR^6$, $CR^7$; or (ii) N, $CR^5$, $CR^6$, $CR^7$.

12. The compound of claim 11, wherein $R^1$ is $(C_{6-14})$aryl, optionally substituted with one, two, three, four or five $R^8$.

13. The compound of claim 12, wherein $R^1$ is phenyl, optionally substituted with one, two or three $R^8$.

14. The compound of claim 13, wherein $R^2$ is C(O)OH.

15. A compound selected from:
4-(1-(2-chloro-6-(trifluoromethyl)benzoyl)-6-(dimethylcarbamoyl)-1H-indazol-3-yl)cyclohex-3-enecarboxylic acid;
4-(1-(2-chloro-6-(trifluoromethyl)benzoyl)-4-fluoro-1H-indazol-3-yl)cyclohex-3-enecarboxylic acid;
4-(1-(2-chloro-6-(trifluoromethyl)benzoyl)-6-(2-hydroxyethylcarbamoyl)-1H-indazol-3-yl)cyclohex-3-enecarboxylic acid;
4-(1-(2-chloro-6-(trifluoromethyl)benzoyl)-1H-pyrazolo[4,3-b]pyridin-3-yl)cyclohex-3-enecarboxylic acid;
4-(1-(2-chloro-6-(trifluoromethyl)benzoyl)-1H-pyrazolo[4,3-b]pyridin-3-yl)-1-methylcyclohex-3-enecarboxylic acid;
4-(1-(2-chloro-6-(trifluoromethyl)benzoyl)-1H-pyrazolo[4,3-b]pyridin-3-yl)-2-methylcyclohex-3-enecarboxylic acid;
4-(1-(2-chloro-6-(trifluoromethyl)benzoyl)-1H-indazol-3-yl)cyclohex-3-enecarboxylic acid;
4-(4-chloro-1-(2-chloro-6-(trifluoromethyl)benzoyl)-1H-indazol-3-yl)-1-methylcyclohex-3-enecarboxylic acid;
4-(1-(2-chloro-6-cyclopropylbenzoyl)-4-fluoro-1H-indazol-3-yl)-1-methylcyclohex-3-enecarboxylic acid;
4-(1-(2-chloro-6-methylbenzoyl)-4-fluoro-1H-indazol-3-yl)cyclo-hex-3-enecarboxylic acid;
4-(1-(2-chloro-6-methylbenzoyl)-1H-pyrazolo[4,3-b]pyridine-3-yl)cyclohex-3-enecarboxylic acid;
(R or S)-4-(1-(2-chloro-6-cyclopropylbenzoyl)-6-(3-methoxy azetidine-1-carbonyl)-1H-indazol-3-yl)cyclohex-3-enecarboxylic acid;
(S or R)-4-(1-(2-chloro-6-cyclopropylbenzoyl)-6-(3-methoxy azetidine-1-carbonyl)-1H-indazol-3-yl)cyclohex-3-enecarboxylic acid;
(R or S)-4-(1-(2-chloro-6-cyclopropylbenzoyl)-6-(3-methoxyazetidine-1-carbonyl)-1H-indazol-3-yl)-1-methylcyclohex-3-enecarboxylic acid;
(S or R)-4-(1-(2-chloro-6-cyclopropylbenzoyl)-6-(3-methoxyazetidine-1-carbonyl)-1H-indazol-3-yl)-1-methylcyclohex-3-enecarboxylic acid;
(R or S)-4-(1-(2-chloro-6-cyclopropylbenzoyl)-4-fluoro-1H-indazol-3-yl)cyclohex-3-enecarboxylic acid;
(S or R)-4-(1-(2-chloro-6-cyclopropylbenzoyl)-4-fluoro-1H-indazol-3-yl)cyclohex-3-enecarboxylic acid;
4-(1-(2-chloro-6-(trifluoromethyl)benzoyl)-6-(3,3-difluoroazetidine-1-carbonyl)-1H-indazol-3-yl)cyclohex-3-enecarboxylic acid;
4-(1-(2-chloro-6-(trifluoromethyl)benzoyl)-6-(cyclopropylcarbamoyl)-1H-indazol-3-yl)cyclohex-3-enecarboxylic acid;
4-(1-(2-chloro-6-(trifluoromethyl)benzoyl)-6-(cyclopropyl(methyl)carbamoyl)-1H-indazol-3-yl)cyclohex-3-enecarboxylic acid;
4-(6-(azetidine-1-carbonyl)-1-(2-chloro-6-(trifluoromethyl)benzoyl)-1H-indazol-3-yl)cyclohex-3-enecarboxylic acid;
4-(1-(2-chloro-6-(trifluoromethyl)benzoyl)-6-(3-methoxyazetidine-1-carbonyl)-1H-indazol-3-yl)cyclohex-3-enecarboxylic acid;
4-(1-(2-chloro-6-(trifluoromethyl)benzoyl)-6-(pyrrolidine-1-carbonyl)-1H-indazol-3-yl)cyclohex-3-enecarboxylic acid;
4-(1-(2-chloro-6-(trifluoromethyl)benzoyl)-6-((S)-2-methylpyrrolidine-1-carbonyl)-1H-indazol-3-yl)cyclohex-3-enecarboxylic acid;
4-(1-(2-chloro-6-(trifluoromethyl)benzoyl)-6-((R)-2-methylpyrrolidine-1-carbonyl)-1H-indazol-3-yl)cyclohex-3-enecarboxylic acid;
4-(1-(2-chloro-6-(trifluoromethyl)benzoyl)-6-(3-methoxypyrrolidine-1-carbonyl)-1H-indazol-3-yl)cyclohex-3-enecarboxylic acid;
4-(1-(2-chloro-6-(trifluoromethyl)benzoyl)-6-(2-methylmorpholine-4-carbonyl)-1H-indazol-3-yl)cyclohex-3-enecarboxylic acid;
4-(1-(2-chloro-6-(trifluoromethyl)benzoyl)-6-(cyclohexyl(methyl)carbamoyl)-1H-indazol-3-yl)cyclohex-3-enecarboxylic acid;
4-(1-(2-chloro-6-(trifluoromethyl)benzoyl)-6-(morpholine-4-carbonyl)-1H-indazol-3-yl)cyclohex-3-enecarboxylic acid;
4-(1-(2-chloro-6-(trifluoromethyl)benzoyl)-6-((2R,6S)-2,6-dimethylmorpholine-4-carbonyl)-1H-indazol-3-yl)cyclohex-3-enecarboxylic acid;

4-(1-(2-chloro-6-(trifluoromethyl)benzoyl)-6-(4-methyl-3-oxopiperazine-1-carbonyl)-1H-indazol-3-yl)cyclohex-3-enecarboxylic acid;

4-(1-(2-chloro-6-(trifluoromethyl)benzoyl)-6-((S)-3-methylmorpholine-4-carbonyl)-1H-indazol-3-yl)cyclohex-3-enecarboxylic acid;

4-(1-(2-chloro-6-(trifluoromethyl)benzoyl)-6-(methyl(tetrahydro-2H-pyran-4-yl)carbamoyl)-1H-indazol-3-yl)cyclohex-3-enecarboxylic acid;

4-(1-(2-chloro-6-(trifluoromethyl)benzoyl)-6-((R)-3-methylmorpholine-4-carbonyl)-1H-indazol-3-yl)cyclohex-3-enecarboxylic acid;

4-(1-(2-chloro-6-(trifluoromethyl)benzoyl)-6-((S)-2-methylmorpholine-4-carbonyl)-1H-indazol-3-yl)cyclohex-3-enecarboxylic acid;

4-(1-(2-chloro-6-(trifluoromethyl)benzoyl)-6-((2-hydroxyethyl)(methyl)carbamoyl)-1H-indazol-3-yl)cyclohex-3-enecarboxylic acid;

4-(1-(2-chloro-6-(trifluoromethyl)benzoyl)-6-(isopropylcarbamoyl)-1H-indazol-3-yl)cyclohex-3-enecarboxylic acid;

4-(1-(2-chloro-6-(trifluoromethyl)benzoyl)-6-(isopropyl(methyl)carbamoyl)-1H-indazol-3-yl)cyclohex-3-enecarboxylic acid;

4-(1-(2-chloro-6-(trifluoromethyl)benzoyl)-6-((2-methoxyethyl)(methyl)carbamoyl)-1H-indazol-3-yl)cyclohex-3-enecarboxylic acid;

4-(1-(2-chloro-6-(trifluoromethyl)benzoyl)-6-(3-hydroxyazetidine-1-carbonyl)-1H-indazol-3-yl)cyclohex-3-enecarboxylic acid;

4-(1-(2-chloro-6-(trifluoromethyl)benzoyl)-6-(3-fluoroazetidine-1-carbonyl)-1H-indazol-3-yl)cyclohex-3-enecarboxylic acid;

4-(1-(2-chloro-6-(trifluoromethyl)benzoyl)-6-(piperidine-1-carbonyl)-1H-indazol-3-yl)cyclohex-3-enecarboxylic acid;

4-(1-(2-chloro-6-(trifluoromethyl)benzoyl)-6-(((1-hydroxy-3-(methylamino)propan-2-yl)oxy)carbonyl)-1H-indazol-3-yl)cyclohex-3-enecarboxylic acid;

4-(1-(2-chloro-6-(trifluoromethyl)benzoyl)-6-((S)-3-methoxypyrrolidine-1-carbonyl)-1H-indazol-3-yl)cyclohex-3-enecarboxylic acid;

4-(1-(2-chloro-6-(trifluoromethyl)benzoyl)-6-((R)-3-methoxypyrrolidine-1-carbonyl)-1H-indazol-3-yl)cyclohex-3-enecarboxylic acid;

4-(1-(2-chloro-6-(trifluoromethyl)benzoyl)-4-fluoro-1H-indol-3-yl)cyclohex-3-enecarboxylic acid;

4-(1-(2-chloro-6-(trifluoromethyl)benzoyl)-4-fluoro-1H-indazol-3-yl)-2-hydroxycyclohex-3-enecarboxylic acid;

4-(1-(2-chloro-6-(trifluoromethyl)benzoyl)-4-fluoro-1H-indazol-3-yl)-6-hydroxycyclohex-3-enecarboxylic acid;

4-(1-(2-chloro-6-(trifluoromethyl)benzoyl)-4-fluoro-1H-indazol-3-yl)-2-hydroxy-6-methylcyclohex-3-enecarboxylic acid;

4-(1-(2-chloro-6-(trifluoromethyl)benzoyl)-4-fluoro-1H-indazol-3-yl)-4-methylcyclohexanecarboxylic acid;

(trans)-4-(1-(2-chloro-6-(trifluoromethyl)benzoyl)-4-fluoro-1H-indazol-3-yl)-4-methyl cyclohexanecarboxylic acid;

(cis)-4-(1-(2-chloro-6-(trifluoromethyl)benzoyl)-4-fluoro-1H-indazol-3-yl)-4-methylcyclohexanecarboxylic acid;

(trans)-4-(1-(2-chloro-6-(trifluoromethyl)benzoyl)-4-fluoro-1H-indazol-3-yl)cyclohexanecarboxylic acid;

(cis)-4-(1-(2-chloro-6-(trifluoromethyl)benzoyl)-4-fluoro-1H-indazol-3-yl)cyclohexanecarboxylic acid;

(trans)-4-(1-(2-chloro-6-(trifluoromethyl)benzoyl)-4-fluoro-1H-indazol-3-yl)-1-methylcyclohexanecarboxylic acid;

(cis)-4-(1-(2-chloro-6-(trifluoromethyl)benzoyl)-4-fluoro-1H-indazol-3-yl)-1-methylcyclohexanecarboxylic acid;

(R and S)-4-(1-(2-chloro-6-(trifluoromethyl)benzoyl)-4-fluoro-1H-indazol-3-yl)-2,2-dimethylcyclohex-3-enecarboxylic acid;

(R and S) 4-(1-(2-chloro-6-(trifluoromethyl)benzoyl)-4-fluoro-1H-indazol-3-yl)-6,6-dimethylcyclohex-3-enecarboxylic acid;

(trans)-4-(1-(2-chloro-6-(trifluoromethyl)benzoyl)-1H-pyrazolo[4,3-b]pyridin-3-yl)cyclohexanecarboxylic acid;

(cis)-4-(1-(2-chloro-6-(trifluoromethyl)benzoyl)-1H-pyrazolo[4,3-b]pyridin-3-yl)cyclohexanecarboxylic acid;

4-(1-(2-chloro-6-(trifluoromethyl)benzoyl)-4-fluoro-1H-indazol-3-yl)-5-methylcyclohex-3-enecarboxylic acid; and 4-(1-(2-chloro-6-(trifluoromethyl)benzoyl)-4-fluoro-1H-indazol-3-yl)-4-hydroxycyclohexanecarboxylic acid.

16. A pharmaceutical composition comprising a compound of claim 1 or a pharmaceutically acceptable salt or solvate thereof, and one or more pharmaceutically acceptable excipients.

17. The pharmaceutical composition of claim 16, further comprising at least one additional therapeutically active agent.

18. A method for treating a disease or condition mediated by RORgammaT in a subject comprising administering to the subject an amount of a compound of claim 1, or a pharmaceutically acceptable salt or solvate thereof, that is effective for treating the disease or condition mediated by RORgammaT in the subject, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

19. The method of claim 18, wherein the disease or condition is multiple sclerosis, inflammatory bowel disease, Crohn's disease, ankylosing spondylitis or psoriasis.

20. The compound of claim 2, wherein the compound is a compound of Formula Ix or a pharmaceutically acceptable salt thereof; wherein $A^5$ is $CR^5$, $A^6$ is $CR^6$, and $A^7$ is $CR^7$.

21. The compound of claim 7, wherein the compound is a compound of Formula Id or a pharmaceutically acceptable salt thereof; wherein $A^5$ is $CR^5$, $A^6$ is $CR^6$, and $A^7$ is $CR^7$.

22. The compound of claim 9, wherein the compound is a compound of Formula If or a pharmaceutically acceptable salt thereof; wherein $A^5$ is $CR^5$, $A^6$ is $CR^6$, and $A^7$ is $CR^7$.

23. A pharmaceutical composition comprising a compound of claim 2 or a pharmaceutically acceptable salt thereof, and one or more pharmaceutically acceptable excipients.

24. A pharmaceutical composition comprising a compound of claim 21 or a pharmaceutically acceptable salt thereof, and one or more pharmaceutically acceptable excipients.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 25
<212> TYPE: PRT
<213> ORGANISM: Artificial Sequence
```

```
<220> FEATURE:
<223> OTHER INFORMATION: SRC1_2 peptide

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25
```